United States Patent
Zheng

(10) Patent No.: US 10,551,384 B2
(45) Date of Patent: Feb. 4, 2020

(54) MTOR KINASE MUTATIONS AND METHODS OF USE THEREOF

(71) Applicant: RUTGERS, THE STATE UNIVERSITY OF NEW JERSEY, New Brunswick, NJ (US)

(72) Inventor: Steven Zheng, New Brunswick, NJ (US)

(73) Assignee: Rutgers, The State University Of New Jersey, New Brunswick, NJ (US)

(*) Notice: Subject to any disclaimer, the term of this patent is extended or adjusted under 35 U.S.C. 154(b) by 26 days.

(21) Appl. No.: 15/482,340

(22) Filed: Apr. 7, 2017

(65) Prior Publication Data
US 2017/0299596 A1 Oct. 19, 2017

Related U.S. Application Data

(60) Provisional application No. 62/319,687, filed on Apr. 7, 2016.

(51) Int. Cl.
| | | |
|---|---|---|
| *C12Q 1/68* | (2018.01) | |
| *G01N 33/574* | (2006.01) | |
| *A61K 31/5377* | (2006.01) | |
| *A61K 31/495* | (2006.01) | |
| *A61K 31/519* | (2006.01) | |
| *A61K 31/4709* | (2006.01) | |
| *A61K 31/4745* | (2006.01) | |
| *G01N 33/50* | (2006.01) | |
| *C12Q 1/6886* | (2018.01) | |
| *C12N 9/12* | (2006.01) | |
| *A61K 31/53* | (2006.01) | |

(52) U.S. Cl.
CPC ... *G01N 33/57484* (2013.01); *A61K 31/4709* (2013.01); *A61K 31/4745* (2013.01); *A61K 31/495* (2013.01); *A61K 31/519* (2013.01); *A61K 31/53* (2013.01); *A61K 31/5377* (2013.01); *C12N 9/12* (2013.01); *C12Q 1/6886* (2013.01); *C12Y 207/11* (2013.01); *C12Y 207/11011* (2013.01); *G01N 33/5011* (2013.01); *G01N 33/57415* (2013.01); *G01N 33/57419* (2013.01); *G01N 33/57423* (2013.01); *C12Q 2600/106* (2013.01); *C12Q 2600/156* (2013.01); *G01N 2333/912* (2013.01)

(58) Field of Classification Search
None
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,683,195 A | 7/1987 | Mullis et al. |
| 4,683,202 A | 7/1987 | Mullis |
| 4,800,159 A | 1/1989 | Mullis et al. |
| 4,820,508 A | 4/1989 | Wortzman |
| 4,938,949 A | 7/1990 | Borch et al. |
| 4,965,188 A | 10/1990 | Mullis et al. |
| 4,992,478 A | 2/1991 | Geria |

OTHER PUBLICATIONS

Mateo et al; British Journal of Cancer, vol. 114, pp. 889-896, 2016.*
Carlo et al; The Oncologist, vol. 21, pp. 787-788d, 2016.*
Rodon et al; Cancer Chemotherapy and Pharmacology, vol. 82, pp. 285-298; 2018.*
Uetz et al. "A comprehensive analysis of protein-protein interactions in *Saccharomyces cerevisiae*", Nature 403, 623-627 (2000).
Vogt, "Drug-resistant phosphatidylinositol 3-kinase: guidance for the preemptive strike", Cancer Cell 14, 107-108 (2008).
Wood, et al., "The genomic landscapes of human breast and colorectal cancers", Science 318, 1108-1113 (2007).
Wu, et al., "Identification of a Non-Gatekeeper Hotspot for Drug Resistant Mutations in mTOR Kinase", Cell Rep 11(3), 446-459 (2015).
Wullschleger, et al., "TOR signaling in growth and metabolism", Cell 124, 471-484 (2006).
Yang, et al., "mTOR kinase structure, mechanism and regulation by the rapamycin-binding domain", Nature 497, 217-223 (2013).
Zhang, et al., "mTOR Signaling is Involved in Indomethacin and Nimesulide Suppression of Colorectal Cancer Cell Growth via a COX-2 Independent Pathway", Ann Surg Oncol 18, 580-588 (2011).
Zhang et al., "mTOR-independent 4E-BP1 phosphorylation is associated with cancer resistance to mTOR kinase inhibitors", Cell Cycle 11, 594-603 (2012).
Zhang, et al., "Targeting cancer with small molecule kinase inhibitors", Nature Reviews Cancer 9, 28-39 (2009).
Zhang, et al., "Targeting the mTOR kinase domain: the second generation of mTOR inhibitors", Drug Discov Today 16, 325-331 (2011).
Zheng, et al., "TOR Kinase Domains Are Required for Two Distinct Functions, Only One of Which is Inhibited by Rapamycin", Cell 82, 121-130 (1995).
Zunder, et al., "Discovery of Drug-Resistant and Drug-Sensitizing Mutations in the Oncogenic PI3K Isoform p110α", Cancer Cell 14, 180-192 (2008).
Alarcon, et al., "Mammalian RAFT1 kinase domain provides rapamycin-sensitive TOR function in yeast", Genes and Development 10, 279-288 (1996).
Azam, et al., "Mechanisms of Autoinhibition and STI-571/Imatinib Resistance Revealed by Mutagenesis of BCR-ABL", Cell 112, 831-843 (2003).
Bell, et al., "Inherited susceptibility to lung cancer may be associated with the T790M drug resistance mutation in EGFR", Nat Genet 37, 1315-1316 (2005).

(Continued)

*Primary Examiner* — Jehanne S Sitton
(74) *Attorney, Agent, or Firm* — Viksnins Harris Padys Malen LLP

(57) ABSTRACT

Certain embodiments of the invention provide a method of detecting the presence of a biomarker associated with resistance to an mTOR kinase inhibitor in a subject, comprising determining the presence of the biomarker in a physiological sample from the subject, wherein the sample comprises a nucleic acid.

11 Claims, 13 Drawing Sheets

Specification includes a Sequence Listing.

(56) References Cited

OTHER PUBLICATIONS

Bjornsti, et al., "The TOR pathway: a target for cancer therapy", Nat Rev Cancer 4, 335-348 (2004).
Chen, et al., "Identification of an 11-kDa FKBP12-rapamycin-binding domain within the 289-kDa FKBP12-rapamycin-associated protein and characterization of a critical serine residue", PNAS 92, 4947-4951 (1995).
Cong, et al., "Multiplex Genome Engineering Using CRISPR/Cas Systems", Science 339, 819-823 (2013).
Dohmen, et al., "Heat-inducible degron and the making of conditional mutants", Methods Enzymol 399, 799-822 (2005).
Dunstan, et al., "Cell-Based Assays for Identification of Novel Double-Strand Break-Inducing Agents", Journal of National Cancer Institute 94, 88-94 (2002).
Emter, et al., "ERG6 and PDR5 regulate small lipophilic drug accumulation in yeast cells via distinct mechanisms", FEBS Letters 521, 57-61 (2002).
Engelman, et al., "Allelic dilution obscures detection of a biologically significant resistance mutation in EGFR-amplified lung cancer", Journal of Clinical Investigation 116, 2695-2706 (2006).
Feldman, et al., "Active-Site Inhibitors of mTOR Target Rapamycin-Resistant Outputs of mTORC1 and mTORC2", PLoS Biology 7, e38, 13 pages (2009).
Gaber, et al., "The yeast gene ERG6 is required for normal membrane function but is not essential for biosynthesis of the cell-cycle-sparking sterol", Molecular and Cellular Biology 9, 3447-3456 (1989).
Ghannoum, et al., "Antifungal Agents: Mode of Action, Mechanisms of Resistance, and Correlation of These Mechanisms with Bacterial Resistance", Clinical Microbiology Reviews 12, 501-517 (1999).
Gild, et al., "Targeting mTOR in RET mutant medullary and differentiated thyroid cancer cells", Endocrine-Related Cancer 20, 659-667 (2013).
Gorre, et al., "Clinical resistance to STI-571 cancer therapy caused by BCR-ABL gene mutation or amplification", Science 293, 876-880 (2001).
Gray, et al., "Exploiting chemical libraries, structure, and genomics in the search for kinase inhibitors", Science 281, 533-538 (1998).
Guertin, et al., "Defining the role of mTOR in cancer", Cancer Cell 12, 9-22 (2007).
Guertin, et al., "The Pharmacology of mTOR Inhibition", Sci Signal 2(67), pe24 (2009).
Hayman, et al., "The ATP-Competitive mTOR Inhibitor INK128 enhances in vitro and in vivo radiosensitivity of pancreatic carcinoma cells", Clinical Cancer Research 20, 110-119 (2014).
Heinrich, et al., "Kinase Mutations and Imatinib Response in Patients With Metastatic Gastrointestinal Stromal Tumor", Journal of Clinical Oncology 21, 4342-4349 (2003).
Hsieh, et al., "The translational landscape of mTOR signalling steers cancer initiation and metastasis", Nature 485, 55-61 (2012).
Hu, et al., "Allosteric Activation of Functionally Asymmetric RAF Kinase Dimers", Cell 154, 1036-1046 (2013).
Hu, et al., "Mutation that blocks ATP binding creates a pseudokinase stabilizing the scaffolding function of kinase suppressor of Ras, CRAF and BRAF", PNAS 108(15), 6067-6072 (2011).
Kennedy, et al., "Identifying Critical Non-Catalytic Residues that Modulate Protein Kinase A Activity", PLoS One 4, e4746 (2009).
Kobayashi, et al., "EGFR Mutation and Resistance of Non-Small-Cell Lung Cancer to Gefitinib", New England Journal of Medicine 352, 786-792 (2005).
Kornev, et al., "Surface comparison of active and inactive protein kinases identifies a conserved activation mechanism", PNAS 103(47), 17783-17788 (2006).
Liu, et al., "Rational design of inhibitors that bind to inactive kinase conformations", Nature Chemical Biology 2, 358-364 (2006).
Liu, et al., "Selective ATP-Competitive Inhibitors of TOR Suppress Rapamycin-Insensitive Function of TORC2 in *Saccharomyces cerevisiae*", ACS Chemical Biology 7, 982-987 (2012).
Loewith, et al., "Two TOR complexes, only one of which is rapamycin sensitive, have distinct roles in cell growth control", Mol Cell 10, 457-468 (2002).
Ma, et al., "Molecular mechanisms of mTOR-mediated translational control", Nat Rev Mol Cell Biol 10, 307-318 (2009).
Mali, et al., "RNA-guided human genome engineering via Cas9", Science 339, 823-826 (2013).
Martzen, et al., "A biochemical genomics approach for identifying genes by the activity of their products", Science 286, 1153-1155 (1999).
Meharena, et al., "Deciphering the Structural Basis of Eukaryotic Protein Kinase Regulation", PLoS Biology 11, e1001680, 10 pages (2013).
Nielsen, et al., "Sequence-selective recognition of DNA by strand displacement with a thymine-substituted polyamide", Science 254 (5037), 1497-1500 (1991).
O'Reilly, et al., "mTOR Inhibition Induces Upstream Receptor Tyrosine Kinase Signaling and Activates Akt", Cancer Research 66, 1500-1508 (2006).
Pao, et al., "Acquired Resistance of Lung Adenocarcinomas to Gefitinib or Erlotinib Is Associated with a Second Mutation in the EGFR Kinase Domain", PLoS Med 2, e73 (2005).
Ran, et al., "Genome engineering using the CRISPR-Cas9 system", Nature Protocols 8, 2281-2308 (2013).
Sancak, et al., "PRAS40 is an insulin-regulated inhibitor of the mTORC1 protein kinase", Molecular Cell 25, 903-915 (2007).
Santos, et al., "Bafetinib, a dual Bcr-Abl/Lyn tyrosine kinase inhibitor for the potential treatment of leukemia", Curr Opin Investig Drugs 11, 1450-1465 (2010).
Sarbassov, et al., "Phosphorylation and regulation of Akt/PKB by the rictor-mTOR complex", Science 307, 1098-1101 (2005).
Sarbassov, et al., "Rictor, a novel binding partner of mTOR, defines a rapamycin-insensitive and raptor-independent pathway that regulates the cytoskeleton", Curr Biol 14, 1296-1302 (2004).
Shaw, et al., "Kinases and Pseudokinases: Lessons from RAF", Molecular and Cellular Biology 34, 1538-1546 (2014).
Simon, et al., "Yeast as a model system for anticancer drug discovery", Nature Reviews Cancers 4, 481-492 (2004).
Sturgill, et al., "Activating Mutations in TOR Are in Similar Structures As Oncogenic Mutations in PI3KCα", ACS Chemical Biology 4, 999-1015 (2009).
Sun, et al., "Activation of Akt and eIF4E Survival Pathways by Rapamycin-Mediated Mammalian Target of Rapamycin Inhibition", Cancer Research 65, 7052-7058 (2005).
Taylor, et al., "Protein kinases: evolution of dynamic regulatory proteins", Trends in Biochemical Sciences 36, 65-77 (2011).
Thomas, et al., "Rab1A Is an mTORC1 Activator and a Colorectal Oncogene", Cancer Cell 26, 754-769 (2014).
Thoreen, et al., "An ATP-competitive mammalian target of rapamycin inhibitor reveals rapamycin-resistant functions of mTORC1", J Biol Chem 284, 8023-8032 (2009).
Tokarski, et al., "The structure of Dasatinib (BMS-354825) bound to activated ABL kinase domain elucidates its inhibitory activity against imatinib-resistant ABL mutants", Cancer Research 66, 5790-5797 (2006).
Tsang, et al., "Targeting mammalian target of rapamycin (mTOR) for health and diseases", Drug Discov Today 12, 112-124 (2007).

\* cited by examiner

FIGURES 1A-E
A
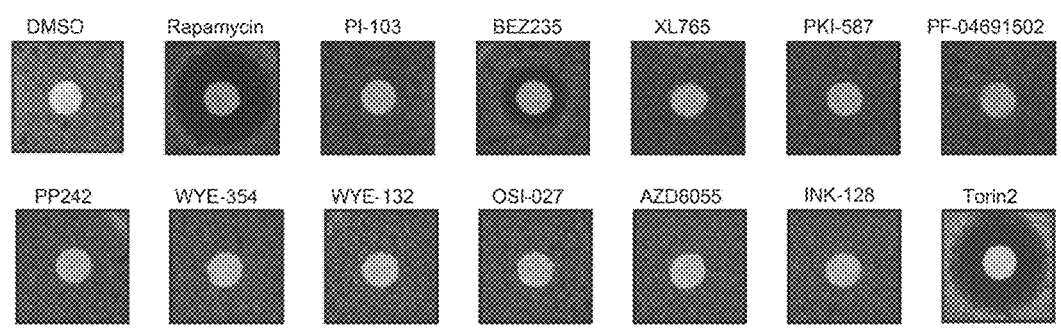
B
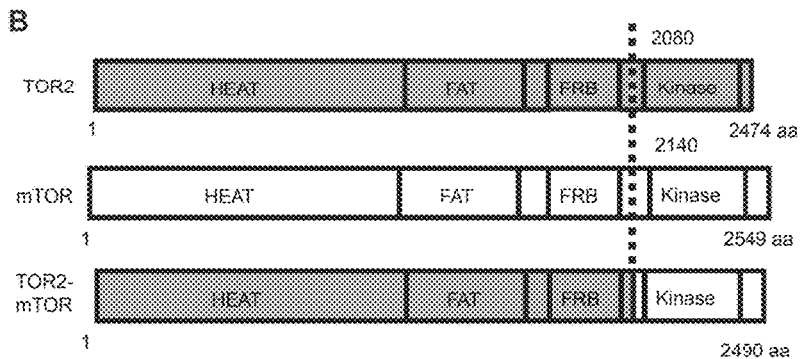
C
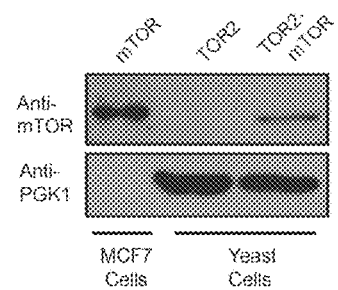
D
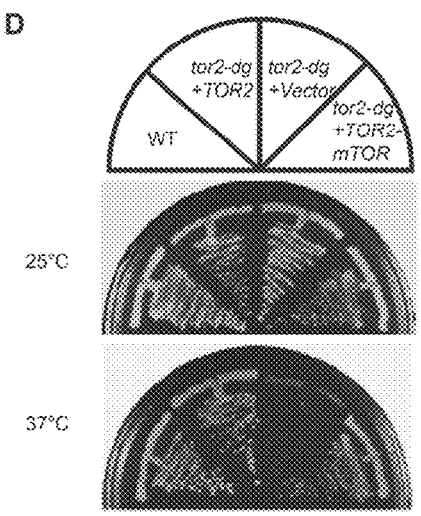
E
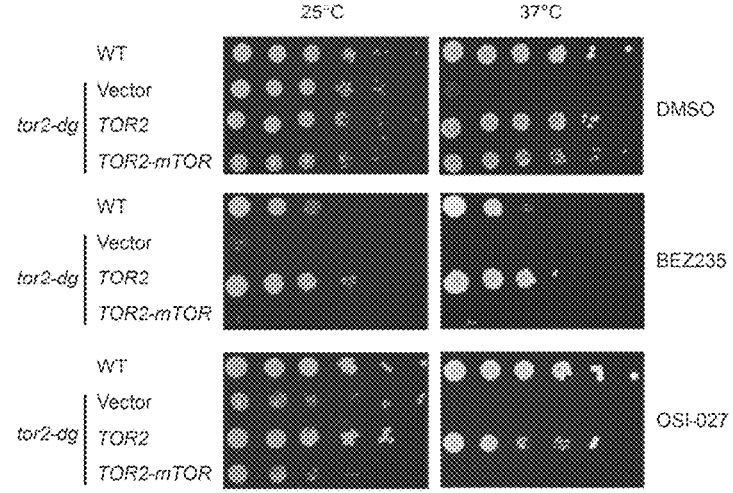

FIGURES 2A-C
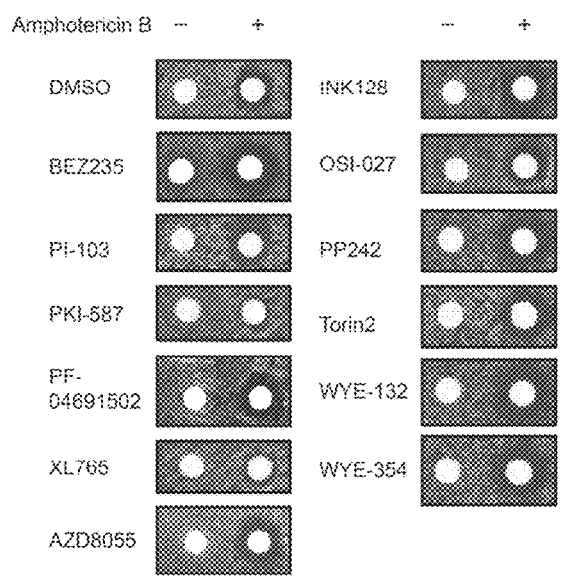
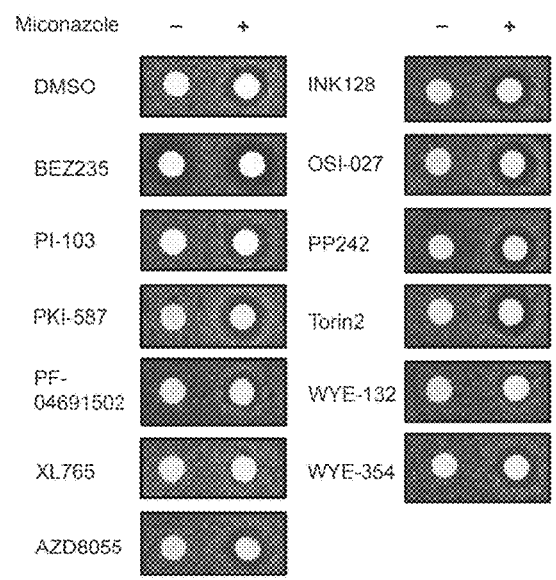
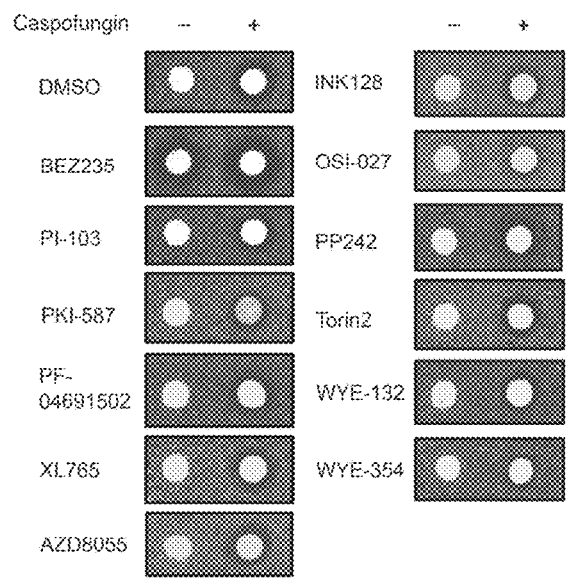

FIGURES 3A-E
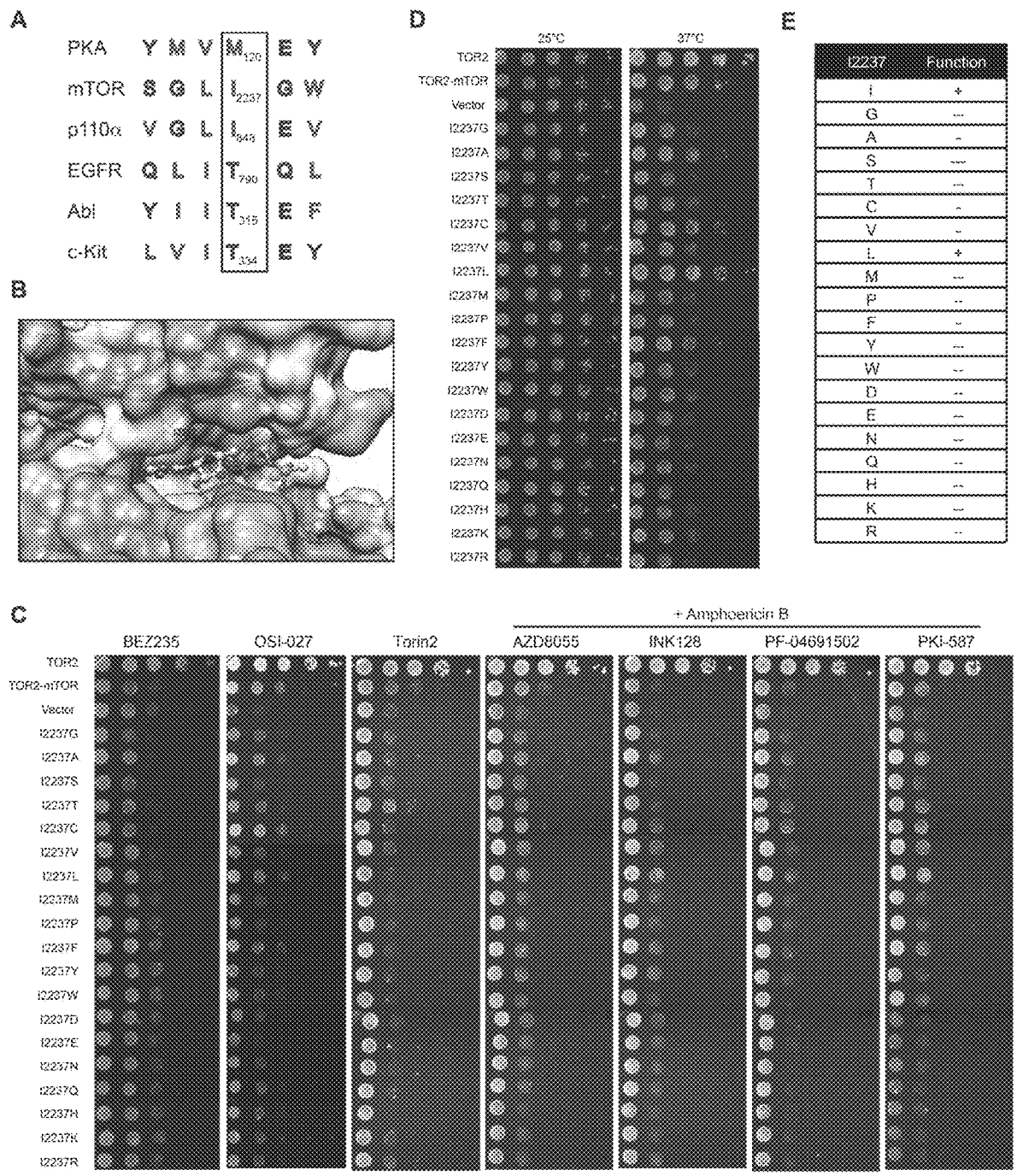

FIGURES 4A-C
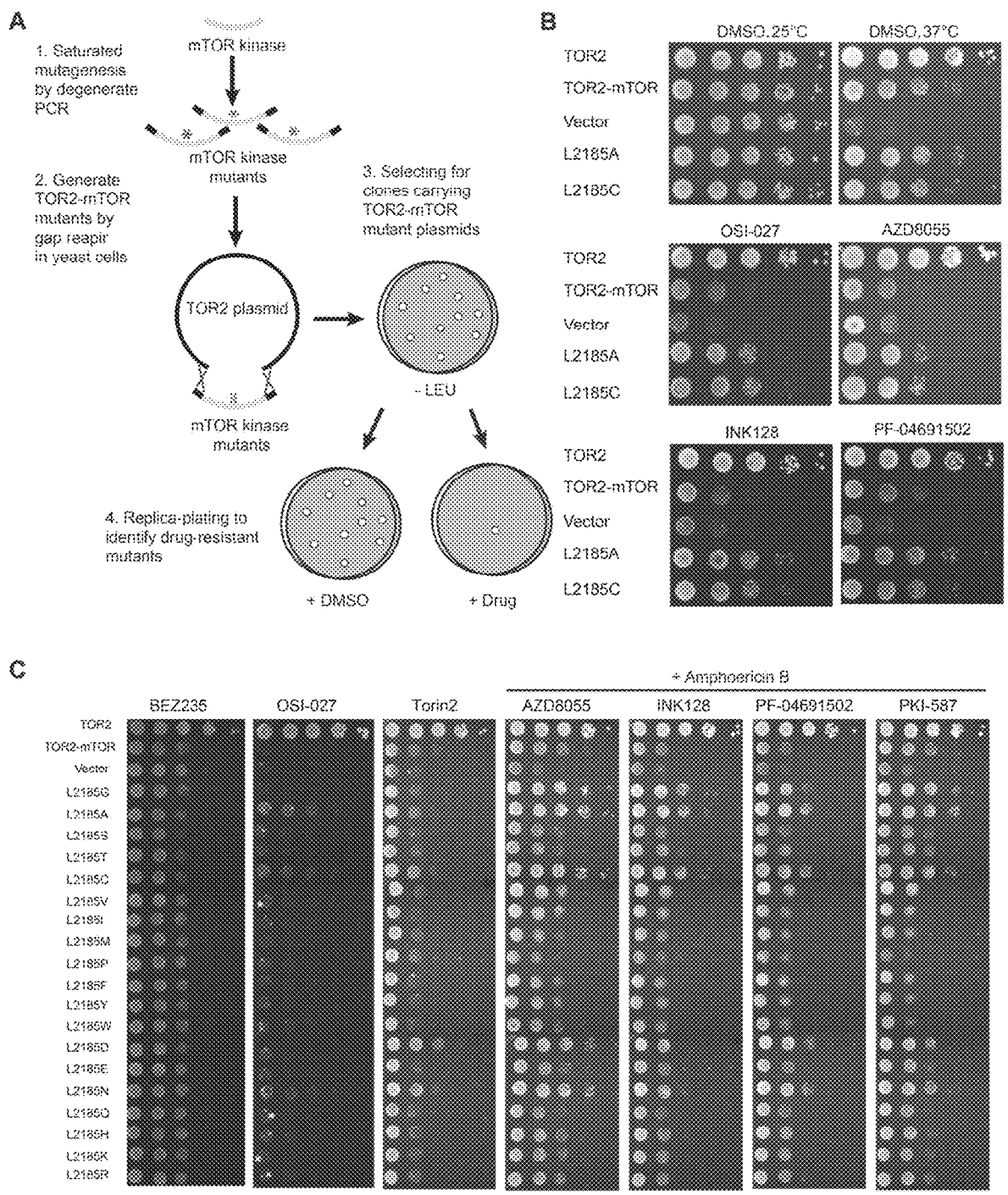

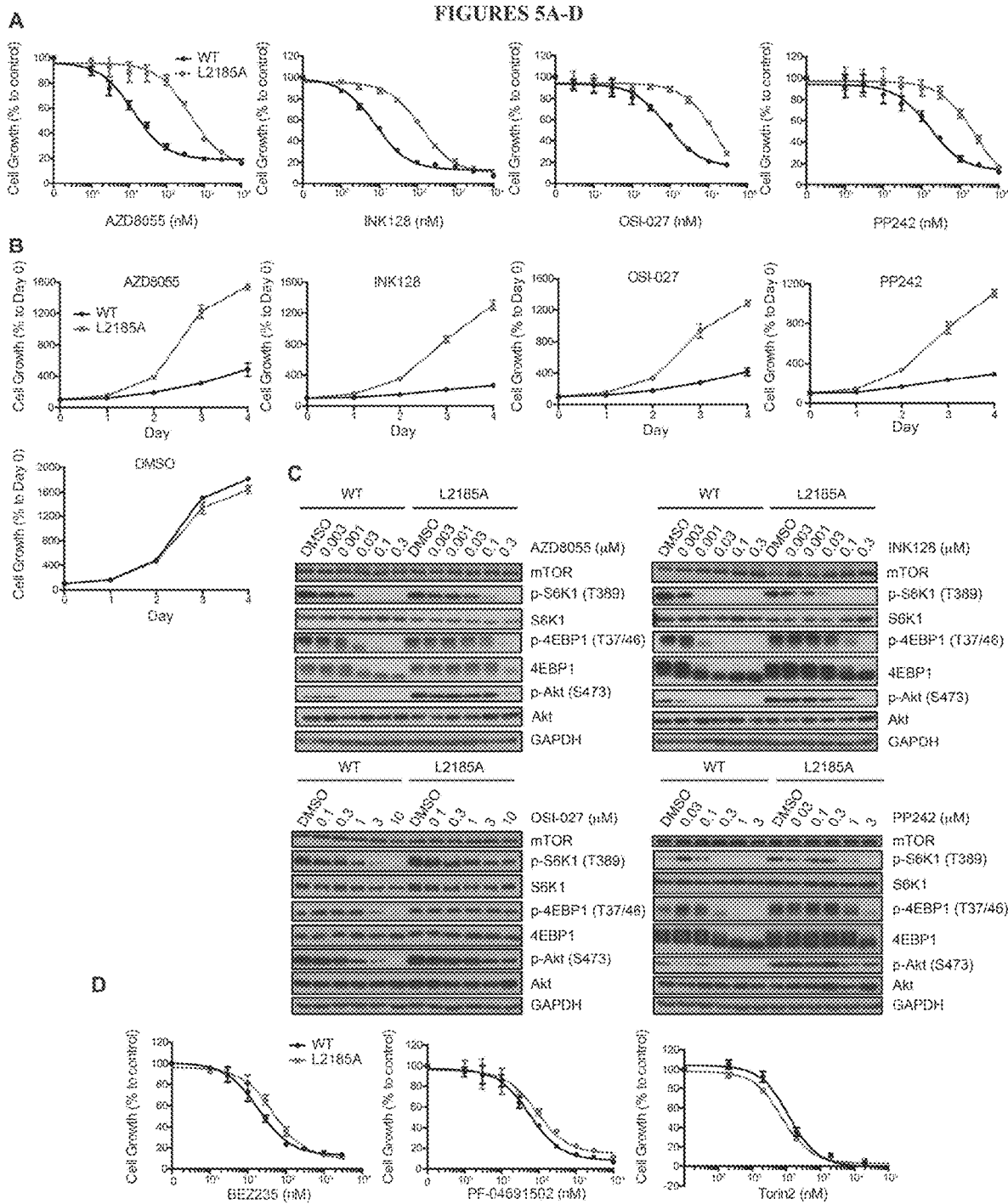
FIGURES 5A-D

FIGURES 6A-E
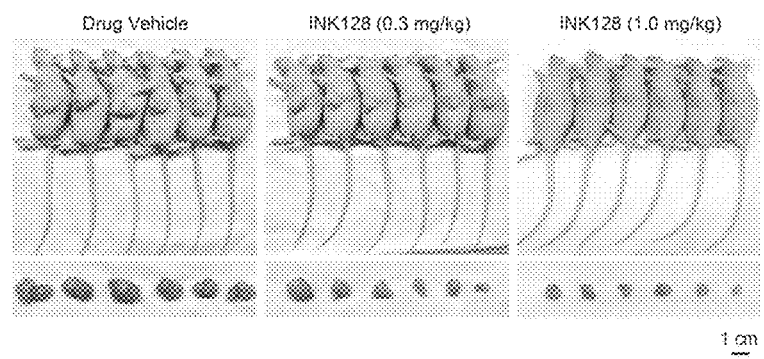
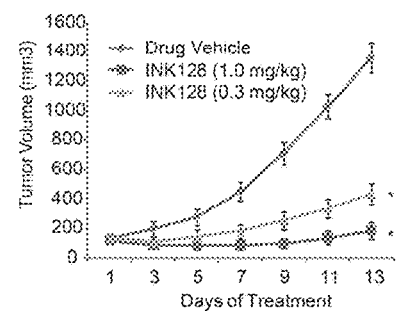
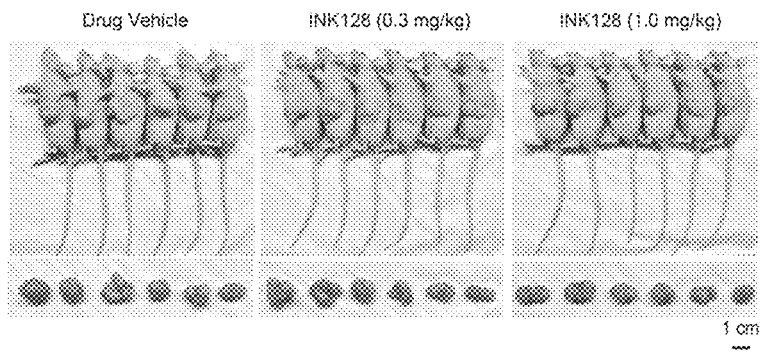
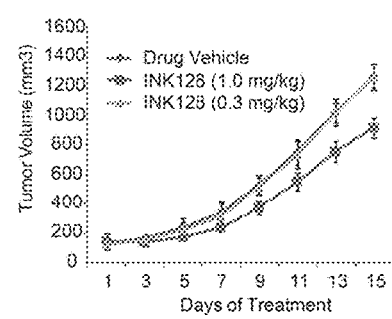
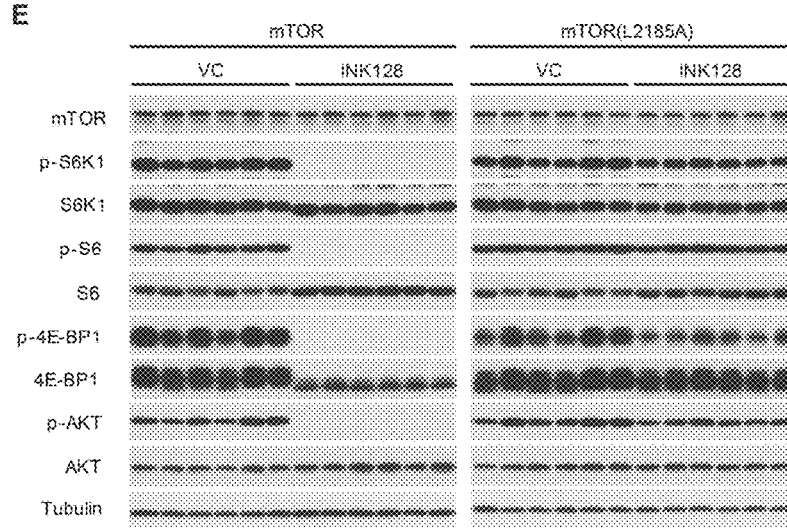

FIGURES 7A-F
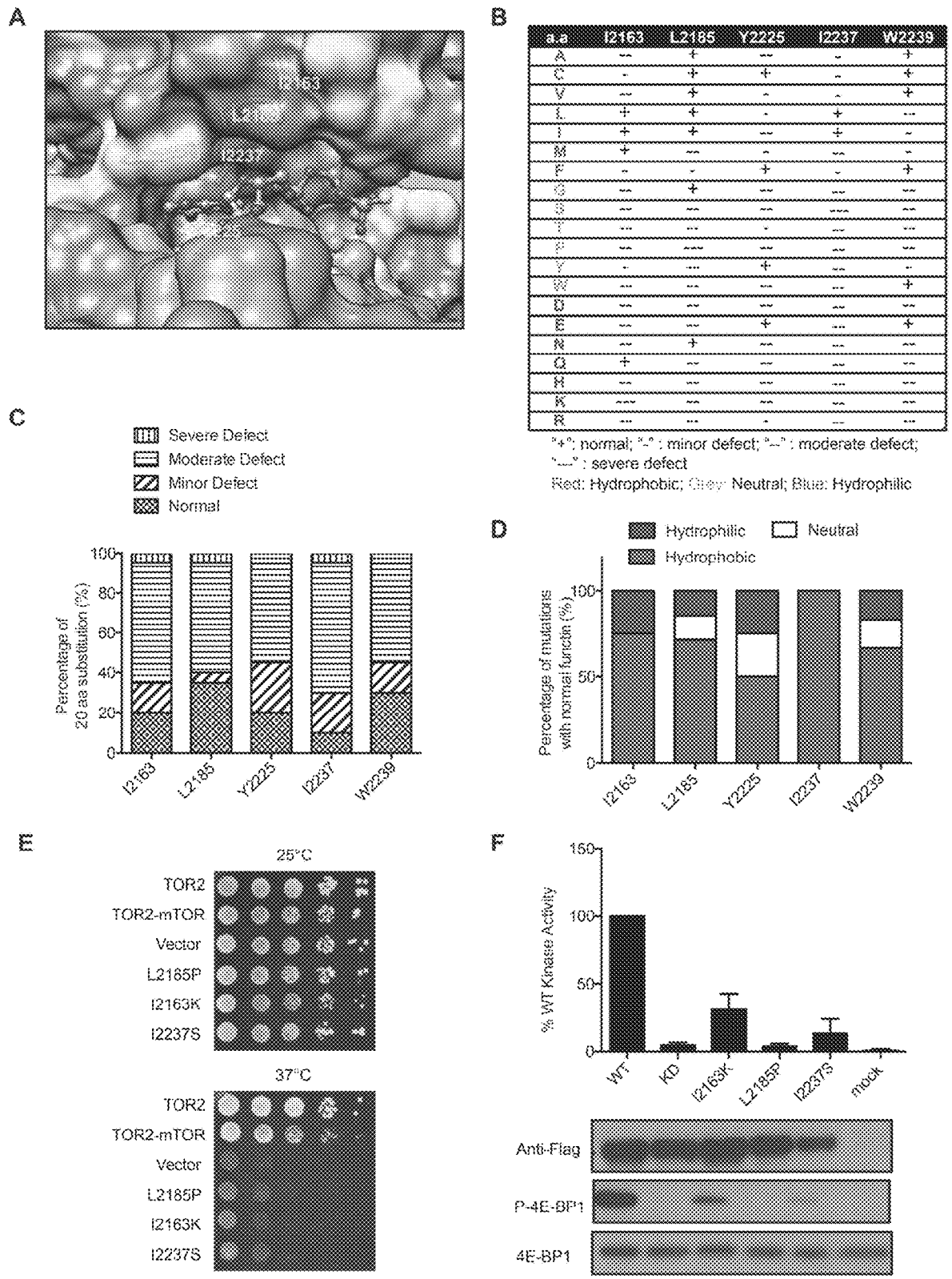

FIGURE 9

```
                    10              20            30           40          50
DNA-PK (3227)  T VMA LR PKR I I RCHDE- - - - - - - R E PF V GG D QRV E FQVMN
ATR (2301)     E LA LQ PKK S KGSDG- - - - - - - K F IMM PK CR M NS N
ATM (2691)     R G VNLPK DCVGSDG- - - - - - - K ERRQ  GR D AVMQ V QMCN
PIK3CG (802)   K MA KK PLW E KCADPTALSN - - - - ET C HG M R ME
PIK3CD (750)   T MD KM PLW M S - - NEEAGSG - - - GSVG  NC M Q MD
PIK3CB (777)   K MD KM PLW V N - - NKVFGE - - - - DS VG  NC M R MD
PIK3CA (770)   R MS AK PLW NWE - - NPDIMSELLFQNNE  NC M R ME
mTOR (2161)    Q T KQ PRK T LMGSNG - - - - - - - HE V GH  ER VM G VN
               2163                              2185

60              70            80           90         100
DNA-PK (3227)  G AQ S C SQRA Q RT SVVPMT S LG  EN V KD LLNT - - - - - MS
ATR (2301)     K RK AESRRR H R T AV P N CG  VNN AG RP LT - - - - - - - KL
ATM (2691)     T QRNTETRKRK T CT KVVP SQ SGV  T VP GE LVNNED AHKR
PIK3CG (802)   S WET S - - - - C LP C G  GM VKDAT AK - - - - - - - - - -
PIK3CD (750)   V WKQ G - - - - RMTP CC P G  T G V LR D AN - - - - - - - - - -
PIK3CB (777)   L WKEA - - - - RML P CC A GD SG  V ST E AD - - - - - - - - - -
PIK3CA (770)   N WQNQ G - - - - RML P CC GDCVG  V RN H MQ - - - - - - - - - -
mTOR (2161)    T AN P SLRKN S QR AV P STNSG V HC A I - - - - - - - RD
                             2225           2237 2239
```

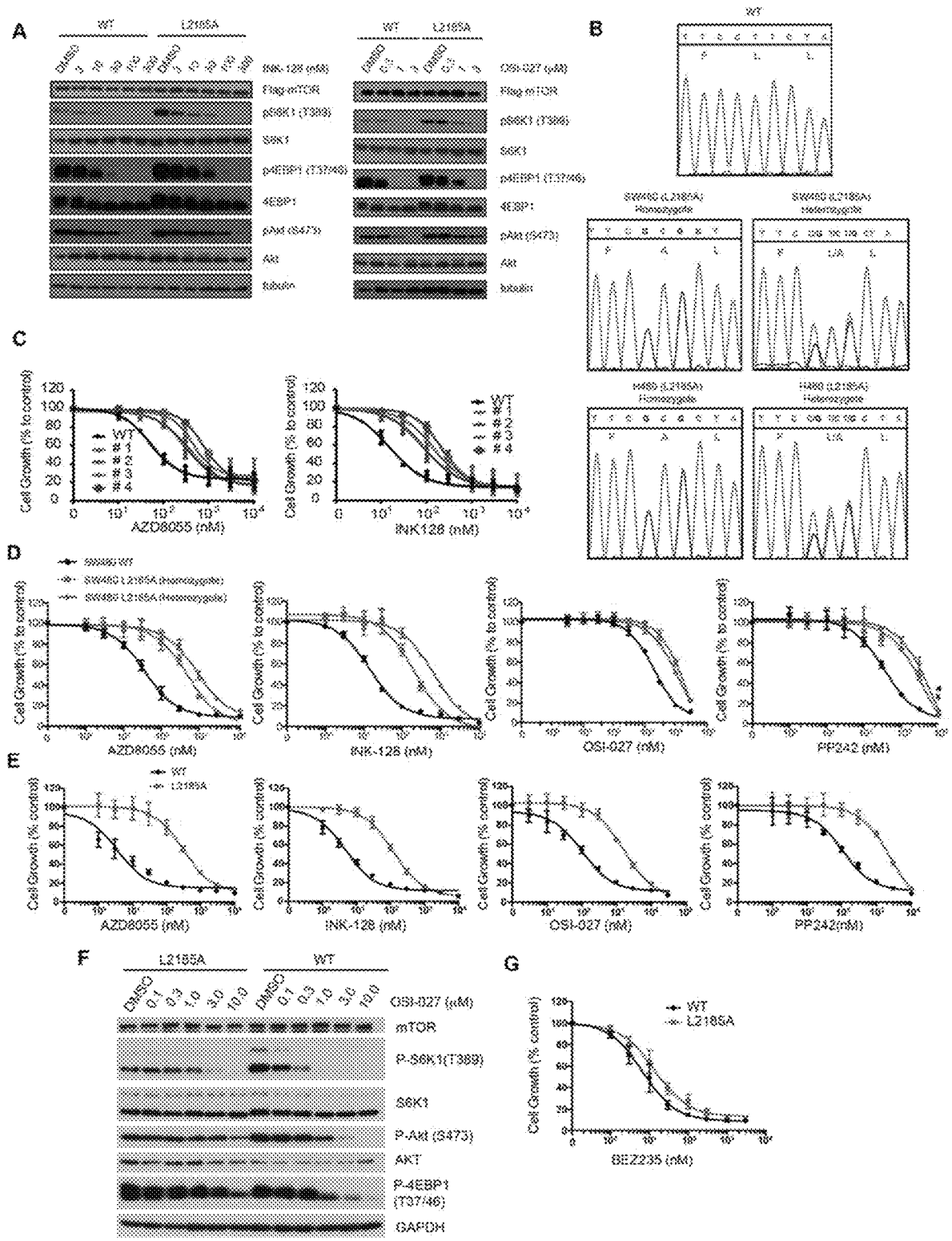
FIGURES 10A-G

FIGURES 11A-C
A
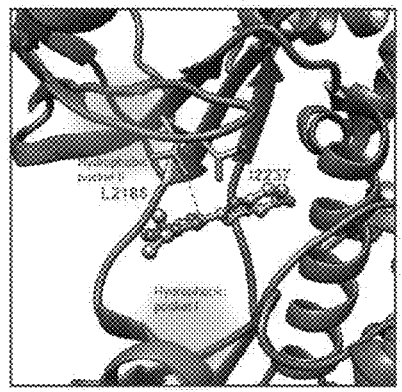
mTOR-PP242
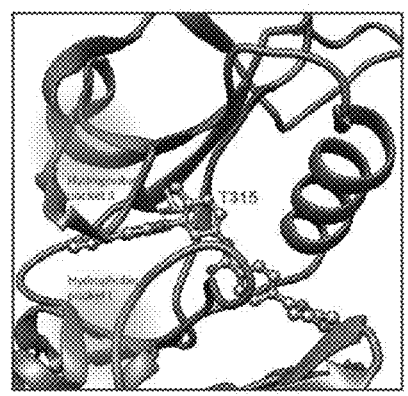
c-ABL-imatinib
B
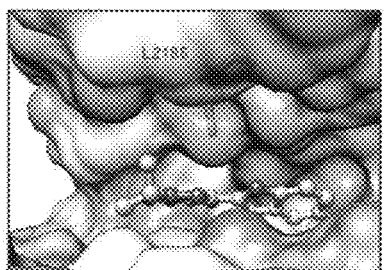
mTOR-PP242
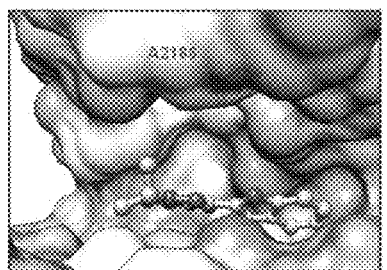
mTOR (L2185A)-PP242
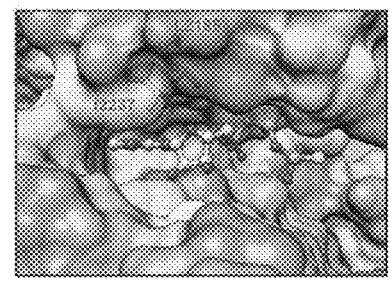
mTOR-ATP
C
|  | PP242 | Torin2 | ATP |
|---|---|---|---|
| mTOR |  | 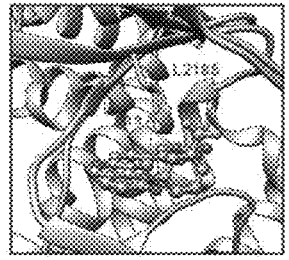 | 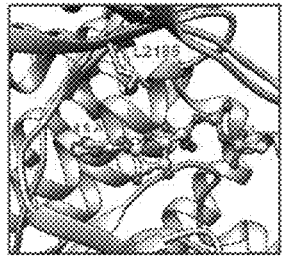 |
| mTOR (L2185A) | | 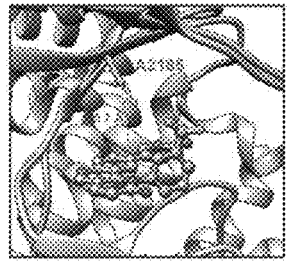 | 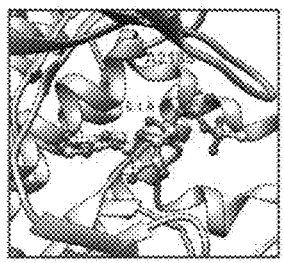 |

FIGURES 11D-F
D
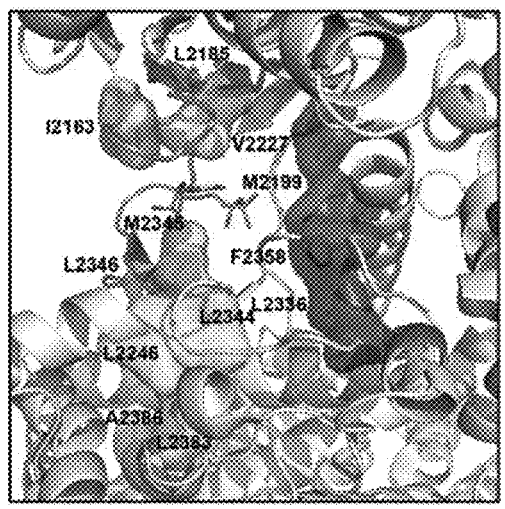 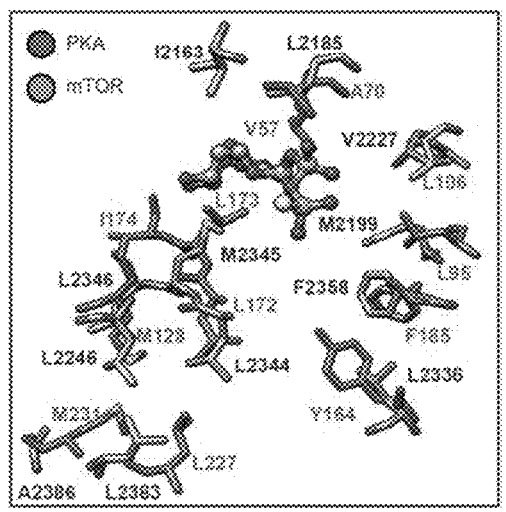
E
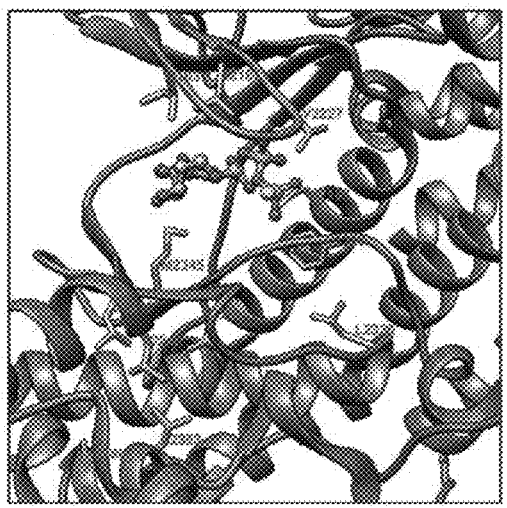 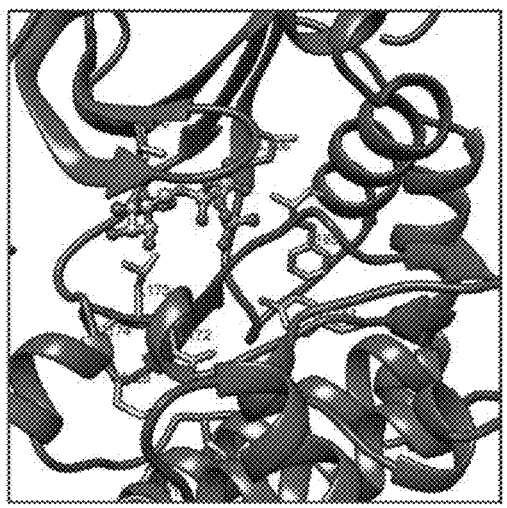
mTOR  PKA
F
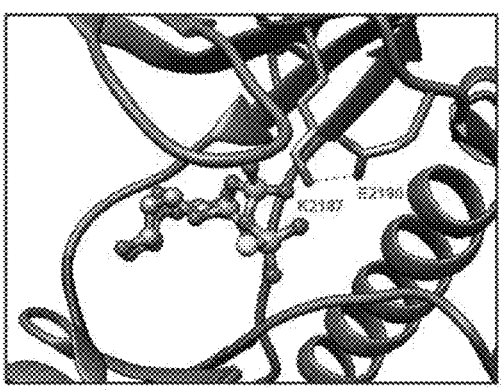 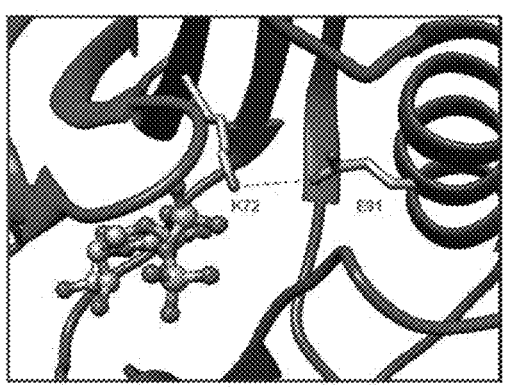
mTOR  PKA

MTOR KINASE MUTATIONS AND METHODS OF USE THEREOF

RELATED APPLICATION

This application claims the benefit of priority of U.S. Provisional Application Ser. No. 62/319,687 filed on Apr. 7, 2016, which application is incorporated by reference herein.

GOVERNMENT FUNDING

This invention was made with government support under P30-CA072720 awarded by the National Cancer Institute and R01 CA123391 and R01 CA166575 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 31, 2017, is named 08035.093US1.txt and is 70,116 bytes in size.

BACKGROUND OF THE INVENTION

Mechanistic Target of Rapamycin (mTOR) is a highly conserved serine/threonine protein kinase belonging to the PI3K-related kinase (PIKK) family (Wullschleger, et al. (2006). Cell 124, 471-484). mTOR forms two distinct kinase complexes, mTORC1 and mTORC2. mTORC1 controls cell growth and metabolism, in response to diverse cellular signals, including nutrients, growth factors and cytokines (Ma, X., and Blenis, J. (2009). Nat Rev Mol Cell Biol 10, 307-318). mTORC2 phosphorylates AKT at Ser473 and promotes cell survival (Sarbassov, et al. (2005). Science 307, 1098-1101). Recent advances in cancer genomic sequencing have revealed cancer mutations frequently target mTOR pathway, resulting in hyperactivation of mTOR signaling that drives uncontrolled cancer growth, metabolism and survival (Wood, et al. (2007). Science 318, 1108-1113). mTOR is an established molecular target for cancer therapy, because cancer cells tend to be addicted to aberrant mTOR signaling and mTOR inhibition is well tolerated (Bjornsti, M.-A., and Houghton, P. J. (2004). Nat Rev Cancer 4, 335-348; Guertin, D., and Sabatini, D. (2007). Cancer Cell 12, 9-22; Tsang, et al. (2007). Drug Discov Today 12, 112-124).

Since mTOR kinase inhibitors were described in 2008, numerous mTOR kinase targeting agents have been developed and entered into human clinical trials for cancer treatment (Zhang, et al. (2011a). Drug Discov Today 16, 325-331). The remarkable speed with which human clinical trials have been initiated and the sheer number of different compounds being tested in patients underscore the therapeutic potential of these inhibitors. Despite early promising results, major challenges remain. For example, a comprehensive, mechanistic understanding of these small molecule inhibitors is lacking. Additionally, while other small molecule kinase inhibitors have been proven clinically effective against malignancies in which kinase targets are hyperactivated, tumors typically develop drug resistance within six months after initial treatment. A major mechanism underpinning acquired resistance to kinase inhibitors is binding site mutations Gorre, et al. (2001). Science (New York, N.Y.) 293, 876-880; Heinrich, et al. (2003). Journal of clinical oncology: official journal of the American Society of Clinical Oncology 21, 4342-4349; Kobayashi, et al. (2005). New England Journal of Medicine 352, 786-792). Thus, identification of resistant mutations is crucial for clinical diagnosis and development of new strategies to overcome resistant variants.

Thus, there is a need for additional tools to investigate mTOR kinase function, for the development and evaluation of mTOR kinase inhibitors and/or for the clinical diagnosis of drug-resistance. For example, there is a need for the identification of drug-resistant mutations in the mTOR kinase domain, which may be used as biomarkers for resistance and treatment decisions, as well as for the development and screening of new inhibitors.

SUMMARY OF THE INVENTION

Targeted therapeutics has fundamentally changed cancer treatment. However, binding site mutations are known to cause acquired clinical resistance, limiting long-term therapeutic efficacy. mTOR kinase is a highly conserved central regulator of cell growth and metabolism, and a key cancer drug target. Numerous mTOR kinase inhibitors have been developed, with some already in human clinical trials. As described herein, a hotspot in the drug-binding site of mTOR kinase was identified, and when mutated to certain amino acid residues, causes drug-resistance and renders drug-refractory cancer growth. This hotspot may be used, e.g., as a biomarker for the clinical diagnosis of acquired drug-resistance, as well as for designing next generation drugs to overcome resistance for mTOR kinase inhibitors.

Certain embodiments of the invention provide a method of detecting the presence of a biomarker associated with resistance to an mTOR kinase inhibitor in a subject, comprising determining the presence of the biomarker in a physiological sample from the subject, wherein the sample comprises a nucleic acid.

Certain embodiments of the invention provide a method for identifying resistance to an mTOR kinase inhibitor in a subject, comprising detecting the presence of a biomarker in a physiological sample from the subject, wherein the sample comprises a nucleic acid, and wherein the presence of the biomarker is indicative of resistance to an mTOR kinase inhibitor.

Certain embodiments of the invention provide a method for identifying a cancer in a subject that is resistant to an mTOR kinase inhibitor, comprising:

a) obtaining a physiological sample comprising a cancer cell(s) from the subject; and $b_1$) detecting the presence of at least one mutation in a mTOR polynucleotide in the cancer cell(s), wherein the at least one mutation results in an amino acid substitution at residue L2185 of the mTOR polypeptide; or $b_2$) detecting the presence of a mutation at residue L2185 of a mTOR polypeptide in the cancer cell(s);

wherein the presence of the mutation is indicative of resistance to an mTOR kinase inhibitor. In certain embodiments, the at least one mutation is located at a nucleotide position corresponding to 137,970, 137,971 and/or 137,972 of mTOR gene NG_033239. In certain embodiments, the at least one mutation is selected from the group consisting of GCT, GCC, GCA, GCG, TGT, TGC, GTT, GTC, GTA, GTG, GAT, GAC, AAT and AAC, present at nucleotide positions corresponding to 137,970-137,972 of mTOR gene NG_033239. In certain embodiments, the mutation is selected from L2185A, L2185C, L2185D, L2185N and L2185G. In certain embodiments, the cancer is colorectal cancer, lung cancer or breast cancer.

In certain embodiments, the detecting step is by allele specific hybridization, size analysis, sequencing, hybridization, 5' nuclease digestion, single-stranded conformation polymorphism, primer specific extension, oligonucleotide ligation assay, an antibody, Western blot, an immunohistochemical assay and/or an ELISA assay.

In certain embodiments, the presence of the mutation is indicative of resistance to an mTOR kinase inhibitor that does not comprise a three-ring fused heterocyclic structure. In certain embodiments, the presence of the mutation is indicative of resistance to an mTOR kinase inhibitor selected from OSI-027, AZD8055, INK128 (i.e., TAK-228, MLN0128, Sapanisertib), PF-04691502, PKI-587 (i.e., Gedatolisib, PF-05212384) and derivatives thereof. In certain embodiments, the absence of the mutation is indicative of sensitivity to an mTOR kinase inhibitor that comprises a three-ring fused heterocyclic structure.

Certain embodiments of the invention provide a method of treating cancer in subject comprising:
 a) detecting the presence or absence of a biomarker in a physiological sample obtained from the subject, wherein the sample comprises a cancer cell(s), and wherein the biomarker comprises 1) at least one mutation in a mTOR polynucleotide that results in an amino acid substitution at residue L2185 of a mTOR polypeptide; or 2) a mutation at residue L2185 of a mTOR polypeptide;
 b) selecting an mTOR kinase inhibitor for administration to the subject based on the presence or absence of the biomarker; and
 c) administering an effective amount of the selected mTOR kinase inhibitor to the subject to treat the cancer.

In certain embodiments, the presence of the biomarker is detected and an mTOR kinase inhibitor having a three-ring fused heterocyclic structure is selected for administration to the subject. In certain embodiments, the mTOR kinase inhibitor having a three-ring fused heterocyclic structure is BEZ235, Torin2, or derivatives thereof. In certain embodiments, the absence of the biomarker is detected and an mTOR kinase inhibitor without a three-ring fused heterocyclic structure is selected for administration to the subject. In certain embodiments, the mTOR kinase inhibitor without a three-ring fused heterocyclic structure is OSI-027, AZD8055, INK128, PF-04691502, PKI-587 or derivatives thereof.

In certain embodiments, the amino acid substitution/mutation is selected from L2185A, L2185C, L2185D, L2185N and L2185G.

In certain embodiments, the cancer is colorectal cancer, lung cancer or breast cancer.

Certain embodiments of the invention provide a method of treating cancer in a subject comprising administering an effective amount of a mTOR kinase inhibitor to the subject, wherein the cancer was determined to comprise 1) at least one mutation in a mTOR polynucleotide that results in an amino acid substitution at residue L2185 of a mTOR polypeptide; or 2) a mutation at residue L2185 of a mTOR polypeptide.

Certain embodiments of the invention provide a kit for identifying a cancer in a subject that is resistant to an mTOR kinase inhibitor, the kit comprising:
 a) a first primer oligonucleotide that hybridizes 5' or 3' to at least one mutation (i.e., a nucleotide base substitution) located at nucleotide positions corresponding to 137,970, 137,971 and/or 137,972 of mTOR gene NG_033239; and/or
 b) an allele specific oligonucleotide that is specific for a mutation (i.e., a nucleotide base substitution) that results in an amino acid substitution at residue L2185 of a mTOR polypeptide;
 wherein the first primer oligonucleotide and/or the allele specific oligonucleotide comprises a detection means (e.g., a fluorescent or radioactive label).

Certain embodiments of the invention provide an isolated or purified nucleic acid comprising a mTOR cDNA nucleic acid sequence, or a portion thereof, wherein the nucleic acid comprises at least one mutation at a position corresponding to 6674, 6675 and/or 6676 of SEQ ID NO:2. In certain embodiments, the nucleic acid is about 20 to about 10,000 nucleotides in length. In certain embodiments, the nucleic acid sequence has at least about 90% sequence identity to SEQ ID NO:2, wherein the nucleic acid comprises at least one mutation (i.e., a nucleotide base substitution) at position 6674, 6675 and/or 6676. In certain embodiments, the at least one mutation is selected from the group consisting of GCT, GCC, GCA, GCG, TGT, TGC, GTT, GTC, GTA, GTG, GAT, GAC, AAT and AAC, present at nucleotide positions corresponding to 6674-6676 of SEQ ID NO:2.

Certain embodiments of the invention provide an expression cassette comprising:
 a) a nucleic acid comprising mTOR gene sequence NG_033239, or a portion thereof, wherein the nucleic acid has at least one mutation at a nucleotide position corresponding to 137,970, 137,971 and/or 137,972 of mTOR gene NG_033239;
 b) a nucleic acid comprising a mTOR cDNA nucleic acid sequence, or a portion thereof, wherein the nucleic acid comprises at least one mutation at a position corresponding to 6674, 6675 and/or 6676 of SEQ ID NO:2;
 c) a nucleic acid sequence having at least about 90% sequence identity to SEQ ID NO:2, wherein the nucleic acid has at least one mutation at position 6674, 6675 and/or 6676; or
 d) a nucleic acid encoding an mTOR protein, or portion thereof, comprising a mutation at an amino acid residue corresponding to 2185 of SEQ ID NO:1.

Certain embodiments of the invention provide a vector comprising an expression cassette described herein.

Certain embodiments of the invention provide a cell comprising an expression cassette described herein or vector described herein.

Certain embodiments of the invention provide a method for screening a test mTOR kinase inhibitor for anti-cancer activity, comprising:
 a) contacting a cancer cell with the test mTOR kinase inhibitor, wherein the cancer cell comprises a mTOR gene, or a portion thereof, which encodes a protein having a mutation at residue L2185; and
 b) detecting the growth rate of the cancer cell;
 wherein the cancer cell contacted with the test mTOR kinase inhibitor has a slower growth rate than a control cell indicates the test mTOR kinase inhibitor has anti-cancer activity.

BRIEF DESCRIPTION OF DRAWINGS

FIGS. 1A-E. Developing a yeast system to assay for mTOR kinase inhibition. (FIG. 1A) Wild type (WT) yeast cells were spread onto YPD plates and tested for sensitivity to structurally diverse mTOR kinase inhibitors by disc halo assay. Rapamycin was used as a positive control. (FIG. 1B) The N-terminus of TOR2 (1-2080 aa) was fused in frame with mTOR kinase domain (2140-2549 aa). The TOR2- mTOR fusion is expressed under the control of TOR2 promoter in a centromeric plasmid. (FIG. 1C) Yeast strain expressing WT TOR2 or TOR2-mTOR fusion was analyzed for expression by immunoblot with an antibody specific for mTOR kinase domain. PGK1 was used as a loading control and extracts from MCF7 breast cells were used as a positive control for mTOR. (FIG. 1D) TOR2-mTOR fusion was expressed in tort-dg and tested for its ability to complement TOR2 function by growth at permissive and restrictive temperatures. (FIG. 1E) tor2-dg cells expressing TOR2 or TOR2-mTOR were serially diluted by 10-fold and tested for drug sensitivity on plates containing BEZ235 and OSI-027.

FIGS. 2A-C. Enhancement of yeast cell permeability to structurally diverse mTOR kinase inhibitors by amphotericin B. (FIG. 2A) tor2-dg cells expressing TOR2-mTOR were spread on synthetic complete (SC)-leucine plate and tested for drug sensitivity by disc halo assay using filter discs containing different mTOR kinase inhibitors supplemented with the drug carrier DMSO or amphotericin B (10 μM). (FIG. 2B) Similar to FIG. 2A except the filter discs were supplemented with miconazole (50 μM). (FIG. 2C) Similar to FIG. 2A except the filter discs were supplemented with caspofungin (50 μM).

FIGS. 3A-E. Mutational analysis of the gatekeeper residue in mTOR kinase. (FIG. 3A) Sequence alignment of the gatekeeper site for PKA (SEQ ID NO: 4), c-Kit (SEQ ID NO: 9), EGFR (SEQ ID NO: 7), ABL (SEQ ID NO: 8), p110-PI3Kα (SEQ ID NO: 6) and mTOR (SEQ ID NO: 5). Arrowhead marks the gatekeeper residue. (FIG. 3B) Electrostatic model of the ATP-binding pocket of mTOR kinase (PDB ID code 4JSP). The 12237 position is as indicated. (FIG. 3C) tor2-dg cells expressing WT or mutant TOR2-mTOR were serially diluted by 10-fold and assayed for drug sensitivity on SC-leucine plates containing BEZ235, OSI-027, or Torin2, or AZD8055, BEZ235, INK128, PF-04691502 or PKI-587 in the presence of amphotericin B. (FIG. 3D) tor2-dg cells expressing WT or mutant TOR2-mTOR were serially diluted by 10-fold and assayed for cell growth at different temperatures. Vector and TOR2 plasmids were used as a negative and positive control, respectively. (FIG. 3E) Summary of gatekeeper mutations and their effects on mTOR kinase function. "+": normal function; "−": minor defect; "−−": moderate defect, and "−−−": severe defect.

FIGS. 4A-C. Identification of a hotspot for drug-resistant mutations in mTOR kinase domain. (FIG. 4A) Scheme of a yeast-based screen for drug-resistant mutations in mTOR kinase domain. mTOR kinase domain is amplified by error-prone PCR to generate randomized mutations, which is then recombined in frame into the TOR2-mTOR plasmid by gap-repair in tort-dg cells, and is selected on SC-leucine minus plates. Replica plating is then made onto SC-leucine plates containing DMSO or mTOR kinase inhibitor for selection of drug resistant clones. (FIG. 4B) tor2-dg cells expressing WT or mutant TOR2-mTOR were serially diluted by 10-fold and assayed for sensitivity to different mTOR kinase inhibitors in the presence of amphotericin B. Vector and TOR2 were used as controls. Drug resistant assay was performed at 37° C. in the presence of amphotericin B (except OSI-027). (FIG. 4C) Systematic mutational analysis of L2185 on drug resistance. tort-dg cells expressing WT or mutant TOR2-mTOR carrying all possible mutations at L2185 were serially diluted by 10-fold and tested for sensitivity to different mTOR kinase inhibitors at 37° C. AZD8055, BEZ235, INK128, PF-04691502 and PKI-587 were supplemented with amphotericin B.

FIGS. 5A-D. L2185A mutation confers resistance to mTOR kinase inhibitors in colorectal cancer models. (FIG. 5A) SW480 cells carrying homozygous WT mTOR or L2185A mutant alleles were treated with various concentrations of AZD8055, INK-128, OSI-027 and PP242 for 2 day. Growth of SW480 cells was measured by SRB assay. Data represent means±SD in three independent experiments. (FIG. 5B) SW480 cells carrying homozygous WT and L2185A mutant mTOR allele were treated with a single dose of AZD8055 (100 nM), INK-128 (100 nM), OSI-027 (6,000 nM), and PP242 (2,000 nM) for different times. Cell growth was measured by SRB assay. The drug carrier DMSO was used as a control. Data represent means±SD in three independent experiments. (FIG. 5C) SW480 cells carrying homozygous WT and L2185A mutant mTOR were treated with various concentrations of INK-128, OSI-027, AZD8055 and PP242 for 1 hr. The effect on the level of P-S6K, S6K, P-4E-BP1, 4EB-P1, P-AKT and AKT was analyzed by immunoblot. (FIG. 5D) SW480 cells carrying homozygous WT and L2185A mutant mTOR alleles were treated with various concentrations of BEZ235, PF-0691502 and Torin2 for 2 day. The growth of SW480 cells was measured by SRB assay. Data represent means±SD in three independent experiments.

FIGS. 6A-E. L2185A mutation renders resistance of xenograft tumors to mTOR kinase inhibitors. (FIG. 6A) Mice bearing xenograft tumors derived from SW480 cells expressing WT mTOR were administered with INK128 at 1 mg/kg or 0.3 mg/kg, once daily via intraperitoneal injection. Shown are representative animals and excised tumors after drug treatment. (FIG. 6B) Same as FIG. 6A except xenograft tumors were derived from SW480 carrying homozygous mTOR(L2185A) alleles. (FIG. 6C) Tumor volume measurement for SW480 xenograft tumors expressing mTOR (WT) (expressed as means±SD; n=8, *P<0.01, vs. vehicle control). (FIG. 6D) Tumor volume measurement for SW480 xenograft tumors expressing mTOR(L2185A) mutant (expressed as means±SD; n=8). (FIG. 6E) Tissue extracts from xenograft tumors at the end of treatment with or without 1 mg/kg INK128 were analyzed for the level of P-S6K, S6K, P-S6, S6, P-4E-BP1, 4E-BP1, P-AKT and AKT was analyzed by immunoblot. Six tumor samples from each animal group were shown with each lane representing an individual tumor sample.

FIGS. 7A-F. Saturation mutagenesis of highly conserved hydrophobic residues of mTOR kinase domain. (FIG. 7A) Shown is hydrophobic surface representation of the ATP-binding pocket of mTOR kinase bound with an ATP molecule (PDB ID code 4JSP). (FIG. 7B) Summary of the effect of mutations at different conserved hydrophobic residues in mTOR kinase domain. "+": normal; "−": minor defect; "−−": moderate defect; "−−−": severe defect. (FIG. 7C) Stacked bar graph summarizes each category of mutations in terms of function as a percentage of total mutations. (FIG. 7D) Stacked bar graph summarizing hydrophobic, neutral, and hydrophilic mutations as a percentage of total mutations with normal mTOR kinase function. (FIG. 7E) Shown is yeast growth-based assay for several representative mutations with severe loss-of-function in mTOR kinase. (FIG. 7F) WT and mutant Flag-mTOR were transiently expressed in HEK293T cells, immunoprecipitated, and assayed for mTOR kinase activity toward recombinant 4E-BP1 in vitro. Phosphorylation of 4E-BP1 was analyzed by immunoblot using a P-4E-BP1 specific antibody. Data represent means±SD in three independent experiments.

FIG. 9. Alignment of hydrophobic pocket sequences of PI3Ks and PIKKs. Figure discloses SEQ ID NOS 10-17, respectively, in order of appearance.

FIGS. 10A-G. L2185A mutation confers resistance to mTOR kinase inhibitors in lung cancer cells. (FIG. 10A) Flag-mTOR(L2185A), when transiently expressed in HEK293T cells, confers drug resistance to mTOR kinase inhibitors. HEK293T cells transiently expressing WT and L2185A mutant Flag-mTOR were treated with various concentrations of INK-128, OSI-027 for 1 hr. The effect on the level of P-S6K, S6K, P-4E-BP1, 4EB-P1, P-AKT and AKT was analyzed by immunoblot. (FIG. 10B) Sequencing verification of genome-engineered SW480 and H460 cells carrying homozygous and heterozygous L2185A mutations in mTOR locus. (FIG. 10C) Independent clones of engineered SW480 cells confer similar drug resistance. Cells were treated with various concentrations of AZD8055 and INK-128 for 2 days. Cell growth was measured by SRB assay. Clones #1, 3 carry heterozygous L2185A mutation. Clones #2, 4 carry homozygous L2185A mutation. Data represent means±SD in three independent experiments. (FIG. 10D) SW480 cells carrying heterozygous and homozygous mTOR(L2185A) mutant alleles have similar drug resistance to mTOR kinase inhibitors. SW480 cells carrying homozygous WT and L2185A mutant mTOR alleles were treated with various concentrations of AZD8055, INK-128, OSI-027, and PP242 for 2 days. Cell growth was measured by SRB assay. The drug carrier DMSO was used as a control. Data represent means±SD in three independent experiments. (FIG. 10E) H460 cells carrying homozygous WT and L2185A mutant mTOR alleles were treated with various concentrations of AZD8055, INK-128, OSI-027, and PP242 for 2 days. Cell growth was measured by SRB assay. The drug carrier DMSO was used as a control. Data represent means±SD in three independent experiments. (FIG. 10F) H460 cells carrying homozygous WT and L2185A mutant mTOR alleles were treated with various concentrations of OSI-027 for 1 hr. The effect on level of P-S6K, P-4E-BP1 and P-AKT was analyzed by immunoblot. (FIG. 10G) H460 cells carrying the WT and L2185A mutant mTOR allele were treated with various concentrations of BEZ235 for 2 days. The growth of H460 cells was measured by SRB assay. Data represent means±SD in three independent experiments.

FIGS. 11A-F. Structure analysis of mTOR L2185 residue in drug-binding pocket. (FIG. 11A) The location of L2185 and I2237 residue is shown within the structure of PP242-bound mTOR (PDB ID code 4JT5). Gatekeeper residue in the structure of imatinib-bound c-ABL kinase domain (PDB ID code 1IEP) is also shown for comparison. (FIG. 11B) Surface representation of the location of L2185 and modeled A2185 within the structures of ATP- and PP242-bound mTOR kinase domain (PDB ID codes 4JSP and 4JT5). (FIG. 11C) Comparing the drug-binding pocket of PP242-bound (PDB ID code 4JT5), Torin2-bound (PDB ID code 4JSX), ATP-bound (PDB ID code 4JSP) WT, and modeled L2185A mutant mTOR kinase domain. Measured and estimated distances between WT or L2185A mutant mTOR and PP242, Torin2 or ATP are shown. (FIG. 11D) Two hydrophobic spines of mTOR compared with PKA. Left panel, the hydrophobic residues the R-spine and the C-spine residues. Right panel shows only R- and C-spine residues. (FIG. 11E) Shown are separate views of the ATP-binding pockets of mTOR and PKA, and the location of key residues in R- and C-spines. (FIG. 11F) Shown are the salt bridge between K2187 and E2190 (mTOR), and K72 and E91 (PKA).

Figure 8:
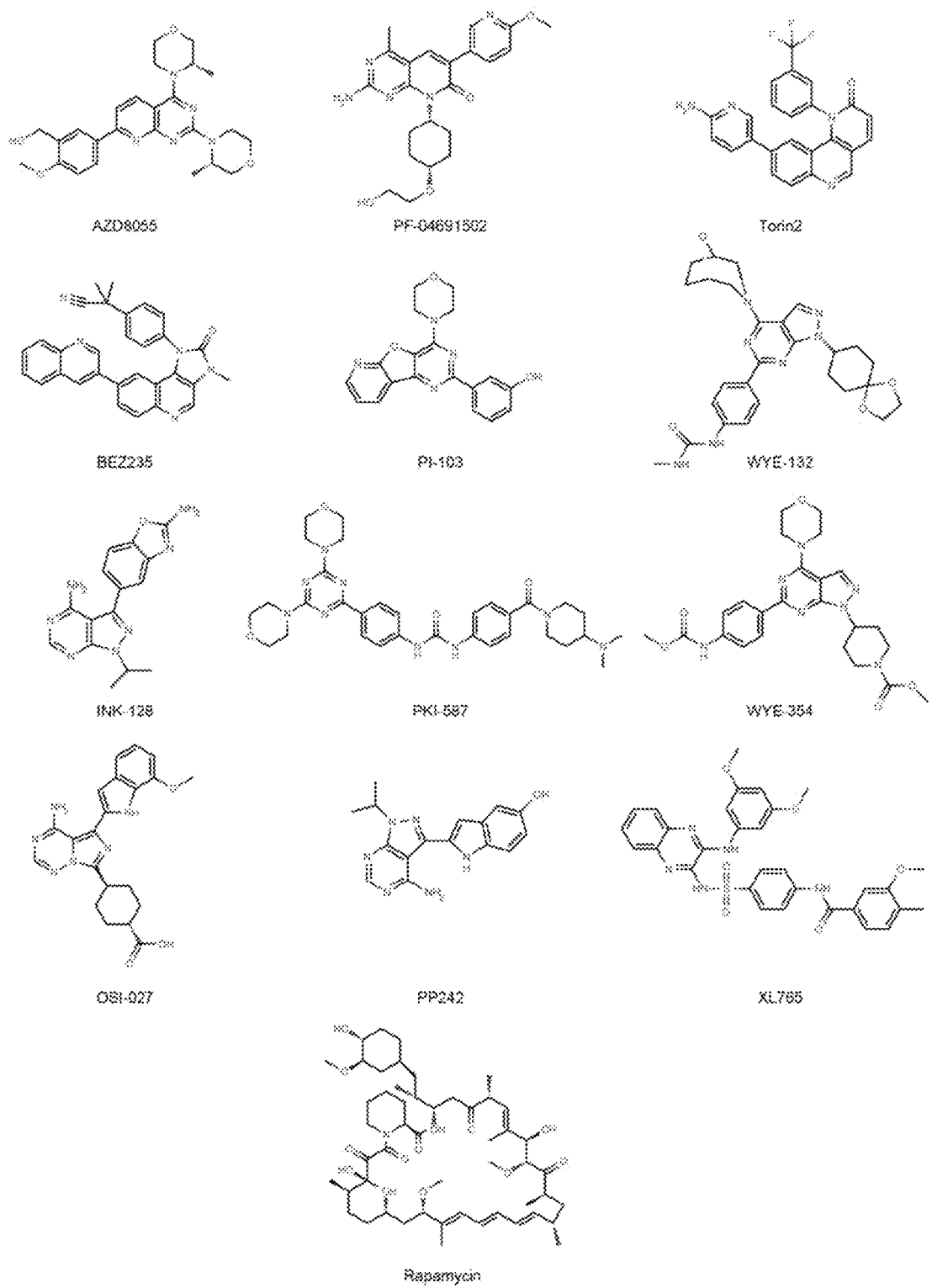
FIG. 8. Selected chemical structures of mTOR inhibitors.
Figure 12:
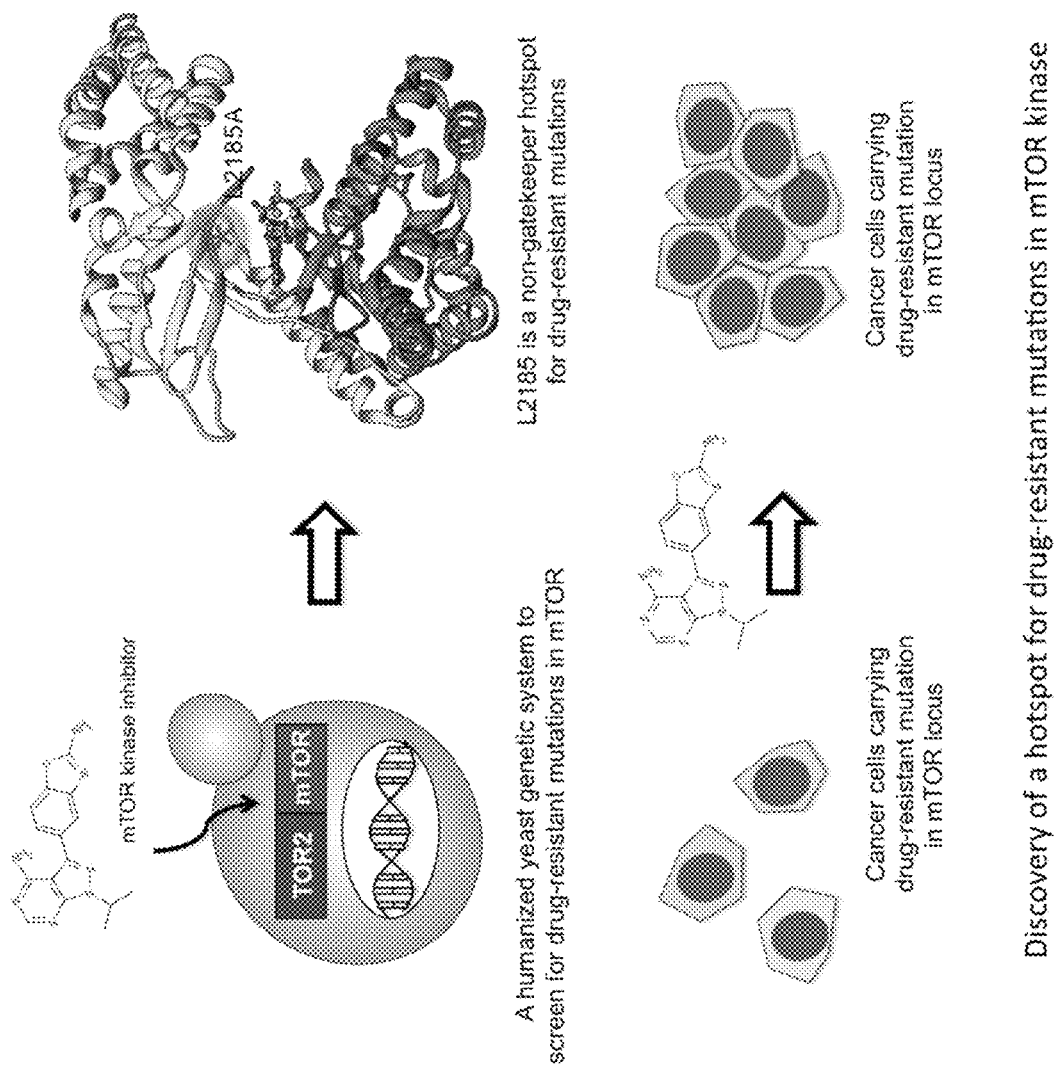
FIG. 12. Discovery of a hotspot for drug-resistant mutations in mTOR kinase.

DETAILED DESCRIPTION mTOR is a highly conserved kinase that forms two functional kinase complexes, mTORC1 and mTORC2. mTORC1 is a central controller of cell growth and metabolism, while mTORC2 positively regulates AKT, a survival kinase. Hyperactivation of mTOR pathway is a common theme for human cancers. Therefore, mTOR is an established cancer drug target with rapamycin analogs (rapalogs, e.g. Temsirolimus, Everolimus) already used in the clinic to treat various types of human cancers. However, the patients' response to rapalogs is modest due to the fact that they are only partial mTOR inhibitors, and cause feedback activation of AKT, which promotes cancer cell survival. The mTOR kinase domain is a more important site for cancer drug targeting, which is required for the function of both mTORC1 and mTORC2. This new concept led to the recent development of a large number of mTOR kinase inhibitors, with a significant number already in human cancer clinical trials, representing an important new class of anticancer agents. Based on clinical experience with targeted therapeutics, acquired resistance at the drug-binding site is thought to be highly likely, but not currently known. As described herein, a hotspot, L2185 for drug resistant mutations within mTOR kinase ATP-binding pocket has been identified. When L2185 of mTOR is mutated to 'A', 'C', 'N', or 'G', the mTOR kinase domain is resistant to certain mTOR kinase inhibitors. For example, when L2185 is mutated to 'A' at the genomic locus of breast, colorectal and lung cancer cells, mTOR kinase becomes resistant to a large number of mTOR kinase inhibitors, rendering drug-insensitive tumor growth. This hotspot may be used as a biomarker for, e.g., clinical diagnosis of acquired drug resistance to mTOR kinase inhibitors and discovery of new mTOR kinase inhibitors refractory to hotspot drug resistant mutations (e.g., structure-based design and in silico screen of chemical ligands to L2185 mTOR kinase mutants; and high throughput chemical screens of chemical inhibitors of L2185 mTOR kinase mutants). For example, as described herein two structurally related drugs were identified that are refractory to the L2185A mutations, revealing a tricyclic ring useful for designing second generation of mTOR kinase inhibitors to overcome drug resistant mutations.

Biomarkers for Drug Resistance and Methods of Use Thereof

Certain embodiments of the invention provide a method of detecting the presence of a biomarker associated with resistance to an mTOR kinase inhibitor in a subject, comprising determining the presence of the biomarker in a physiological sample from the subject, wherein the sample comprises a nucleic acid (e.g., DNA).

Certain embodiments of the invention provide a method for identifying resistance to an mTOR kinase inhibitor in a subject, comprising detecting the presence of a biomarker in a physiological sample from the subject, wherein the sample comprises a nucleic acid (e.g., DNA), and wherein the presence of the biomarker is indicative of resistance to an mTOR kinase inhibitor.

As used herein, the term "subject" is used to refer to mammal, such as a human. In certain embodiments the subject has cancer.

The term "biomarker" is generally defined herein as a biological indicator, such as a particular molecular feature, that may affect or be related to diagnosing or predicting resistance to an mTOR kinase inhibitor. For example, in certain embodiments of the present invention, the biomarker comprises a mutant mTOR gene, such as a GCT, GCC, GCA, GCG, TGT, TGC, GTT, GTC, GTA, GTG, GAT, GAC, AAT or AAC present at nucleotide positions 137,970-137,972 of mTOR gene NG_033239. These mutations result in an mTOR protein having an amino acid substitution at position 2185 (see, SEQ ID NO:1). Thus, in certain embodiments, the biomarker comprises at least one nucleotide base substitution in a mTOR polynucleotide (e.g., as compared to a wildtype sequence), wherein the at least one nucleotide base substitution results in an amino acid substitution at residue L2185 of the mTOR polypeptide. In certain embodiments, the biomarker comprises an amino acid substitution at residue L2185 of a mTOR polypeptide (e.g., as compared to a wildtype sequence; see, SEQ ID NO:1).

As used herein, the term "resistance to an mTOR kinase inhibitor" indicates that a cell, (e.g., a cancer cell) comprising the biomarker and exposed to the mTOR kinase inhibitor, would have a faster growth rate as compared to a control cell that did not comprise the biomarker. In certain embodiments, the growth rate of the cell is 10%, 20%, 30%, 40%, 50%, 60%, 70%, 80%, 90%, 95% or 100% faster than a control cell.

As used herein, the term "sensitivity to an mTOR kinase inhibitor" indicates that a cell, (e.g., a cancer cell) comprising the biomarker and exposed to the mTOR kinase inhibitor, would have a slower growth rate as compared to a control cell that did not comprise the biomarker. In certain embodiments, the growth rate of the cell is 10%, 20%, 30%, 40%, 50%, 60%, 70%, 80%, 90%, 95% or 100% slower than a control cell.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

In certain embodiments, the methods further comprise obtaining the physiological sample from the subject prior to detection. As used herein, the phrase "physiological sample" is meant to refer to a biological sample obtained from a subject that contains nucleic acid. The physiological sample obtained from the subject may also contain protein. Thus, as discussed herein, the biomarker may be detected at the nucleic acid or protein level. In certain embodiments, the physiological sample comprises a cancer cell(s) (e.g, colorectal cancer, lung cancer (e.g., non-small cell lung cancer) or breast cancer cell(s)).

Certain embodiments of the invention provide a method for identifying a cancer in a subject that is resistant to an mTOR kinase inhibitor, comprising:

a) obtaining a physiological sample comprising a cancer cell(s) from the subject; and $b_1$) detecting the presence of at least one mutation in a mTOR polynucleotide in the cancer cell(s), wherein the at least one mutation results in an amino acid substitution at residue L2185 of the mTOR polypeptide; or $b_2$) detecting the presence of a mutation at residue L2185 of a mTOR polypeptide in the cancer cell(s);

wherein the presence of the mutation is indicative of resistance to an mTOR kinase inhibitor.

In certain embodiments, the presence of at least one mutation in a mTOR polynucleotide in the cancer cell(s) is detected, wherein the at least one mutation results in an amino acid substitution at residue L2185 of the mTOR polypeptide.

In certain embodiments, the methods further comprise isolating or purifying the nucleic acid from the physiological sample prior to detection.

In certain embodiments, prior to or in conjunction with detection, the nucleic acid is subject to an amplification step. For example, in certain embodiments, the sample is contacted with at least one oligonucleotide probe to form a hybridized nucleic acid and the hybridized nucleic acid is amplified.

"Oligonucleotide probe" can refer to a nucleic acid segment that is complementary to, and hybridizes specifically to, a particular sequence in mTOR, or to a nucleic acid region that flanks mTOR. For example, in certain embodiments, the probe is a primer that may be useful to amplify a sequence in the mTOR gene, and that is complementary to, and hybridizes specifically to, a particular sequence in mTOR, or to a nucleic acid region that flanks mTOR. In another embodiment, the probe comprises a detection means and may be used to detect a biomarker.

In certain embodiments, the amplification of the hybridized nucleic acid is carried out by polymerase chain reaction, strand displacement amplification, ligase chain reaction, or nucleic acid sequence-based amplification. Reagents and hardware for conducting PCR are commercially available. For example, in certain embodiments of the present invention, the mTOR gene, or a portion thereof, may be amplified by PCR.

In certain embodiments, the mTOR gene or a portion thereof is amplified (e.g., exon 47 is amplified) (see, e.g., mTOR genomic DNA Accession No. NG_033239, which is incorporated by reference herein).

In certain embodiments, the detecting step is by a) allele specific hybridization; b) size analysis; c) sequencing; d) hybridization; e) 5' nuclease digestion; f) single-stranded conformation polymorphism; g) primer specific extension; and/or h) oligonucleotide ligation assay.

In certain embodiments, the size analysis is preceded by a restriction enzyme digestion.

In certain embodiments, an oligonucleotide probe specific for the biomarker is used in the detection step. For example, in certain embodiments, the nucleic acid or the amplified nucleic acid is contacted with at least one oligonucleotide probe to form a hybridized nucleic acid. In certain embodiments, at least one oligonucleotide probe specific for the biomarker is immobilized on a solid surface. In certain embodiments, the oligonucleotide probe comprises at least one synthetic nucleotide. In certain embodiments, the oligonucleotide probe comprises a detection means (e.g., a fluorescent label).

In certain embodiments, the biomarker comprises a mutation(s) at nucleotide positions 137,970, 137,971 and/or 137,972 of mTOR gene NG_033239. In certain embodiments, the mutation(s) is selected from GCT, GCC, GCA, GCG, TGT, TGC, GTT, GTC, GTA, GTG, GAT, GAC, AAT, AAC present at nucleotide positions 137,970-137,972 of mTOR gene NG_033239.

In certain embodiments, the biomarker comprises a nucleic acid that encodes a mTOR protein having a mutation at amino acid residue 2185 of SEQ ID NO:1. In certain embodiments, the mutation is selected from L2185A, L2185C, L2185D, L2185N and L2185G. In certain embodiments, the mutation is L2185A. In certain embodiments, the mutation is L2185C.

In certain embodiments, the presence of a mutation at residue L2185 of a mTOR polypeptide in the cancer cell(s) is detected. In certain embodiments, the mutation is selected from L2185A, L2185C, L2185D, L2185N and L2185G. In certain embodiments, the mutation is L2185A. In certain embodiments, the mutation is L2185C.

In certain embodiments, the methods further comprise isolating or purifying protein from the physiological sample prior to detection.

In certain embodiments, the detecting step comprises the use of an antibody, Western blot, an immunohistochemical assay and/or an ELISA assay.

In certain embodiments, the subject (e.g., a human) has cancer. In certain embodiments, the cancer is selected from colorectal cancer, lung cancer (e.g., non-small cell lung cancer), breast cancer or another cancer type.

Certain embodiments of the invention provide a method for detecting the presence of a biomarker in a subject, comprising determining the presence of the biomarker in a physiological sample from the subject, wherein the sample comprises a nucleic acid, and wherein the biomarker comprises a nucleic acid that encodes a mTOR protein having a mutation at amino acid residue 2185 of SEQ ID NO:1. In certain embodiments, the mutation is selected from L2185A, L2185C, L2185D, L2185N and L2185G. In certain embodiments, the mutation is L2185A. In certain embodiments, the mutation is L2185C.

Certain embodiments of the invention provide a method of detecting the presence of a biomarker associated with resistance to an mTOR kinase inhibitor in a subject, comprising:
 a) obtaining a physiological sample from the subject, wherein the sample comprises a nucleic acid;
 b) amplifying the nucleic acid from the sample; and
 c) detecting the presence of the biomarker;
wherein the presence of the biomarker is indicative of resistance to an mTOR kinase inhibitor.

Certain embodiments of the invention provide a method for identifying resistance to an mTOR kinase inhibitor in a subject, comprising:
 a) obtaining a physiological sample from the subject, wherein the sample comprises a nucleic acid;
 b) amplifying the nucleic acid from the sample; and
 c) detecting the presence of a biomarker;
wherein the presence of the biomarker is indicative of resistance to an mTOR kinase inhibitor.

In certain embodiments, the presence of the biomarker indicates resistance to an mTOR kinase inhibitor including, but not limited to, OSI-027, AZD8055, INK128, PF-04691502, PKI-587 and derivatives thereof.

Certain embodiments of the invention provide a method for detecting resistance to an mTOR kinase inhibitor in a subject comprising identifying in a nucleic acid sample from the subject a nucleic acid encoding an mTOR protein comprising a mutation at amino acid residue 2185 of SEQ ID NO:1, wherein a L2185A, L2185C, L2185D, L2185N or L2185G is indicative of resistance to an mTOR kinase inhibitor.

Methods of Treating

Certain embodiments of the invention provide a method of treating cancer in a subject (e.g., a human) comprising:
 a) detecting the presence or absence of a biomarker in a physiological sample from the subject, wherein the sample comprises a nucleic acid (e.g., DNA);
 b) selecting a mTOR kinase inhibitor for administration to the subject based on the presence or absence of the biomarker; and
 c) administering an effective amount of the selected mTOR kinase inhibitor to the subject to treat the cancer.

Certain embodiments of the invention provide a method of treating cancer in subject comprising:
 a) detecting the presence or absence of a biomarker in a physiological sample obtained from the subject, wherein the sample comprises a cancer cell(s), and wherein the biomarker comprises 1) at least one mutation in a mTOR polynucleotide that results in an amino acid substitution at residue L2185 of the mTOR polypeptide; or 2) a mutation at residue L2185 of a mTOR polypeptide;
 b) selecting an mTOR kinase inhibitor for administration to the subject based on the presence or absence of the biomarker; and
 c) administering an effective amount of the selected mTOR kinase inhibitor to the subject to treat the cancer.

Certain embodiments of the invention provide a method of treating cancer in a subject comprising administering an effective amount of a mTOR kinase inhibitor to the subject, wherein the cancer was determined to comprise 1) at least one mutation in a mTOR polynucleotide that results in an amino acid substitution at residue L2185 of a mTOR polypeptide; or 2) a mutation at residue L2185 of a mTOR polypeptide.

The term "treatment" or "treating," to the extent it relates to cancer includes inhibiting cancer and/or eliminating cancer and/or relieving one or more symptoms of cancer. The term "preventing" or 'prevention" includes preventing cancer from occurring or lessening the severity of the cancer.

In certain embodiments, the presence of the biomarker is indicative of resistance to certain mTOR kinase inhibitors. For example, the presence of the biomarker indicates that the cancer is resistant to certain mTOR kinase inhibitors (e.g., OSI-027, AZD8055, INK128, PF-04691502, and PKI-587) and sensitive to other mTOR kinase inhibitors (e.g., inhibitors with a three-ring fused heterocyclic structure, such as BEZ235 and Torin2). Thus, in certain embodiments, if the presence of the biomarker is detected, an mTOR kinase inhibitor having a three-ring fused heterocyclic structure (e.g., BEZ235, Torin2, or derivatives thereof) is selected for administration to the subject. In certain other embodiments, if the absence of the biomarker is detected, an mTOR kinase inhibitor with or without a three-ring fused heterocyclic structure (e.g., OSI-027, AZD8055, INK128, PF-04691502, PKI-587, BEZ235, Torin2, or derivatives thereof) is selected for administration to the subject. In certain other embodiments, if the absence of the biomarker is detected, an mTOR kinase inhibitor without a three-ring fused heterocyclic structure (e.g., OSI-027, AZD8055, INK128, PF-04691502, PKI-587 or derivatives thereof) is selected for administration to the subject.

Certain embodiments of the invention provide an mTOR kinase inhibitor with a three-ring fused heterocyclic structure (e.g., BEZ235, Torin2, or derivatives thereof) for use in treating cancer in a subject having a biomarker described herein (e.g., a nucleic acid encoding protein with a mutation at amino acid residue 2185 of SEQ ID NO:1).

Certain embodiments of the invention provide an mTOR kinase inhibitor with a three-ring fused heterocyclic structure (e.g., BEZ235, Torin2, or derivatives thereof) for use in treating cancer in a subject, comprising assaying a physiological sample from a subject, determining if the subject has a biomarker described herein (e.g., a nucleic acid encoding a protein with a mutation at amino acid residue 2185 of SEQ ID NO:1), and administering a therapeutically effective amount of the mTOR kinase inhibitor with a three-ring fused heterocyclic structure to the subject if the biomarker is present.

In certain embodiments, the physiological sample is obtained from the subject prior to detection. In certain embodiments, the physiological sample comprises a cancer cell(s) (e.g, colorectal cancer, lung cancer (e.g., non-small cell lung cancer) or breast cancer cell(s)).

In certain embodiments, the nucleic acid is isolated from the physiological sample prior to detection.

In certain embodiments, prior to or in conjunction with detection, the nucleic acid is subject to an amplification step. In certain embodiments, the mTOR gene or a portion thereof is amplified (e.g., the kinase domain or a portion thereof is amplified).

In certain embodiments, the detecting step is by a) allele specific hybridization; b) size analysis; c) sequencing; d) hybridization; e) 5' nuclease digestion; f) single-stranded conformation polymorphism; g) primer specific extension; and/or h) oligonucleotide ligation assay.

In certain embodiments, the detecting step comprises the use of an antibody, Western blot, an immunohistochemical assay and/or an ELISA assay.

In certain embodiments, the biomarker comprises a mutation(s) at nucleotide positions 137,970, 137,971 and/or 137,972 of mTOR gene NG_033239. In certain embodiments, the mutation(s) is selected from GCT, GCC, GCA, GCG, TGT, TGC, GTT, GTC, GTA, GTG, GAT, GAC, AAT and AAC present at nucleotide positions 137,970-137,972 of mTOR gene NG_033239.

In certain embodiments, the biomarker comprises a nucleic acid that encodes an mTOR protein having a mutation at amino acid residue 2185 of SEQ ID NO:1. In certain embodiments, the mutation is selected from L2185A, L2185C, L2185D, L2185N and L2185G. In certain embodiments, the mutation is L2185A. In certain embodiments, the mutation is L2185C.

In certain embodiments, the cancer is selected from colorectal, lung and breast cancer.

An mTOR kinase inhibitor may be formulated as a pharmaceutical composition and administered to a mammalian host, such as a human patient in a variety of forms adapted to the chosen route of administration, i.e., orally, rectally or parenterally, by intravenous, intramuscular, topical, intranasally or subcutaneous routes.

Thus, the inhibitors may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the inhibitors may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the present compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the inhibitors can be determined by comparing their in vitro activity, and in vivo activity in animal models. Methods for the extrapolation of effective dosages in mice, and other animals, to humans are known to the art; for example, see U.S. Pat. No. 4,938,949.

The amount of an inhibitor required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Kits

In another aspect, the invention features kits for performing the above-described assays. The kit can include DNA sample collection means and a means for detecting a mutation that is indicative of resistance to a mTOR kinase domain inhibitor in a subject. In one embodiment, the kit contains a first primer oligonucleotide that hybridizes 5' or 3' to a mutation(s) at position 137,970, 137,971 and/or 137,972 of mTOR gene NG_033239. In certain embodiments, the mutation(s) is selected from GCT, GCC, GCA, GCG, TGT, TGC, GTT, GTC, GTA, GTG, GAT, GAC, AAT and AAC present at nucleotide positions 137,970-137,972 of mTOR gene NG_033239. In one embodiment, the kit additionally comprises a second primer oligonucleotide that hybridizes either 3' or 5' respectively to the mutation, so that the mutation can be amplified. In one embodiment, first primer and the second primer hybridize to a region in the range of between about 50 and about 1000 base pairs. In one embodiment, the kit additionally comprises a detection means. In certain embodiments, the detection means is by a) allele specific hybridization; b) size analysis; c) sequencing; d) hybridization; e) 5' nuclease digestion; f) single-stranded conformation polymorphism; g) primer specific extension; and/or h) oligonucleotide ligation assay. In certain embodiments, the kit additionally comprises an amplification means. In certain embodiments, the kit additionally comprises packaging material. In certain embodiments, the kit additionally comprises instructions for use.

Certain embodiments of the invention provide a kit for identifying a cancer in a subject that is resistant to an mTOR kinase inhibitor, the kit comprising:

a) a first primer oligonucleotide that hybridizes 5' or 3' to at least one mutation located at nucleotide positions corresponding to 137,970, 137,971 and/or 137,972 of mTOR gene NG_033239; and/or b) an allele specific oligonucleotide that is specific for a mutation that results in an amino acid substitution at residue L2185 of a mTOR polypeptide;

wherein the first primer oligonucleotide and/or the allele specific oligonucleotide comprises a detection means (e.g., a fluorescent or radioactive label).

Information obtained using the assays and kits described herein is useful for determining whether a subject has cancer that is resistant to certain mTOR kinase domain inhibitors. In addition, the information allows customization of therapy to the subject's genetic profile.

Compositions

Isolated or Purified Nucleic Acids and Proteins

Certain embodiments of the invention provide an isolated or purified nucleic acid (e.g., RNA or DNA) comprising mTOR gene sequence NG_033239, or a portion thereof, wherein the nucleic acid has a mutation(s) at a nucleotide position 137,970, 137,971 and/or 137,972. In certain embodiments, the mutation(s) is selected from GCT, GCC, GCA, GCG, TGT, TGC, GTT, GTC, GTA, GTG, GAT, GAC, AAT and AAC present at nucleotide positions 137,970-137,972. In certain embodiments, the nucleic acid sequence has at least about 70%, 75%, 80%, 85%, 90%, 95%, 96%, 97%, 98%, 99%, 99.9% sequence identity to mTOR gene sequence NG_033239. In certain embodiments, the isolated or purified nucleic acid comprises the full length mTOR sequence. In certain embodiments, the isolated or purified nucleic acid sequence comprises only a portion of the mTOR sequence. In certain embodiments, the isolated or purified nucleic acid sequence is about 20, 50, 100, 150, 200, 300, 400, 500, 1,000, 5,000, 10,000, 50,000, 100,000, 150, 000 nucleotides or more in length. In certain embodiments, the isolated or purified nucleic acid is between about 20 nucleotides to about 156,021 nucleotides in length. In certain embodiments, the isolated or purified nucleic acid is between about 20 nucleotides to about 100,000 nucleotides in length. In certain embodiments, the isolated or purified nucleic acid is between about 20 nucleotides to about 50,000 nucleotides in length. In certain embodiments, the isolated or purified nucleic acid is between about 20 nucleotides to about 10,000 nucleotides in length. In certain embodiments, the isolated or purified nucleic acid is between about 20 nucleotides to about 1,000 nucleotides in length. In certain embodiments, the isolated or purified nucleic acid is between about 20 nucleotides to about 500 nucleotides in length.

Certain embodiments of the invention provide an isolated or purified nucleic acid comprising a mTOR cDNA nucleic acid sequence, or a portion thereof, wherein the nucleic acid comprises at least one mutation at a position corresponding to 6674, 6675 and/or 6676 of SEQ ID NO:2. Certain embodiments of the invention provide an isolated or purified nucleic acid sequence comprising SEQ ID NO:2, or a portion thereof, wherein the nucleic acid has a mutation(s) at a nucleic acid position 6674, 6675 and/or 6676. In certain embodiments, the mutation(s) is selected from GCT, GCC, GCA, GCG, TGT, TGC, GTT, GTC, GTA, GTG, GAT, GAC, AAT and AAC present at nucleotide positions 6674-6676. In certain embodiments, the nucleic acid has at least about 70%, 75%, 80%, 85%, 90%, 95%, 96%, 97%, 98%, 99%, 99.9% sequence identity to SEQ ID NO:2. In certain embodiments, the isolated or purified nucleic acid comprises the full length mTOR cDNA sequence. In certain embodiments, the isolated or purified nucleic acid sequence comprises only a portion of the mTOR cDNA sequence. In certain embodiments, the isolated or purified nucleic acid sequence is about 20, 50, 100, 150, 200, 300, 400, 500, 1,000, 2,000, 3,000, 4,000, 5,000, 6,000, 7,000, 8,000 nucleotides or more in length. In certain embodiments, the isolated or purified nucleic acid is between about 20 nucleotides to about 10,000 nucleotides in length. In certain embodiments, the isolated or purified nucleic acid is between about 20 nucleotides to about 8,733 nucleotides in length. In certain embodiments, the isolated or purified nucleic acid is between about 20 nucleotides to about 5,000 nucleotides in length. In certain embodiments, the isolated or purified nucleic acid is between about 20 nucleotides to about 1,000 nucleotides in length. In certain embodiments, the isolated or purified nucleic acid is between about 20 nucleotides to about 500 nucleotides in length.

Certain embodiments of the invention provide an isolated or purified nucleic acid (e.g., DNA or RNA) encoding an mTOR protein, or portion thereof (e.g., the mTOR kinase domain), having a mutation at amino acid residue 2185 of SEQ ID NO:1.

Certain embodiments of the invention provide an isolated or purified mTOR protein, or portion thereof (e.g., the mTOR kinase domain), having a mutation at amino acid residue 2185 of SEQ ID NO:1. In certain embodiments, the isolated or purified protein comprises the full length mTOR protein sequence. In certain embodiments, the isolated or purified protein sequence comprises only a portion of the mTOR protein sequence. In certain embodiments, the isolated or purified protein sequence is about 20, 50, 100, 150, 200, 300, 400, 500, 1,000, 2,000, 2,500 amino acids or more in length. In certain embodiments, the isolated or purified protein is between about 20 amino acids to about 2,549 amino acids in length. In certain embodiments, the isolated or purified protein is between about 20 amino acids to about 2,000 amino acids in length. In certain embodiments, the isolated or purified protein is between about 20 amino acids to about 1,000 amino acids in length. In certain embodiments, the isolated or purified protein is between about 20 amino acids to about 500 amino acids in length. In certain embodiments, the isolated or purified protein is between about 20 amino acids to about 200 amino acids in length. In certain embodiments, the isolated or purified protein is between about 20 amino acids to about 100 amino acids in length.

Certain embodiments of the invention provide an isolated or purified amino acid, comprising an amino acid sequence having at least about 70%, 75%, 80%, 85%, 90%, 95%, 96%, 97%, 98%, 99%, 99.9% sequence identity to SEQ ID NO:1, wherein the amino acid sequence comprises a mutation at an amino acid residue 2185 of SEQ ID NO:1.

In certain embodiments, the mutation is selected from L2185A, L2185C, L2185D, L2185N and L2185G. In certain embodiments, the mutation is L2185A. In certain embodiments, the mutation is L2185C.

Expression Cassettes, Vectors and Host Cells

Certain embodiments of the invention provide an expression cassette comprising a nucleic acid described herein.

Certain embodiments of the invention provide an expression cassette comprising a nucleic acid encoding an mTOR protein, or a portion thereof (e.g., the kinase domain), wherein the mTOR protein or portion thereof comprises a mutation at amino acid residue 2185 of SEQ ID NO:1. In certain embodiments, the mutation is selected from L2185A, L2185C, L2185D, L2185N and L2185G. In certain embodiments, the mutation is L2185A. In certain embodiments, the mutation is L2185C.

Certain embodiments of the invention provide an expression cassette comprising:

a) a nucleic acid comprising mTOR gene sequence NG_033239, or a portion thereof, wherein the nucleic acid has at least one mutation at a nucleotide position corresponding to 137,970, 137,971 and/or 137,972;

b) a nucleic acid sequence having at least about 90% sequence identity to SEQ ID NO:2, wherein the nucleic acid has at least one mutation at position 6674, 6675 and/or 6676; or c) nucleic acid encoding an mTOR protein, or portion thereof, comprising a mutation at an amino acid residue corresponding to 2185 of SEQ ID NO:1.

In certain embodiments, the expression cassette further comprises a promoter (e.g., a regulatable or constitutive promoter).

Certain embodiments of the invention provide a vector comprising an expression cassette described herein.

Certain embodiments of the invention provide a cell comprising an expression cassette or vector described herein.

Certain embodiments of the invention provide a transgenic host cell comprising a nucleic acid encoding an mTOR protein, or portion thereof (e.g., the kinase domain), wherein the mTOR protein or portion thereof has a mutation at amino acid residue 2185 (e.g., L2185A, L2185C, L2185D, L2185N or L2185G) of SEQ ID NO:1.

Certain embodiments of the invention provide a transgenic host cell that expresses an mTOR protein, or portion thereof (e.g., the kinase domain), having a mutation at amino acid residue 2185 (e.g., L2185A, L2185C, L2185D, L2185N or L2185G) of SEQ ID NO:1.

Oligonucleotide Probes

As discussed above, an "oligonucleotide probe" refers to a nucleic acid segment that is complementary to, and hybridizes specifically to, a particular sequence in mTOR, or to a nucleic acid region that flanks mTOR. For example, in certain embodiments, the probe is a primer that may be useful to amplify a sequence in the mTOR gene, and that is complementary to, and hybridizes specifically to, a particular sequence in mTOR, or to a nucleic acid region that flanks mTOR. In another embodiment, the probe is complementary to, and hybridizes specifically to, a particular sequence in mTOR and comprises a detection means, which may be used to detect a biomarker.

Accordingly, the nucleotide segments of the invention may be used for their ability to selectively form duplex molecules with complementary stretches of the mTOR gene, RNA or cDNA or to provide primers for amplification of DNA/RNA/cDNA or flanking region or to provide probes for biomarker detection. The design of appropriate probes for this purpose requires consideration of a number of factors. For example, fragments having a length of between 10, 15, or 18 nucleotides to about 20, or to about 30 nucleotides, will find particular utility. Longer sequences, e.g., 40, 50, 80, 90, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe. Furthermore, depending on the application envisioned, one will desire to employ varying conditions of hybridization to achieve varying degrees of selectivity of probe towards target sequence. For applications requiring high selectivity, one will typically desire to employ relatively stringent conditions to form the hybrids. For example, relatively low salt and/or high temperature conditions, such as provided by 0.02 M-0.15M NaCl at temperatures of about 50° C. to about 70° C. Such selective conditions may tolerate little, if any, mismatch between the probe and the template or target strand.

Primer pairs are useful for determination of the nucleotide sequence of mTOR in a particular sample. The pairs of single-stranded DNA primers can be annealed to sequences within or surrounding the mTOR gene in order to prime amplifying DNA synthesis of a specific region of mTOR gene itself (e.g., exon 47). Allele-specific primers can also be used. Such primers anneal only to particular mTOR mutant alleles, and thus will only amplify a product in the presence of the mutant allele as a template.

The first step of the process involves contacting a physiological sample obtained from a subject, which sample contains nucleic acid, with an oligonucleotide probe to form a hybridized DNA. In certain embodiments, oligonucleotide probes that are useful in the methods of the present invention can be any probe comprised of between about 4 or 6 bases up to about 80 or 100 bases, or 100 bases to 500 bases or more. In one embodiment of the present invention, the probes are between about 10 and about 20 bases. In one embodiment, the oligonucleotide probe comprises a detection means (e.g., a fluorescent label).

The primers themselves can be synthesized using techniques that are well known in the art. Generally, the primers can be made using oligonucleotide synthesizing machines that are commercially available. Given the sequence of the mTOR coding sequence as set forth in SEQ ID NO:2, as well as the genomic DNA sequence (NG_033239), design of particular primers is well within the skill of the art.

Oligonucleotide probes may be prepared having any of a wide variety of base sequences according to techniques that are well known in the art. Suitable bases for preparing the oligonucleotide probe may be selected from naturally occurring nucleotide bases such as adenine, cytosine, guanine, uracil, and thymine; and non-naturally occurring or "synthetic" nucleotide bases such as 7-deaza-guanine 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O-methylpseudouridine, β,D-galactosylqueosine, 2'-O-methylguanosine, inosine, N6-isopentenyladenosine, 1-methyladenosine, 1-methylpseeudouridine, 1-methylguanosine, 1-methylinosine, 2,2-dimethylguanosine, 2-methyladenosine, 2-methyl guanosine, 3-methylcytidine, 5-methylcytidine, N6-methyladenosine, 7-methylguanosine, 5-methylamninomethyluridine, 5-methoxyaminomethyl-2-thiouridine, β,D-mannosylqueosine, 5-methloxycarbonylmethyluridine, 5-methoxyuridine, 2-methyltio-N6-isopentenyladenosine, N-((9-β-D-ribofuranosyl-2-methylthiopurine-6-yl)carbamoyl)threonine, N-((9-β-D-ribofuranosylpurine-6-yl)N-methyl-carbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-Methylurdine, N-((9-beta-D-ribofuranosylpurine-6-yl)carbamoyl)threonine, 2'-O-methyl-5-methyluridine, 2'-O-methyluridine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonotlioates, phosphoroinorpholidates, phosphoropiperazidates and phosplioramidates (for example, every other one of the internucleotide bridging phosphate residues may be modified as described). The oligonucleotide may be a "peptide nucleic acid" such as described in Nielsen et al., Science, 254, 1497-1500 (1991).

The only requirement is that the oligonucleotide probe should possess a sequence at least a portion of which is capable of binding to a known portion of the sequence of the DNA sample.

It may be desirable in some applications to contact the DNA sample with a number of oligonucleotide probes having different base sequences (e.g., where there are two or more target nucleic acids in the sample, or where a single target nucleic acid is hybridized to two or more probes in a "sandwich" assay).

The nucleic acid probes provided by the present invention are useful for a number of purposes. The probes can be used to detect PCR amplification products. They may also be used to detect mismatches with the mTOR gene or mRNA using other techniques.

In certain embodiments, at least one oligonucleotide probe specific for the biomarker is immobilized on a solid surface. In certain embodiments, the oligonucleotide probe further comprises a detection means (e.g., a fluorescent label).

Methods of Screening mTOR Kinase Inhibitors

Certain embodiments of the invention provide a method for screening a potential mTOR kinase inhibitor, comprising:

a) growing a transgenic host cell comprising a mTOR gene, or a portion thereof, that encodes a protein having a mutation at amino acid residue 2185 (e.g., L2185A, L2185C, L2185D, L2185N or L2185G) of SEQ ID NO:1 in the presence and absence of a potential mTOR kinase inhibitor;

b) determining growth rates of the transgenic cells grown in the presence and absence of the potential mTOR kinase inhibitor; and
c) comparing the growth rates of the transgenic cells grown in the presence and absence of the potential mTOR kinase inhibitor;

wherein a slower growth rate of transgenic cells grown in the presence of the potential mTOR kinase inhibitor is indicative of a mTOR kinase inhibitor.

Certain embodiments of the invention provide a method for screening a test mTOR kinase inhibitor for anti-cancer activity, comprising:
a) contacting a cancer cell with the test mTOR kinase inhibitor, wherein the cancer cell comprises a mTOR gene, or a portion thereof, which encodes a protein having mutation at residue L2185; and
b) detecting the growth rate of the cancer cell;

wherein the cancer cell contacted with the test mTOR kinase inhibitor has a slower growth rate than a control cell indicates the test mTOR kinase inhibitor has anti-cancer activity. In certain embodiments, the cancer cell is a transgenic cell. In certain embodiments, the cancer cell is a transgenic cell comprising an expression cassette or vector described herein.

Certain mTOR Sequences

As described herein, mutations at amino acid position 2185 of the human mTOR protein have been shown cause resistance to certain kinase domain inhibitors (see, SEQ ID NO:1 below; position 2185 is highlighted). Equivalent residues are present in corresponding mTOR proteins derived from other mammals. While the amino acid residues described herein are numbered in reference to the human form of mTOR; one skilled in the art may readily determine equivalent residues in a different mammal using known techniques and algorithms (e.g., BLAST, ALIGN or ExPASy).

mTOR Protein Sequence (SEQ ID NO: 1)
MLGTGPAAATTAATTSSNVSVLQQFASGLKSRNEETRAKAAKELQHYVT

MELREMSQEESTRFYDQLNHHIFELVSSSDANERKGGILAIASLIGVEG

GNATRIGRFANYLRNLLPSNDPVVMEMASKAIGRLAMAGDTFTAEYVEF

EVKRALEWLGADRNEGRRHAAVLVLRELAISVPTFFFQQVQPFFDNIFV

AVWDPKQAIREGAVAALRACLILTTQREPKEMQKPQWYRHTFEEAEKGF

DETLAKEKGMNRDDRIHGALLILNELVRISSMEGERLREEMEEITQQQL

VHDKYCKDLMGFGTKPRHITPFTSFQAVQPQQSNALVGLLGYSSHQGLM

GFGTSPSPAKSTLVESRCCRDLMEEKFDQVCQWVLKCRNSKNSLIQMTI

LNLLPRLAAFRPSAFTDTQYLQDTMNHVLSCVKKEKERTAAFQALGLLS

VAVRSEFKVYLPRVLDIIRAALPPKDFAHKRQKAMQVDATVFTCISMLA

RAMGPGIQQDIKELLEPMLAVGLSPALTAVLYDLSRQIPQLKKDIQDGL

LKMLSLVLMHKPLRHPGMPKGLAHQLASPGLTTLPEASDVGSITLALRT

LGSFEFEGHSLTQFVRHCADHFLNSEHKEIRMEAARTCSRLLTPSIHLI

SGHAHVVSQTAVQVVADVLSKLLVVGITDPDPDIRYCVLASLDERFDAH

LAQAENLQALFVALNDQVFEIRELAICTVGRLSSMNPAFVMPFLRKMLI

QILTELEHSGIGRIKEQSARMLGHLVSNAPRLIRPYMEPILKALILKLK

DPDPDPNPGVINNVLATIGELAQVSGLEMRKWVDELFIIIMDMLQDSSL

LAKRQVALWTLGQLVASTGYVVEPYRKYPTLLEVLLNFLKTEQNQGTRR

EAIRVLGLLGALDPYKHKVNIGMIDQSRDASAVSLSESKSSQDSSDYST

SEMLVNMGNLPLDEFYPAVSMVALMRIFRDQSLSHHHTMVVQAITFIFK

SLGLKCVQFLPQVMPTFLNVIRVCDGAIREFLFQQLGMLVSFVKSHIRP

YMDEIVTLMREFWVMNTSIQSTIILLIEQIVVALGGEFKLYLPQLIPHM

LRVFMHDNSPGRIVSIKLLAAIQLFGANLDDYLHLLLPPIVKLFDAPEA

PLPSRKAALETVDRLTESLDFTDYASRIIHPIVRTLDQSPELRSTAMDT

LSSLVFQLGKKYQIFIPMVNKVLVRHRINHQRYDVLICRIVKGYTLADE

EEDPLIYQHRMLRSGQGDALASGPVETGPMKKLHVSTINLQKAWGAARR

VSKDDWLEWLRRLSLELLKDSSSPSLRSCWALAQAYNPMARDLFNAAFV

SCWSELNEDQQDELIRSIELALTSQDIAEVTQTLLNLAEFMEHSDKGPL

PLRDDNGIVLLGERAAKCRAYAKALHYKELEFQKGPTPAILESLISINN

KLQQPEAAAGVLEYAMKHFGELEIQATWYEKLHEWEDALVAYDKKMDTN

KDDPELMLGRMRCLEALGEWGQLHQQCCEKWTLVNDETQAKMARMAAAA

AWGLGQWDSMEEYTCMIPRDTHDGAFYRAVLALHQDLFSLAQQCIDKAR

DLLDAELTAMAGESYSRAYGAMVSCHMLSELEEVIQYKLVPERREIIRQ

IWWERLQGCQRIVEDWQKILMVRSLVVSPHEDMRTWLKYASLCGKSGRL

ALAHKTLVLLLGVDPSRQLDHPLPTVHPQVTYAYMKNMWKSARKIDAFQ

HMQHFVQTMQQQAQHAIATEDQQHKQELHKLMARCFLKLGEWQLNLQGI

NESTIPKVLQYYSAATEHDRSWYKAWHAWAVMNFEAVLHYKHQNQARDE

KKKLRHASGANITNATTAATTAATATTTASTEGSNSESEAESTENSPTP

SPLQKKVTEDLSKTLLMYTVPAVQGFFRSISLSRGNNLQDTLRVLTLWF

DYGHWPDVNEALVEGVKAIQIDTWLQVIPQLIARIDTPRPLVGRLIHQL

LTDIGRYHPQALIYPLTVASKSTTTARHNAANKILKNMCEHSNTLVQQA

MMVSEELIRVAILWHEMWHEGLEEASRLYFGERNVKGMFEVLEPLHAMM

ERGPQTLKETSFNQAYGRDLMEAQEWCRKYMKSGNVKDLTQAWDLYYHV

FRRISKQLPQLTSLELQYVSPKLLMCRDLELAVPGTYDPNQPIIRIQSI

APSLQVITSKQRPRKLTLMGSNGHEFVFLLKGHEDLRQDERVMQLFGLV

NTLLANDPTSLRKNLSIQRYAVIPLSTNSGLIGWVPHCDTLHALIRDYR

EKKKILLNIEHRIMLRMAPDYDHLTLMQKVEVFEHAVNNTAGDDLAKLL

WLKSPSSEVWFDRRTNYTRSLAVMSMVGYILGLGDRHPSNLMLDRLSGK

ILHIDFGDCFEVAMTREKFPEKIPFRLTRMLTNAMEVTGLDGNYRITCH

TVMEVLREHKDSVMAVLEAFVYDPLLNWRLMDINTKGNKRSRTRTDSYS

AGQSVEILDGVELGEPAHKKTGTTVPESIHSFIGDGLVKPEALNKKAIQ

IINRVRDKLTGRDFSHDDTLDVPTQVELLIKQATSHENLCQCYIGWCPF

W

The CTT codon, which encodes amino acid residue L2185, is located at nucleotide position 137,970-137972 in the human mTOR gene (Accession No. NG_033239). Additionally, the corresponding mTOR cDNA is shown below as SEQ ID NO:2 (the CTT codon is highlighted in grey). As discussed above, equivalent residues are present in corresponding mTOR genes derived from other mammals. While the nucleic acid residues described herein are numbered in reference to the human form of mTOR; one skilled in the art may readily determine equivalent residues in a different mammal using known techniques and algorithms (e.g., BLAST, ALIGN or ExPASy).

mTOR cDNA (SEQ ID NO: 2)
```
GCTCCCGGCTTAGAGGACAGCGGGGAAGGCGGGCGGTGGGGCAGGGGGCCTGAAGCGGC
GGTACCGGTGCTGGCGGCGGCAGCTGAGGCCTTGGCCGAAGCCGCGCGAACCTCAGGGC
AAGATGCTTGGAACCGGACCTGCCGCCGCCACCACCGCTGCCACCACATCTAGCAATGT
GAGCGTCCTGCAGCAGTTTGCCAGTGGCCTAAAGAGCCGGAATGAGGAAACCAGGGCCA
AAGCCGCCAAGGAGCTCCAGCACTATGTCACCATGGAACTCCGAGAGATGAGTCAAGAG
GAGTCTACTCGCTTCTATGACCAACTGAACCATCACATTTTTGAATTGGTTTCCAGCTC
AGATGCCAATGAGAGGAAAGGTGGCATCTTGGCCATAGCTAGCCTCATAGGAGTGGAAG
GTGGGAATGCCACCCGAATTGGCAGATTTGCCAACTATCTTCGGAACCTCCTCCCCTCC
AATGACCCAGTTGTCATGGAAATGGCATCCAAGGCCATTGGCCGTCTTGCCATGGCAGG
GGACACTTTTACCGCTGAGTACGTGGAATTTGAGGTGAAGCGAGCCCTGGAATGGCTGG
GTGCTGACCGCAATGAGGGCCGGAGACATGCAGCTGTCCTGGTTCTCCGTGAGCTGGCC
ATCAGCGTCCCTACCTTCTTCTTCCAGCAAGTGCAACCCTTCTTTGACAACATTTTTGT
GGCCGTGTGGGACCCCAAACAGGCCATCCGTGAGGGAGCTGTAGCCGCCCTTCGTGCCT
GTCTGATTCTCACAACCCAGCGTGAGCCGAAGGAGATGCAGAAGCCTCAGTGGTACAGG
CACACATTTGAAGAAGCAGAGAAGGGATTTGATGAGACCTTGGCCAAAGAGAAGGGCAT
GAATCGGGATGATCGGATCCATGGAGCCTTGTTGATCCTTAACGAGCTGGTCCGAATCA
GCAGCATGGAGGGAGAGCGTCTGAGAGAAGAAATGGAAGAAATCACACAGCAGCAGCTG
GTACACGACAAGTACTGCAAAGATCTCATGGGCTTCGGAACAAAACCTCGTCACATTAC
CCCCTTCACCAGTTTCCAGGCTGTACAGCCCCAGCAGTCAAATGCCTTGGTGGGGCTGC
TGGGGTACAGCTCTCACCAAGGCCTCATGGGATTTGGGACCTCCCCCAGTCCAGCTAAG
TCCACCCTGGTGGAGAGCCGGTGTTGCAGAGACTTGATGGAGGAGAAATTTGATCAGGT
GTGCCAGTGGGTGCTGAAATGCAGGAATAGCAAGAACTCGCTGATCCAAATGACAATCC
TTAATTTGTTGCCCCGCTTGGCTGCATTCCGACCTTCTGCCTTCACAGATACCCAGTAT
CTCCAAGATACCATGAACCATGTCCTAAGCTGTGTCAAGAAGGAGAAGGAACGTACAGC
GGCCTTCCAAGCCCTGGGGCTACTTTCTGTGGCTGTGAGGTCTGAGTTTAAGGTCTATT
TGCCTCGCGTGCTGGACATCATCCGAGCGGCCCTGCCCCCAAAGGACTTCGCCCATAAG
AGGCAGAAGGCAATGCAGGTGGATGCCACAGTCTTCACTTGCATCAGCATGCTGGCTCG
AGCAATGGGGCCAGGCATCCAGCAGGATATCAAGGAGCTGCTGGAGCCCATGCTGGCAG
TGGGACTAAGCCCTGCCCTCACTGCAGTGCTCTACGACCTGAGCCGTCAGATTCCACAG
CTAAAGAAGGACATTCAAGATGGGCTACTGAAAATGCTGTCCCTGGTCCTTATGCACAA
ACCCCTTCGCCACCCAGGCATGCCCAAGGGCCTGGCCCATCAGCTGGCCTCTCCTGGCC
TCACGACCCTCCCTGAGGCCAGCGATGTGGGCAGCATCACTCTTGCCCTCCGAACGCTT
GGCAGCTTTGAATTTGAAGGCCACTCTCTGACCCAATTTGTTCGCCACTGTGCGGATCA
TTTCCTGAACAGTGAGCACAAGGAGATCCGCATGGAGGCTGCCCGCACCTGCTCCCGCC
TGCTCACACCCTCCATCCACCTCATCAGTGGCCATGCTCATGTGGTTAGCCAGACCGCA
GTGCAAGTGGTGGCAGATGTGCTTAGCAAACTGCTCGTAGTTGGGATAACAGATCCTGA
CCCTGACATTCGCTACTGTGTCTTGGCGTCCCTGGACGAGCGCTTTGATGCACACCTGG
CCCAGGCGGAGAACTTGCAGGCCTTGTTTGTGGCTCTGAATGACCAGGTGTTTGAGATC
```

-continued

```
CGGGAGCTGGCCATCTGCACTGTGGGCCGACTCAGTAGCATGAACCCTGCCTTTGTCAT

GCCTTTCCTGCGCAAGATGCTCATCCAGATTTTGACAGAGTTGGAGCACAGTGGGATTG

GAAGAATCAAAGAGCAGAGTGCCCGCATGCTGGGGCACCTGGTCTCCAATGCCCCCCGA

CTCATCCGCCCCTACATGGAGCCTATTCTGAAGGCATTAATTTTGAAACTGAAAGATCC

AGACCCTGATCCAAACCCAGGTGTGATCAATAATGTCCTGGCAACAATAGGAGAATTGG

CACAGGTTAGTGGCCTGGAAATGAGGAAATGGGTTGATGAACTTTTTATTATCATCATG

GACATGCTCCAGGATTCCTCTTTGTTGGCCAAAAGGCAGGTGGCTCTGTGGACCCTGGG

ACAGTTGGTGGCCAGCACTGGCTATGTAGTAGAGCCCTACAGGAAGTACCCTACTTTGC

TTGAGGTGCTACTGAATTTTCTGAAGACTGAGCAGAACCAGGGTACACGCAGAGAGGCC

ATCCGTGTGTTAGGGCTTTTAGGGGCTTTGGATCCTTACAAGCACAAAGTGAACATTGG

CATGATAGACCAGTCCCGGGATGCCTCTGCTGTCAGCCTGTCAGAATCCAAGTCAAGTC

AGGATTCCTCTGACTATAGCACTAGTGAAATGCTGGTCAACATGGGAAACTTGCCTCTG

GATGAGTTCTACCCAGCTGTGTCCATGGTGGCCCTGATGCGGATCTTCCGAGACCAGTC

ACTCTCTCATCATCACACCATGGTTGTCCAGGCCATCACCTTCATCTTCAAGTCCCTGG

GACTCAAATGTGTGCAGTTCCTGCCCCAGGTCATGCCCACGTTCCTTAACGTCATTCGA

GTCTGTGATGGGGCCATCCGGGAATTTTTGTTCCAGCAGCTGGGAATGTTGGTGTCCTT

TGTGAAGAGCCACATCAGACCTTATATGGATGAAATAGTCACCCTCATGAGAGAATTCT

GGGTCATGAACACCTCAATTCAGAGCACGATCATTCTTCTCATTGAGCAAATTGTGGTA

GCTCTTGGGGGTGAATTTAAGCTCTACCTGCCCCAGCTGATCCCACACATGCTGCGTGT

CTTCATGCATGACAACAGCCCAGGCCGCATTGTCTCTATCAAGTTACTGGCTGCAATCC

AGCTGTTTGGCGCCAACCTGGATGACTACCTGCATTTACTGCTGCCTCCTATTGTTAAG

TTGTTTGATGCCCCTGAAGCTCCACTGCCATCTCGAAAGGCAGCGCTAGAGACTGTGGA

CCGCCTGACGGAGTCCCTGGATTTCACTGACTATGCCTCCCGGATCATTCACCCTATTG

TTCGAACACTGGACCAGAGCCCAGAACTGCGCTCCACAGCCATGGACACGCTGTCTTCA

CTTGTTTTTCAGCTGGGGAAGAAGTACCAAATTTTCATTCCAATGGTGAATAAAGTTCT

GGTGCGACACCGAATCAATCATCAGCGCTATGATGTGCTCATCTGCAGAATTGTCAAGG

GATACACACTTGCTGATGAAGAGGAGGATCCTTTGATTTACCAGCATCGGATGCTTAGG

AGTGGCCAAGGGGATGCATTGGCTAGTGGACCAGTGGAAACAGGACCCATGAAGAAACT

GCACGTCAGCACCATCAACCTCCAAAAGGCCTGGGGCGCTGCCAGGAGGGTCTCCAAAG

ATGACTGGCTGGAATGGCTGAGACGGCTGAGCCTGGAGCTGCTGAAGGACTCATCATCG

CCCTCCCTGCGCTCCTGCTGGGCCCTGGCACAGGCCTACAACCCGATGGCCAGGGATCT

CTTCAATGCTGCATTTGTGTCCTGCTGGTCTGAACTGAATGAAGATCAACAGGATGAGC

TCATCAGAAGCATCGAGTTGGCCCTCACCTCACAAGACATCGCTGAAGTCACACAGACC

CTCTTAAACTTGGCTGAATTCATGGAACACAGTGACAAGGGCCCCCTGCCACTGAGAGA

TGACAATGGCATTGTTCTGCTGGGTGAGAGCTGCCAAGTGCCGAGCATATGCCAAAG

CACTACACTACAAAGAACTGGAGTTCCAGAAAGGCCCCACCCCTGCCATTCTAGAATCT

CTCATCAGCATTAATAATAAGCTACAGCAGCCGGAGGCAGCGGCCGGAGTGTTAGAATA

TGCCATGAAACACTTTGGAGAGCTGGAGATCCAGGCTACCTGGTATGAGAAACTGCACG

AGTGGGAGGATGCCCTTGTGGCCTATGACAAGAAAATGGACACCAACAAGGACGACCCA

GAGCTGATGCTGGGCCGCATGCGCTGCCTCGAGGCCTTGGGGGAATGGGTCAACTCCA
```

```
CCAGCAGTGCTGTGAAAAGTGGACCCTGGTTAATGATGAGACCCAAGCCAAGATGGCCC

GGATGGCTGCTGCAGCTGCATGGGGTTTAGGTCAGTGGGACAGCATGGAAGAATACACC

TGTATGATCCCTCGGGACACCCATGATGGGGCATTTTATAGAGCTGTGCTGGCACTGCA

TCAGGACCTCTTCTCCTTGGCACAACAGTGCATTGACAAGGCCAGGGACCTGCTGGATG

CTGAATTAACTGCGATGGCAGGAGAGAGTTACAGTCGGGCATATGGGGCCATGGTTTCT

TGCCACATGCTGTCCGAGCTGGAGGAGGTTATCCAGTACAAACTTGTCCCCGAGCGACG

AGAGATCATCCGCCAGATCTGGTGGGAGAGACTGCAGGGCTGCCAGCGTATCGTAGAGG

ACTGGCAGAAAATCCTTATGGTGCGGTCCCTTGTGGTCAGCCCTCATGAAGACATGAGA

ACCTGGCTCAAGTATGCAAGCCTGTGCGGCAAGAGTGGCAGGCTGGCTCTTGCTCATAA

AACTTTAGTGTTGCTCCTGGGAGTTGATCCGTCTCGGCAACTTGACCATCCTCTGCCAA

CAGTTCACCCTCAGGTGACCTATGCCTACATGAAAAACATGTGGAAGAGTGCCCGCAAG

ATCGATGCCTTCCAGCACATGCAGCATTTTGTCCAGACCATGCAGCAACAGGCCCAGCA

TGCCATCGCTACTGAGGACCAGCAGCATAAGCAGGAACTGCACAAGCTCATGGCCCGAT

GCTTCCTGAAACTTGGAGAGTGGCAGCTGAATCTACAGGGCATCAATGAGAGCACAATC

CCCAAAGTGCTGCAGTACTACAGCGCCGCCACAGAGCACGACCGCAGCTGGTACAAGGC

CTGGCATGCGTGGGCAGTGATGAACTTCGAAGCTGTGCTACACTACAAACATCAGAACC

AAGCCCGCGATGAGAAGAAGAAACTGCGTCATGCCAGCGGGGCCAACATCACCAACGCC

ACCACTGCCGCCACCACGGCCGCCACTGCCACCACCACTGCCAGCACCGAGGGCAGCAA

CAGTGAGAGCGAGGCCGAGAGCACCGAGAACAGCCCCACCCCATCGCCGCTGCAGAAGA

AGGTCACTGAGGATCTGTCCAAAACCCTCCTGATGTACACGGTGCCTGCCGTCCAGGGC

TTCTTCCGTTCCATCTCCTTGTCACGAGGCAACAACCTCCAGGATACACTCAGAGTTCT

CACCTTATGGTTTGATTATGGTCACTGGCCAGATGTCAATGAGGCCTTAGTGGAGGGGG

TGAAAGCCATCCAGATTGATACCTGGCTACAGGTTATACCTCAGCTCATTGCAAGAATT

GATACGCCCAGACCCTTGGTGGGACGTCTCATTCACCAGCTTCTCACAGACATTGGTCG

GTACCACCCCCAGGCCCTCATCTACCCACTGACAGTGGCTTCTAAGTCTACCACGACAG

CCCGGCACAATGCAGCCAACAAGATTCTGAAGAACATGTGTGAGCACAGCAACACCCTG

GTCCAGCAGGCCATGATGGTGAGCGAGGAGCTGATCCGAGTGGCCATCCTCTGGCATGA

GATGTGGCATGAAGGCCTGGAAGAGGCATCTCGTTTGTACTTTGGGGAAAGGAACGTGA

AAGGCATGTTTGAGGTGCTGGAGCCCTTGCATGCTATGATGGAACGGGGCCCCCAGACT

CTGAAGGAAACATCCTTTAATCAGGCCTATGGTCGAGATTTAATGGAGGCCCAAGAGTG

GTGCAGGAAGTACATGAAATCAGGGAATGTCAAGGACCTCACCCAAGCCTGGGACCTCT

ATTATCATGTGTTCCGACGAATCTCAAAGCAGCTGCCTCAGCTCACATCCTTAGAGCTG

CAATATGTTTCCCCAAAACTTCTGATGTGCCGGGACCTTGAATTGGCTGTGCCAGGAAC

ATATGACCCCAACCAGCCAATCATTCGCATTCAGTCCATAGCACCGTCTTTGCAAGTCA

TCACATCCAAGCAGAGGCCCCGGAAATTGACACTTATGGGCAGCAACGGACATGAGTTT

GTTTTC▒▒▒CTAAAAGGCCATGAAGATCTGCGCCAGGATGAGCGTGTGATGCAGCTCTT

CGGCCTGGTTAACACCCTTCTGGCCAATGACCCAACATCTCTTCGGAAAAACCTCAGCA

TCCAGAGATACGCTGTCATCCCTTTATCGACCAACTCGGGCCTCATTGGCTGGGTTCCC

CACTGTGACACACTGCACGCCCTCATCCGGGACTACAGGGAGAAGAAGAAGATCCTTCT

CAACATCGAGCATCGCATCATGTTGCGGATGGCTCCGGACTATGACCACTTGACTCTGA

TGCAGAAGGTGGAGGTGTTTGAGCATGCCGTCAATAATACAGCTGGGGACGACCTGGCC
```

-continued

```
AAGCTGCTGTGGCTGAAAAGCCCCAGCTCCGAGGTGTGGTTTGACCGAAGAACCAATTA
TACCCGTTCTTTAGCGGTCATGTCAATGGTTGGGTATATTTTAGGCCTGGGAGATAGAC
ACCCATCCAACCTGATGCTGGACCGTCTGAGTGGGAAGATCCTGCACATTGACTTTGGG
GACTGCTTTGAGGTTGCTATGACCCGAGAGAAGTTTCCAGAGAAGATTCCATTTAGACT
AACAAGAATGTTGACCAATGCTATGGAGGTTACAGGCCTGGATGGCAACTACAGAATCA
CATGCCACACAGTGATGGAGGTGCTGCGAGAGCACAAGGACAGTGTCATGGCCGTGCTG
GAAGCCTTTGTCTATGACCCCTTGCTGAACTGGAGGCTGATGGACACAAATACCAAGG
CAACAAGCGATCCCGAACGAGGACGGATTCCTACTCTGCTGGCCAGTCAGTCGAAATTT
TGGACGGTGTGGAACTTGGAGAGCCAGCCCATAAGAAACGGGGACCACAGTGCCAGAA
TCTATTCATTCTTTCATTGGAGACGGTTTGGTGAAACCAGAGGCCCTAAATAAGAAAGC
TATCCAGATTATTAACAGGGTTCGAGATAAGCTCACTGGTCGGGACTTCTCTCATGATG
ACACTTTGGATGTTCCAACGCAAGTTGAGCTGCTCATCAAACAAGCGACATCCCATGAA
AACCTCTGCCAGTGCTATATTGGCTGGTGCCCTTTCTGGTAACTGGAGGCCCAGATGTG
CCCATCACGTTTTTTCTGAGGCTTTTGTACTTTAGTAAATGCTTCCACTAAACTGAAAC
CATGGTGAGAAAGTTTGACTTTGTTAAATATTTTGAAATGTAAATGAAAAGAACTACTG
TATATTAAAAGTTGGTTTGAACCAACTTTCTAGCTGCTGTTGAAGAATATATTGTCAGA
AACACAAGGCTTGATTTGGTTCCCAGGACAGTGAAACATAGTAATACCACGTAAATCAA
GCCATTCATTTTGGGGAACAGAAGATCCATAACTTTAGAAATACGGGTTTTGACTTAAC
TCACAAGAGAACTCATCATAAGTACTTGCTGATGGAAGAATGACCTAGTTGCTCCTCTC
AACATGGGTACAGCAAACTCAGCACAGCCAAGAAGCCTCAGGTCGTGGAGAACATGGAT
TAGGATCCTAGACTGTAAAGACACAGAAGATGCTGACCTCACCCCTGCCACCTATCCCA
AGACCTCACTGGTCTGTGGACAGCAGCAGAAATGTTTGCAAGATAGGCCAAAATGAGTA
CAAAAGGTCTGTCTTCCATCAGACCCAGTGATGCTGCGACTCACACGCTTCAATTCAAG
ACCTGACCGCTAGTAGGGAGGTTTATTCAGATCGCTGGCAGCCTCGGCTGAGCAGATGC
ACAGAGGGGATCACTGTGCAGTGGGACCACCCTCACTGGCCTTCTGCAGCAGGGTTCTG
GGATGTTTTCAGTGGTCAAAATACTCTGTTTAGAGCAAGGGCTCAGAAAACAGAAATAC
TGTCATGGAGGTGCTGAACACAGGGAAGGTCTGGTACATATTGGAAATTATGAGCAGAA
CAAATACTCAACTAAATGCACAAAGTATAAAGTGTAGCCATGTCTAGACACCATGTTGT
ATCAGAATAATTTTTGTGCCAATAAATGACATCAGAATTTTAAACATATGTAAAAAAAA
A
```

Alignment of mTOR cDNA and Protein Sequences (Below, SEQ ID NO: 2 is Disclosed as the Nucleic Acid Sequence and SEQ ID NO: 1 is Disclosed as the Amino Acid Sequence)

```
gctcccggcttagaggacagcggggaaggcgggcggtggggcaggggcctgaagcggcgg taccggtgctggcggcggcagctgaggccttggccgaagccgcgcgaacctcagggcaag atgcttggaaccggacctgccgccgccaccaccgctgccaccacatctagcaatgtgagc
 M   L   G   T   G   P   A   A   A   T   T   A   A   T   T   S   S   N   V   S gtcctgcagcagtttgccagtggcctaaagagccggaatgaggaaaccagggccaaagcc
 V   L   Q   Q   F   A   S   G   L   K   S   R   N   E   E   T   R   A   K   A gccaaggagctccagcactatgtcaccatggaactccgagagatgagtcaagaggagtct
 A   K   E   L   Q   H   Y   V   T   M   E   L   R   E   M   S   Q   E   E   S
```

```
actcgcttctatgaccaactgaaccatcacatttttgaattggtttccagctcagatgcc
 T  R  F  Y  D  Q  L  N  H  H  I  F  E  L  V  S  S  S  D  A aatgagaggaaaggtggcatcttggccatagctagcctcataggagtggaaggtgggaat
 N  E  R  K  G  G  I  L  A  I  A  S  L  I  G  V  E  G  G  N gccacccgaattggcagattrgccaactatcttcggaacctcctcccctccaatgaccca
 A  T  R  I  G  R  F  A  N  Y  L  R  N  L  L  P  S  N  D  P gttgtcatggaaatggcatccaaggccattggccgtcttgccatggcaggggacactttt
 V  V  M  E  M  A  S  K  A  I  G  R  L  A  M  A  G  D  T  F accgctgagtacgtggaatttgaggtgaagcgagccctggaatggctgggtgctgaccgc
 T  A  E  Y  V  E  F  E  V  K  R  A  L  E  W  L  G  A  D  R aatgagggccrgagacatgcagctgtcctggttctccgtgagctggccatcagcgtccct
 N  E  G  R  R  H  A  A  V  L  V  L  R  E  L  A  I  S  V  P accttcttcttccagcaagtgcaacccttctttgacaacatttttgtggccgtgtgggac
 T  F  F  F  Q  Q  V  Q  P  F  F  D  N  I  F  V  A  V  W  D cccaaacaggccatccgtgagggagctgtagccgcccttcgtgcctgtctgattcccaca
 P  K  Q  A  I  R  E  G  A  V  A  A  L  R  A  C  L  I  L  T acccagcgtgagccgaaggagatgcagaagccrcagtggtacaggcacacatttgaagaa
 T  Q  R  E  P  K  E  M  Q  K  P  Q  W  Y  R  H  T  F  E  E gcagagaagggatttgatgagaccttggccaaagagaagggcatgaatcgggatgatcgg
 A  E  K  G  F  D  E  T  L  A  K  E  K  G  M  N  R  D  D  R atccatggagccttgttgatccttaacgagctggtccgaatcagcagcatggagggagag
 I  H  G  A  L  L  I  L  N  E  L  V  R  I  S  S  M  E  G  E cgtctgagagaagaaatggaagaaatcacacagcagcagctggtacacgacaagtactgc
 R  L  R  E  E  M  E  E  I  T  Q  Q  Q  L  V  H  D  K  Y  C aaagatctcatgggcttcggaacaaaacctcgtcacattacccccttccccagtttccag
 K  D  L  M  G  F  G  T  K  P  R  H  I  T  P  F  T  S  F  Q gctgtacagccccagcagtcaaatgccttggtggggctgctggggtacagctctcaccaa
 A  V  Q  P  Q  Q  S  N  A  L  V  G  L  L  G  Y  S  S  H  Q ggcctcatgggatttgggacctcccccagtccagctaagtccaccctggtggagagccgg
 G  L  M  G  F  G  T  S  P  S  P  A  K  S  T  L  V  E  S  R tgttgcagagacttgatggaggagaaatttgatcaggtgtgccagtgggtgctgaaatgc
 C  C  R  D  L  M  E  E  K  F  D  Q  V  C  Q  W  V  L  K  C aggaatagcaagaactcgctgatccaaatgacaatccttaatttgttgccccgcttggct
 R  N  S  K  N  S  L  I  Q  M  T  I  L  N  L  L  P  R  L  A gcattccgaccttctgccttcacagatacccagtatctccaagataccatgaaccatgtc
 A  F  R  P  S  A  F  T  D  T  Q  Y  L  Q  D  T  M  N  H  V ctaagctgtgtcaagaaggagaaggaacgtacagcggccttccaagccctggggctactt
 L  S  C  V  K  K  E  K  E  R  T  A  A  F  Q  A  L  G  L  L tctgtggctgtgaggtctgagtttaaggtctatttgcctcgcgtgctggacatcatccga
 S  V  A  V  R  S  E  F  K  V  Y  L  P  R  V  L  D  I  I  R gcggccctgccccaaaggacttcgcccataagaggcagaaggcaatccaggtggatgcc
 A  A  L  P  P  K  D  F  A  H  K  R  Q  K  A  M  Q  V  D  A acagtcttcacttgcatcagcatgctggctcgagcaatggggccaggcatccagcaggat
 T  V  F  T  C  I  S  M  L  A  R  A  M  G  P  G  I  Q  Q  D atcaaggagctgctggagcccatgctggcagtgggactaagccctgccctcactgcagtg
 I  K  E  L  L  E  P  M  L  A  V  G  L  S  P  A  L  T  A  V ctctacgacctgagccgtcagattccacagctaaagaaggacattcaagatgggctactg
 L  Y  D  L  S  R  Q  I  P  Q  L  K  K  D  I  Q  D  G  L  L aaaatgctgtccctggtccttatgcacaaaccccttcgccacccaggcatgcccaagggc
 K  M  L  S  L  V  L  M  H  K  P  L  R  H  P  G  M  P  K  G ctggcccatcagctggcctctcctggcctcacgaccctccctgaggccagcgatgtgggc
 L  A  H  Q  L  A  S  P  G  L  T  T  L  P  E  A  S  D  V  G agcatcactcttgccctccgaacgcttggcagctttgaatttgaaggccactctctgacc
 S  I  T  L  A  L  R  T  L  G  S  F  E  F  E  G  H  S  L  T
```

-continued

```
caatttgttcgccactgtgcggatcatttcctgaacagtgagcacaaggagatccgcatg
 Q   F   V   R   H   C   A   D   H   F   L   N   S   E   H   K   E   I   R   M gaggctgcccgcacctgctcccgcctgctcacaccctccatccacctcatcagtggccat
 E   A   A   R   T   C   S   R   L   L   T   P   S   I   H   L   I   S   G   H gctcatgtggttagccagaccgcagtgcaagtggtggcagatgtgcttagcaaactgctc
 A   H   V   V   S   Q   T   A   V   Q   V   V   A   D   V   L   S   K   L   L gtagttgggataacagatcctgaccctgacattcgctactgtgtcttggcgtccctggac
 V   V   G   I   T   D   P   D   P   D   I   R   Y   C   V   L   A   S   L   D gagcgctttgatgcacacctggcccaggcggagaacttgcaggccttgtttgtggctctg
 E   R   F   D   A   H   L   A   Q   A   E   N   L   Q   A   L   F   V   A   L aatgaccaggtgtttgagatccgggagctggccatctgcactgtgggccgactcagtagc
 N   D   Q   V   F   E   I   R   E   L   A   I   C   T   V   G   R   L   S   S atgaaccctgccttgtcatgcctttcctgcgcaagatgctcatccagattttgacagag
 M   N   P   A   F   V   M   P   F   L   R   K   M   L   I   Q   I   L   T   E ttggagcacagtgggattggaagaatcaaagagcagagtgcccgcatgctggggcacctg
 L   E   H   S   G   I   G   R   I   K   E   Q   S   A   R   M   L   G   H   L gtctccaatgcccccgactcatccgcccctacatggagcctattctgaaggcattaatt
 V   S   N   A   P   R   L   I   R   P   Y   M   E   P   I   L   K   A   L   I ttgaaactgaaagatccagaccctgatccaaacccaggtgtgatcaataatgtcctggca
 L   K   L   K   D   P   D   P   D   P   N   P   G   V   I   N   N   V   L   A acaataggagaattggcacaggttagtggcctggaaatgaggaaatgggttgatgaactt
 T   I   G   E   L   A   Q   V   S   G   L   E   M   R   K   W   V   D   E   L tttattatcatcatggacatgctccaggattcctctttgttggccaaaaggcaggtggct
 F   I   I   I   M   D   M   L   Q   D   S   S   L   L   A   K   R   Q   V   A ctgtggaccctgggacagttggtggccagcactggctatgtagtagagccctacaggaag
 L   W   T   L   G   Q   L   V   A   S   T   G   Y   V   V   E   P   Y   R   K taccctactttgcttgaggtgctactgaattttctgaagactgagcagaaccagggtaca
 Y   P   T   L   L   E   V   L   L   N   F   L   K   T   E   Q   N   Q   G   T cgcagagaggccatccgtgtgttagggcttttaggggctttggatccttacaagcacaaa
 R   R   E   A   I   R   V   L   G   L   L   G   A   L   D   P   Y   K   H   K gtgaacattggcatgatagaccagtcccgggatgcctctgctgtcagcctgtcagaatcc
 V   N   I   G   M   I   D   Q   S   R   D   A   S   A   V   S   L   S   E   S aagtcaagtcaggattcctctgactatagcactagtgaaatgctggtcaacatgggaaac
 K   S   S   Q   D   S   S   D   Y   S   T   S   E   M   L   V   N   M   G   N ttgcctctggatgagttctacccagctgtgtccatggtggccctgatgcggatcttccga
 L   P   L   D   E   F   Y   P   A   V   S   M   V   A   L   M   R   I   F   R gaccagtcactctctcatcatcacaccatggttgtccaggccatcaccttcatcttcaag
 D   Q   S   L   S   H   H   H   T   M   V   V   Q   A   I   T   F   I   F   K tccctgggactcaaatgtgtgcagttcctgccccaggtcatgcccacgttccttaacgtc
 S   L   G   L   K   C   V   Q   F   L   P   Q   V   M   P   T   F   L   N   V attcgagtctgtgatggggccatccgggaatttttgttccagcagctgggaatgttggtg
 I   R   V   C   D   G   A   I   R   E   F   L   F   Q   Q   L   G   M   L   V tcctttgtgaagagccacatcagacccttatatggatgaaatagtcaccctcatgagagaa
 S   F   V   K   S   H   I   R   P   Y   M   D   E   I   V   T   L   M   R   E ttctgggtcatgaacacctcaattcagagcacgatcattcttctcattgagcaaattgtg
 F   W   V   M   N   T   S   I   Q   S   T   I   I   L   L   I   E   Q   I   V gtagctcttgggggtgaatttaagctctacctgccccagctgatcccacacatgctgcgt
 V   A   L   G   G   E   F   K   L   Y   L   P   Q   L   I   P   H   M   L   R gtcttcatgcatgacaacagcccaggccgcattgtctctatcaagttactggctgcaatc
 V   F   M   H   D   N   S   P   G   R   I   V   S   I   K   L   L   A   A   I cagctgtttggcgccaacctggatgactacctgcatttactgctgcctcctattgttaag
 Q   L   F   G   A   N   L   D   D   Y   L   H   L   L   P   P   I   V   K ttgtttgatgcccctgaagctccactgccatctcgaaaggcagcgctagagactgtggac
 L   F   D   A   P   E   A   P   L   P   S   R   K   A   A   L   E   T   V   D
```

```
cgcctgacggagtccctggatttcactgactatgcctcccggatcattcacccctattgtt
 R  L  T  E  S  L  D  F  T  D  Y  A  S  R  I  I  H  P  I  V cgaacactggaccagagcccagaactgcgctccacagccatggacacgctgtcttcactt
 R  T  L  D  Q  S  P  E  L  R  S  T  A  M  D  T  L  S  S  L gtttttcagctggggaagaagtaccaaattttcattccaatggtgaataaagttctggtg
 V  F  Q  L  G  K  K  Y  Q  I  F  I  P  M  V  N  K  V  L  V cgacaccgaatcaatcatcagcgctatgatgtgctcatctgcagaattgtcaagggatac
 R  H  R  I  N  H  Q  R  Y  D  V  L  I  C  R  I  V  K  G  Y acacttgctgatgaagaggaggatcctttgatttaccagcatcggatgcttaggagtggc
 T  L  A  D  E  E  E  D  P  L  I  Y  Q  H  R  M  L  R  S  G caagggggatgcattggctagtggaccagtggaaacaggacccatgaagaaactgcacgtc
 Q  G  D  A  L  A  S  G  P  V  E  T  G  P  M  K  K  L  H  V agcaccatcaacctccaaaaggcctggggcgctgccaggagggtctccaaagatgactgg
 S  T  I  N  L  Q  K  A  W  G  A  A  R  R  V  S  K  D  D  W ctggaatggctgagacggctgagcctggagctgctgaaggactcatcatcgccctccctg
 L  E  W  L  R  R  L  S  L  E  L  L  K  D  S  S  S  P  S  L cgctcctgctgggccctggcacaggcctacaacccgatggccagggatctcttcaatgct
 R  S  C  W  A  L  A  Q  A  Y  N  P  M  A  R  D  L  F  N  A gcatttgtgtcctgctggtctgaactgaatgaagatcaacaggatgagctcatcagaagc
 A  F  V  S  C  W  S  E  L  N  E  D  Q  Q  D  E  L  I  R  S atcgagttggccctcacctcacaagacatcgctgaagtcacacagaccctcttaaacttg
 I  E  L  A  L  T  S  Q  D  I  A  E  V  T  Q  T  L  L  N  L gctgaattcatggaacacagtgacaagggcccctgccactgagagatgacaatggcatt
 A  E  F  M  E  H  S  D  K  G  P  L  P  L  R  D  D  N  G  I gttctgctgggtgagagagctgccaagtgccgagcatatgccaaagcactacactacaaa
 V  L  L  G  E  R  A  A  K  C  R  A  Y  A  K  A  L  H  Y  K gaactggagttccagaaaggccccacccctgccattctagaatctctcatcagcattaat
 E  L  E  F  Q  K  G  P  T  P  A  I  L  E  S  L  I  S  I  N aataagctacagcagccggaggcagcggccggagtgttagaatatgccatgaaacacttt
 N  K  L  Q  Q  P  E  A  A  A  G  V  L  E  Y  A  M  K  H  F ggagagctggagatccaggctacctggtatgagaaactgcacgagtgggaggatgccctt
 G  E  L  E  I  Q  A  T  W  Y  E  K  L  H  E  W  E  D  A  L gtggcctatgacaagaaaatggacaccaacaaggacgacccagagctgatgctgggccgc
 V  A  Y  D  K  K  M  D  T  N  K  D  D  P  E  L  M  L  G  R atgcgctgcctcgaggccttgggggaatgggtcaactccaccagcagtgctgtgaaaag
 M  R  C  L  E  A  L  G  E  W  G  Q  L  H  Q  Q  C  C  E  K tggaccctggttaatgatgagacccaagccaagatggcccggatggctgctgcagctgca
 W  T  L  V  N  D  E  T  Q  A  K  M  A  R  M  A  A  A  A  A tggggtttaggtcagtgggacagcatggaagaatacacctgtatgatccctcgggacacc
 W  G  L  G  Q  W  D  S  M  E  E  Y  T  C  M  I  P  R  D  T catgatggggcattttatagagctgtgctggcactgcatcaggacctcttctccttggca
 H  D  G  A  F  Y  R  A  V  L  A  L  H  Q  D  L  F  S  L  A caacagtgcattgacaaggccagggacctgctggatgctgaattaactgcgatggcagga
 Q  Q  C  I  D  K  A  R  D  L  L  D  A  E  L  T  A  M  A  G gagagttacagtcgggcatatggggccatggtttcttgccacatgctgtccgagctggag
 E  S  Y  S  R  A  Y  G  A  M  V  S  C  H  M  L  S  E  L  E gaggtttatccagtacaaacttgtccccgagcgacgagagatcatccgccagatctggtgg
 E  V  I  Q  Y  K  L  V  P  E  R  R  E  I  I  R  Q  I  W  W gagagactgcagggctgccagcgtatcgtagaggactggcagaaaatccttatggtgcgg
 E  R  L  Q  G  C  Q  R  I  V  E  D  W  Q  K  I  L  M  V  R tcccttgtggtcagccctcatgaagacatgagaacctggctcaagtatgcaagcctgtgc
 S  L  V  V  S  P  H  E  D  M  R  T  W  L  K  Y  A  S  L  C ggcaagagtggcaggctggctcttgctcataaaaactttagtgttgctcctgggagttgat
 G  K  S  G  R  L  A  L  A  H  K  T  L  V  L  L  L  G  V  D
```

```
ccgtctcggcaacttgaccatcctctgccaacagttcaccctcaggtgacctatgcctac
 P  S  R  Q  L  D  H  P  L  P  T  V  H  P  Q  V  T  Y  A  Y atgaaaaacatgcggaagagtgcccgcaagatccatgccttccagcacatgcagcatttt
 M  K  N  M  W  K  S  A  R  K  I  D  A  F  Q  H  M  Q  H  F gtccagaccatgcagcaacaggcccagcatgccatcgctactgaggaccagcagcataag
 V  Q  T  M  Q  Q  Q  A  Q  H  A  I  A  T  E  D  Q  Q  H  K caggaactgcacaagctcarggcccgatgcttcctgaaacttggagagtggcagctgaat
 Q  E  L  H  K  L  M  A  R  C  F  L  K  L  G  E  W  Q  L  N ctacagggcatcaatgagagcacaatccccaaagtgctgcagtactacagcgccgccaca
 L  Q  G  I  N  E  S  T  I  P  K  V  L  Q  Y  Y  S  A  A  T gagcacgaccgcagctggtacaaggcctggcatgcgtgggcagtgatgaacttcgaagct
 E  H  D  R  S  W  Y  K  A  W  H  A  W  A  V  M  N  F  E  A gtgctacactacaaacatcagaaccaagcccgcgatgagaagaagaaactgcgtcatgcc
 V  L  H  Y  K  H  Q  N  Q  A  R  D  Z  K  K  K  L  R  K  A agcggggccaacatcaccaacgccaccactgccgccaccacggccgccactgccaccacc
 S  G  A  N  I  T  N  A  T  T  A  A  T  T  A  A  T  A  T  T actgccagcaccgagggcagcaacagtgagagcgaggccgagagcaccgagaacagcccc
 T  A  S  T  E  G  S  N  S  E  S  E  A  E  S  T  E  N  S  P acccatcgccgctgcagaagaaggtcactgaggatctgtccaaaaccctcctgatgtac
 T  P  S  P  L  Q  K  K  V  T  E  D  L  S  K  T  L  L  M  Y acggtgcctgccgtccagggcttcttccgttccatctccttgtcacgaggcaacaacctc
 T  V  P  A  V  Q  G  F  F  R  S  I  S  L  S  R  G  N  N  L caggatacactcagagttcrcaccrtacggtttgattatgqtcactggccagatgtcaat
 Q  D  T  L  R  V  L  T  L  W  F  D  Y  G  H  W  P  D  V  N gaggccttagtggaggggggtgaaagccatccagattgatacctggctacaggttatacct
 E  A  L  V  E  G  V  K  A  I  Q  I  D  T  W  L  Q  V  I  P cagctcattgcaagaattgatacgcccagacccttggtgggacgtctcattcaccagctt
 Q  L  I  A  R  I  D  T  P  R  P  L  V  G  R  L  I  H  Q  L ctcacagacattggtcggtaccaccccccaggcccctcatctacccactgacagtggcttct
 L  T  D  I  G  R  Y  H  P  Q  A  L  I  Y  P  L  T  V  A  S aagtctaccacgacagcccggcacaatgcagccaacaagattctgaagaacatgtgtgag
 K  S  T  T  T  A  R  H  N  A  A  N  K  I  L  K  N  M  C  E cacagcaacaccctggtccagcaggccatgatggtgagcgaggagctgatccgagtggcc
 H  S  N  T  L  V  Q  Q  A  M  M  V  S  E  E  L  I  R  V  A atcctctggcatgagatgtggcatgaaggcctggaagaggcatctcgtttgtactttggg
 I  L  W  H  E  M  W  H  E  G  L  E  E  A  S  R  L  Y  F  G gaaaggaacgtgaaaggcatgtttgaggtgctggagcccttgcatgctatgatggaacgg
 S  R  N  V  K  G  M  F  E  V  L  E  P  L  H  A  M  M  E  R ggcccccagactctgaaggaaacatcctttaatcaggcctatggtcgagatttaatggag
 G  P  Q  T  L  K  E  T  S  F  N  Q  A  Y  G  R  D  L  M  E gcccaagagtggtgcaggaagtacatgaaatcagggaatgtcaaggacctcacccaagcc
 A  Q  E  W  C  R  K  Y  M  K  S  G  N  V  K  D  L  T  Q  A tgggacctctattatcatgrgttccgacgaatctcaaagcagctgcctcagctcacatcc
 W  D  L  Y  Y  H  V  F  R  R  I  S  K  Q  L  P  Q  L  T  S ttagagctgcaatatgtttcccccaaaacttctgatgtgccgggaccttgaattggctgtg
 L  E  L  Q  Y  V  S  P  K  L  L  M  C  R  D  L  E  L  A  V ccaggaacatatgaccccaaccagccaatcattcgcattcagtccatagcaccgtctttg
 P  G  T  Y  D  P  N  Q  P  I  I  R  I  Q  S  I  A  P  S  L caagtcatcacatccaagcagaggccccggaaattgacacttatgggcagcaacggacat
 Q  V  I  T  S  K  Q  R  P  R  K  L  T  I  M  G  S  N  G  H gagtttgttttcctctaaaaggccatgaagatctgcgccaggatgagcgtgtgatgcag
 E  F  V  F  L  K  G  H  E  D  L  R  Q  D  E  R  V  M  Q
```

-continued

```
ctcttcggcctggttaacacccttctggccaatgacccaacatctcttcggaaaaacctc
 L  F  G  L  V  N  T  L  L  A  N  D  P  T  S  L  R  K  N  L agcatccagagatacgctgtcatccctttatcgaccaactcgggcctcattggctgggtt
 S  I  Q  R  Y  A  V  I  P  L  S  T  N  S  G  L  I  G  W  V ccccactgtgacacactgcacgccctcatccgggactacagggagaagaagaagatcctt
 P  H  C  D  T  L  H  A  L  I  R  D  Y  R  E  K  K  K  I  L ctcaacatcgagcatcgcatcatgrtgcggatggctccggactatgaccacttgactctg
 L  N  I  E  H  R  I  M  L  R  M  A  P  D  Y  D  H  L  T  L atgcagaaggtggaggtgtttgaqcatgccgtcaataatacagctggggacgacctggcc
 M  Q  K  V  E  V  F  E  H  A  V  N  N  T  A  G  D  D  L  A aagctgctgtggctgaaaagccccagctccgaggtgtggtttgaccgaagaaccaattat
 K  L  L  W  L  K  S  P  S  S  E  V  W  F  D  R  R  T  N  Y acccgttctttagcggtcatgtcaatggttgggtatattttaggcctgggagatagacac
 T  R  S  L  A  V  M  S  M  V  G  Y  I  L  G  L  G  D  R  K ccatccaacctgatgctggaccgtctgagtgggaagatcctgcacattgactttggggac
 P  S  N  L  M  L  D  R  L  S  G  K  I  L  H  I  D  F  G  D tgctttgaggttgctatgacccgagagaagtttccagagaagattccatttagactaaca
 C  F  E  V  A  M  T  R  E  K  F  P  E  K  I  P  F  R  L  T agaatgttgaccaatgctatggaggttacaggcctggatggcaactacagaatcacatgc
 R  M  L  T  N  A  M  E  V  T  G  L  D  G  N  Y  R  I  T  C cacacagtgatggaggtgctgcgagagcacaaggacagtgtcatggccgtgctggaagcc
 H  T  V  M  E  V  L  R  E  H  K  D  S  V  M  A  V  L  E  A tttgtctatgaccccttgctgaactggaggctgatggacacaaataccaaaggcaacaag
 F  V  Y  D  P  L  L  N  W  R  L  M  D  T  N  T  K  G  N  K cgatcccgaacgaggacggattcctactctgctggccagtcagtcgaaattttggacggt
 R  S  R  T  R  T  D  S  Y  S  A  G  Q  S  V  E  I  L  D  G gtggaacttggagagccagcccataagaaaacggggaccacagtgccagaatctattcat
 V  E  L  G  E  P  A  H  K  K  T  G  T  T  V  P  E  S  I  H tctttcattggagacggtttggtgaaaccagaggccctaaataagaaagctatccagatt
 S  F  I  G  D  G  L  V  K  P  E  A  L  N  K  K  A  I  Q  I attaacagggtrcgagataagctcactggtccggacttctctcatgatgacactttggat
 I  N  R  V  R  D  K  L  T  G  R  D  F  S  H  D  D  T  L  D gttccaacgcaagttgagctgctcatcaaaeaagcgacatcccatgaaaacctctgccag
 V  P  T  Q  V  E  L  L  I  K  Q  A  T  S  H  E  N  L  C  Q tgctatattggctggtgcccttctggtaactggaggcccagatgtgcccatcacgttttt
 C  Y  I  G  W  C  P  F  W ttctgaggcttttgtactttagtaaatgcttccactaaactgaaaccatggtgagaaagt ttcactttgttaaatattttgaaatgtaaatgaaaagaactactgtatattaaaagttgg tttgaaccaactttctagctgctgttgaagaatatattgtcagaaacacaaggcttgatt tggttcccaggacagtgaaacatagtaataccacgtaaatcaagccattcattttgggga acagaagatccataactttagaaatacggggttttgacttaactcacaagagaactcatca taagtacttgctgatggaagaatgacctagttgctcctctcaacatgggtacagcaaact cagcacagccaagaagcctcaggtcgtggagaacatggattaggatcctagactgtaaag acacagaagatgctgacctcacccctgccacctatcccaagacctcactggtctgtggac agcagcagaaatgtttgcaagataggccaaaatgagtacaaaaggtctgtcttccatcag acccagtgatgctgcgactcacacgcttcaattcaagacctgaccgctagtagggaggtt tattcagatcgctggcagcctcggctgagcagatgcacagaggggatcactgtgcagtgg gaccaccctcactggccttctgcagcagggttctgggatgttttcagtggtcaaaatact ctgtttagagcaagggctcagaaaacagaaatactgtcatggaggtgctgaacacaggga
```

```
-continued
aggtctggtacatattggaaattatgagcagaacaaatactcaactaaatgcacaaagta taaagtgtagccatgtctagacaccatgttgtatcagaataattttttgtgccaataaatg acatcagaattttaaacatatgtaaaaaaaaa
```

Certain Techniques
Nucleic Acid Amplification Methods

According to the methods of the present invention, the amplification of DNA present in a physiological sample may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qβ replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Various labels that can be incorporated into or operably linked to nucleic acids are well known in the art, such as radioactive, enzymatic, and florescent labels. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the invention.

Ligase chain reaction (LCR) is also carried out in accordance with known techniques. In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

In one embodiment of the invention, the mTOR gene is amplified by PCR using primers based on the known sequence. The amplified gene is then sequenced using automated sequencers. In this manner, the mTOR gene from a subject with cancer is sequenced to identify the presence of mutation associated with resistance to a mTOR kinase inhibitor. For example, the mutation may be at nucleotide position 137,970, 137,971 and/or 137,972 of mTOR gene sequence NG_033239.

Diagnostic techniques that are useful in the methods of the invention include, but are not limited to direct DNA sequencing, PFGE analysis, allele-specific oligonucleotide (ASO), dot blot analysis and denaturing gradient gel electrophoresis, and are well known to the artisan.

There are several methods that can be used to detect DNA sequence variation. Direct DNA sequencing, either manual sequencing or automated fluorescent sequencing can detect sequence variation. Another approach is the single-stranded conformation polymorphism assay (SSCA). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments that have shifted mobility on SSCA gels are then sequenced to determine the exact nature of the DNA sequence variation. Other approaches based on the detection of mismatches between the two complementary DNA strands include clamped denaturing gel electrophoresis (CDGE), heteroduplex analysis (HA) and chemical mismatch cleavage (CMC). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result.

Detection of point mutations may be accomplished by molecular cloning of the mTOR allele(s) and sequencing the allele(s) using techniques well known in the art. Alternatively, the gene sequences can be amplified directly from a genomic DNA preparation from a physiological sample (e.g., comprising cancer cells) obtained from a subject, using known techniques. The DNA sequence of the amplified sequences can then be determined.

There are six well known methods for a more complete, yet still indirect, test for confirming the presence of a mutant allele: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. For allele-specific PCR, primers are used which hybridize at their 3' ends to a particular mTOR mutation. If the particular mutation is not present, an amplification product is not observed. Amplification Refractory Mutation System (ARMS) can also be used. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Other techniques for detecting insertions and deletions as known in the art can be used.

In the first three methods (SSCA, DGGE and RNase protection assay), a new electrophoretic band appears. SSCA detects a band that migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe that is complementary to the mTOR gene coding sequence. The riboprobe and either mRNA or DNA isolated from the tumor tissue are annealed (hybridized) together and subsequently digested with the enzyme RNase A that is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mTOR mRNA or gene but can be a segment of either.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA that might contain a mutation can be amplified using PCR before hybridization.

Nucleic acid analysis via microchip technology is also applicable to the present invention.

DNA sequences of the mTOR gene that have been amplified by use of PCR may also be screened using allele-specific probes. These probes are nucleic acid oligomers, each of which contains a region of the mTOR gene sequence harboring a known mutation. For example, one oligomer may be about 30 nucleotides in length, corresponding to a portion of the mTOR gene sequence. By use of a battery of such allele-specific probes, PCR amplification products can be screened to identify the presence of a previously identified mutation in the mTOR gene. Hybridization of allele-specific probes with amplified mTOR sequences can be performed, for example, on a nylon filter. Hybridization to a particular probe under stringent hybridization conditions indicates the presence of the same mutation in the tissue as in the allele-specific probe.

Alteration of mTOR mRNA expression can be detected by any technique known in the art. These include Northern blot analysis, PCR amplification and RNase protection. Diminished mRNA expression indicates an alteration of the wild-type mTOR gene.

Alteration of wild-type mTOR genes can also be detected by screening for alteration of wild-type mTOR protein, or a portion of the mTOR protein. For example, monoclonal antibodies immunoreactive with mTOR (or to a specific portion of the mTOR protein) can be used to screen a tissue. Lack of cognate antigen would indicate a mutation. Antibodies specific for products of mutant alleles could also be used to detect mutant mTOR gene product. Such immunological assays can be done in any convenient formats known in the art. These include Western blots, immunohistochemical assays and ELISA assays. Any means for detecting an altered mTOR protein can be used to detect alteration of wild-type mTOR genes. Functional assays, such as protein binding determinations, can be used. In addition, assays can be used that detect mTOR biochemical function. Finding a mutant mTOR gene product indicates alteration of a wild-type mTOR gene.

Mutant mTOR genes or gene products can be detected in a variety of physiological samples collected from a subject (e.g., comprising a cancer cell(s)).

Hybridization Methodology

The DNA (or nucleic acid) sample may be contacted with the oligonucleotide probe in any suitable manner known to those skilled in the art. For example, the DNA sample may be solubilized in solution, and contacted with the oligonucleotide probe by solubilizing the oligonucleotide probe in solution with the DNA sample under conditions that permit hybridization. Suitable conditions are well known to those skilled in the art. Alternatively, the DNA sample may be solubilized in solution with the oligonucleotide probe immobilized on a solid support, whereby the DNA sample may be contacted with the oligonucleotide probe by immersing the solid support having the oligonucleotide probe immobilized thereon in the solution containing the DNA sample.

Certain Definitions

The terms "control" or "control sample" refer to any sample appropriate to the detection technique employed.

The control sample may contain the products of the biomarker detection technique employed or the material to be tested. Further, the controls may be positive or negative controls. By way of example, where the biomarker detection technique is PCR amplification, followed by size fractionation, the control sample may comprise DNA fragments of an appropriate size. Likewise, where the biomarker detection technique involves detection of a mutated protein, the control sample may comprise a sample of a mutant protein. However, in certain embodiments, the control sample comprises the material to be tested. However, where the sample to be tested is genomic DNA, the control sample is preferably a highly purified sample of genomic DNA.

A "mutated gene" or "mutation" or "functional mutation" refers to an allelic form of a gene, which is capable of altering the phenotype of a subject having the mutated gene relative to a subject which does not have the mutated gene.

As used herein, the term "specifically hybridizes" or "specifically detects" refers to the ability of a nucleic acid molecule to hybridize to at least approximately six consecutive nucleotides of a sample nucleic acid.

The terms "protein," "peptide" and "polypeptide" are used interchangeably herein.

The invention encompasses isolated or substantially purified nucleic acid molecules. In the context of the present invention, an "isolated" or "purified" DNA molecule is a DNA molecule that, by human intervention, exists apart from its native environment. An isolated DNA molecule may exist in a purified form or may exist in a non-native environment. For example, an "isolated" or "purified" nucleic acid molecule, or portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences and proteins or partial-length proteins encoded thereby are also encompassed by the present invention.

By "fragment" or "portion" of a sequence is meant a full length or less than full length of the nucleotide sequence encoding, or the amino acid sequence of a polypeptide or protein. As it relates to a nucleic acid molecule, sequence or segment of the invention when linked to other sequences for expression, "portion" or "fragment" means a sequence having, for example, at least 80 nucleotides, at least 150 nucleotides, or at least 400 nucleotides. If not employed for expressing, a "portion" or "fragment" means, for example, at least 9, 12, 15, or at least 20, consecutive nucleotides, e.g., probes and primers (oligonucleotides), corresponding to the nucleotide sequence of the nucleic acid molecules of the invention. Alternatively, fragments or portions of a nucleotide sequence that are useful as hybridization probes generally do not encode fragment proteins retaining biological activity. Thus, fragments or portions of a nucleotide sequence may range from at least about 6 nucleotides, about 9, about 12 nucleotides, about 20 nucleotides, about 50 nucleotides, about 100 nucleotides or more.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Synthetic" polynucleotides are those prepared by chemical synthesis.

"Recombinant DNA molecule" is a combination of DNA sequences that are joined together using recombinant DNA technology and procedures used to join together DNA sequences as described, for example, in Sambrook and Russell (2001).

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, such as mTOR, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

A "mutant" mTOR refers to the protein or fragment thereof that is encoded by an mTOR gene having a mutation. Mutations in mTOR may cause resistance to an mTOR kinase inhibitor, such as a mutation leading to a mutant gene product that results in a substitution mutation in mTOR (e.g., L2185A).

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more nucleic acids, polynucleotides or polypeptides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the World Wide Web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by a BLAST program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, or at least 80%, 90%, or even at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%; at least 80%, 81%, 82%, 83%, 84%, 85%, 86%, 87%, 88%, or 89%; or at least 90%, 91%, 92%, 93%, or 94%; or even at least 95%, 96%, 97%, 98% or 99% sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl:

$$T_m\ 81.5°\ C.+16.6(\log M)+0.41(\%\ GC)-0.61(\%\ \text{form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. Guidance as to appropriate amino acid substitutions that do not affect biological activity of the protein of interest are well known in the art. Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally-occurring proteins as well as variations and modified forms thereof.

Individual substitutions deletions or additions that alter, add or delete a single amino acid or a small percentage of amino acids (typically less than 5%, more typically less than 1%) in an encoded sequence are "conservatively modified variations."

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms."

A "host cell" is a cell which has been transformed, or is capable of transformation, by an exogenous nucleic acid molecule. Thus, "transformed," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically includes sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will have the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source.

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified through, for example, the use of single-stranded mutagenesis. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Genome" refers to the complete genetic material of an organism.

"Coding sequence" refers to a DNA or RNA sequence that codes for a specific amino acid sequence and excludes the non-coding sequences. For example, a DNA "coding sequence" or a "sequence encoding" a particular polypeptide, is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence. It may constitute an "uninterrupted coding sequence," i.e., lacking an intron, such as in a cDNA or it may include one or more introns bounded by appropriate splice junctions. An "intron" is a sequence of RNA that is contained in the primary transcript but that is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

The term "regulatory sequence" is art-recognized and intended to include promoters, enhancers and other expression control elements (e.g., polyadenylation signals). Such regulatory sequences are known to those skilled in the art. It should be understood that the design of the expression vector may depend on such factors as the choice of the host cell to be transfected and/or the amount of fusion protein to be expressed.

The term DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

A control element, such as a promoter, "directs the transcription" of a coding sequence in a cell when RNA polymerase binds the promoter and transcribes the coding sequence into mRNA, which is then translated into the polypeptide encoded by the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones having a population of daughter cells containing the exogenous DNA.

"Operably-linked" refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" or "translation stop codon" or "stop codon" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. The change of at least one nucleotide in a nucleic acid sequence can result in an interruption of the coding sequence of the gene, e.g., a premature stop codon.

The terms "cancer" and "cancerous" refer to or describe the physiological condition in mammals that is typically characterized by unregulated cell growth and proliferation. Examples of cancer include, but are not limited to, carcinoma, lymphoma (e.g., Hodgkin's and non-Hodgkin's lymphoma), blastoma, sarcoma, and leukemia. More particular examples of cancers include squamous cell cancer, small-cell lung cancer, non-small cell lung cancer, adenocarcinoma of the lung, squamous carcinoma of the lung, cancer of the peritoneum, hepatocellular cancer, renal cell carcinoma, gastrointestinal cancer, gastric cancer, esophageal cancer, pancreatic cancer, glioma, cervical cancer, ovarian cancer, liver cancer, bladder cancer, hepatoma, breast cancer (e.g., endocrine resistant breast cancer), colon cancer, rectal cancer, lung cancer, endometrial or uterine carcinoma, salivary gland carcinoma, kidney cancer, liver cancer, prostate cancer, vulval cancer, thyroid cancer, hepatic carcinoma, melanoma, leukemia and other lymphoproliferative disorders, and various types of head and neck cancer.

The phrase "effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The invention will now be illustrated by the following non-limiting Example.

Example 1

Summary

Protein kinases are therapeutic targets for human cancer. However, "gatekeeper" mutations in tyrosine kinases cause acquired clinical resistance, limiting long-term treatment benefits. mTOR is a key cancer driver and drug target. Numerous small molecule mTOR kinase inhibitors have been developed, with some already in human clinical trials. Given our clinical experience with targeted therapeutics, acquired drug resistance in mTOR is thought likely but not yet documented. Herein, we describe identification of a hotspot (L2185) for drug-resistant mutations, which is distinct from the "gatekeeper" site, and a chemical scaffold refractory to drug-resistant mutations. We also provide new insights into mTOR kinase structure and function. The hotspot mutations are potentially useful as surrogate biomarkers for acquired drug resistance in ongoing clinical trials and future treatments, and to facilitate design of the next generation of mTOR-targeted drugs. Our study provides a foundation for further research on mTOR kinase function and targeting.

Introduction mTOR is a highly conserved serine/threonine protein kinase belonging to the PI3K-related kinase (PIKK) family (Wullschleger, et al. (2006). Cell 124, 471-484). mTOR forms two distinct kinase complexes, mTORC1 and mTORC2. mTORC1 controls cell growth and metabolism, in response to diverse cellular signals, including nutrients, growth factors and cytokines (Ma, X., and Blenis, J. (2009). Nat Rev Mol Cell Biol 10, 307-318). mTORC2 phosphorylates AKT at Ser473 and promotes cell survival (Sarbassov, et al. (2005). Science 307, 1098-1101). Recent advances in cancer genomic sequencing have revealed cancer mutations frequently target mTOR pathway, resulting in hyperactivation of mTOR signaling that drives uncontrolled cancer growth, metabolism and survival (Wood, et al. (2007). Science 318, 1108-1113). mTOR is an established molecular target for cancer therapy, because cancer cells tend to be addicted to aberrant mTOR signaling and mTOR inhibition is well tolerated (Bjornsti, M.-A., and Houghton, P. J. (2004). Nat Rev Cancer 4, 335-348; Guertin, D., and Sabatini, D. (2007). Cancer Cell 12, 9-22; Tsang, et al. (2007). Drug Discov Today 12, 112-124).

Rapamycin is a macrolide natural product and a highly specific mTOR inhibitor. It forms a complex with FKBP12, which binds to the FRB domain of mTOR (Chen, et al. (1995). PNAS 92, 4947-4951; Zheng, et al. (1995). Cell 82, 121-130). Two rapamycin analogs (rapalogs), temsirolimus and everolimus, are FDA-approved drugs for treatment of advanced renal cell and mammary carcinomas. However, rapamycin only partially inhibits TOR functions (Zheng, et al. (1995). Cell 82, 121-130), which is due to selective binding of FKBP12-rapamycin complex to mTORC1, but not mTORC2 (Loewith, et al. (2002). Mol Cell 10, 457-468). Moreover, the clinical efficacy of rapalogs is limited with low overall objective response (Zhang, et al. (2011b). Ann Surg Oncol 18, 580-588). Another shortcoming of rapalogs is that they lead to activation of the IRS1-PI3K-Akt negative feedback loop, sustaining survival of rapalog-treated cancer cells (O'Reilly, et al. (2006). Cancer research 66, 1500-1508; Sun, et al. (2005). Cancer research 65, 7052-7058). For these reasons, it is increasingly recognized that the therapeutic potential of rapalogs are limited.

The clinical success of ATP-competitive tyrosine kinase inhibitors (TKIs), such as imatinib and gefitinib, illustrates the value of targeting kinases as an effective anti-cancer strategy (Zhang, et al. (2009). Nature reviews Cancer 9, 28-39). We previously found that mTOR kinase domain is required for both rapamycin-sensitive and rapamycin-insensitive aspects of cell growth and survival (Zheng, et al. (1995). Cell 82, 121-130), suggesting that TOR kinase domain is a more potent site for mTOR targeting. Subsequent studies lent support to this notion and revealed that the rapamycin-insensitive function is mTORC2-related (Loewith, et al. (2002). Mol Cell 10, 457-468; Sarbassov, et al. (2004). Curr Biol 14, 1296-1302). These findings provide a key rationale for developing ATP-competitive mTOR inhibitors for cancer therapy (Feldman, et al. (2009). PLoS biology 7, e38; Guertin, D. A., and Sabatini, D. M. (2009). Sci Signal 2, pe24; Thoreen, et al. (2009). J Biol Chem 284, 8023-8032). In addition to selective mTOR kinase inhibitors such as PP242, OSI-027 and WYE-354, dual mTOR/PI3K inhibitors such as BEZ235 and Torin2 have been developed, which have additional advantage of preventing activation of the IRS1-PI3K-AKT negative feedback loop. Indeed, mTOR kinase inhibitors display superior anti-tumor effects compared with rapalogs in preclinical cancer models and are well tolerated with excellent toxicological profiles (Zhang, et al. (2011a). Drug Discov Today 16, 325-331).

Since mTOR kinase inhibitors were described in 2008, numerous mTOR kinase targeting agents have been developed and entered into human clinical trials for cancer treatment (Zhang, et al. (2011a). Drug Discov Today 16, 325-331). The remarkable speed with which human clinical trials have been initiated and the sheer number of different compounds being tested in patients underscore their therapeutic potential. Despite early promising results, major challenges remain. A comprehensive, mechanistic understanding of these small molecule inhibitors is lacking. Previous clinical experience with BCR-ABL and EGFR small molecule inhibitors shows that binding site drug-resistant mutations represent a major limiting factor for clinical efficacy (Zhang, et al. (2009). Nature reviews Cancer 9, 28-39). In vitro mutagenesis screens have identified resistance mutations in ABL and EGFR kinases that faithfully recapitulate clinical observations (Azam, et al. (2003). Cell 112, 831-843; Engelman, et al. (2006). The Journal of clinical investigation 116, 2695-2706). The present study is aimed at developing a simple method and applying it to understand mTOR kinase function and drug-resistant mutations.

Results

A *S. cerevisiae* System for Studying Chemical Inhibition of mTOR Kinase

TOR is structurally and functionally conserved between humans and yeast. However, among a large panel of structurally diverse mTOR kinase inhibitors, only Torin2, and to a lesser degree, BEZ235, inhibit yeast growth (FIGS. 1A and 8), which is consistent an earlier observation (Liu, et al. (2012). ACS chemical biology 7, 982-987). Poor sensitivity to mTOR inhibitors could be due to low permeability of yeast cells or insensitivity of yeast TOR kinase to these particular small molecules. To distinguish the two possibilities, we engineered a TOR2-mTOR fusion in which yeast TOR2 kinase domain is swapped in frame with mTOR kinase domain (FIG. 1B). When expressed under the control of the TOR2 native promoter in a centromeric plasmid (FIG. 1C), TOR2-mTOR fusion gene suppresses the temperature sensitivity of tor2-dg strain (FIGS. 1D and 1E), which carries a genomic TOR2 gene fused with degron, a tag rendering heat-inducible degradation of tagged proteins (Dohmen, R. J., and Varshavsky, A. (2005). Heat-Inducible Degron and the Making of Conditional Mutants. In Methods in Enzymology, J. D. Raymond, ed. (Academic Press), pp. 799-822), indicating that mTOR kinase domain complements the essential function of TOR2 kinase in yeast.

We next tested sensitivity of tort-dg cells expressing TOR2-mTOR to mTOR kinase inhibitors. Similar to wild type (WT) cells, tort-dg cells expressing TOR2 are poorly inhibited by mTOR kinase inhibitors BEZ235 and OSI-027 (FIG. 1E). In contrast, tort-dg strain expressing TOR2-mTOR is highly sensitive to these drugs (FIG. 1E). This observation indicates that TOR2 is intrinsically resistant to mTOR kinase inhibitors, and that swapping TOR2 kinase domain with mTOR kinase domain renders yeast sensitivity to mTOR inhibitors.

Even with TOR2-mTOR, tort-dg strain remains resistant to majority of mTOR kinase inhibitors (FIG. 2A). Yeast is known to be poorly permeable to small drug molecules (Emter, et al. (2002). FEBS Letters 521, 57-61; Simon, J. A., and Bedalov, A. (2004). Nature reviews Cancer 4, 481-492). Deletion of ERG6, PDR1, and PDR3 has been used to enhance yeast cell permeability to organic compounds (Gray, et al. (1998). Science 281, 533-538). However, yeast cells do not appear to tolerate erg6Δ in the tort-dg background (data not shown). To explore an alternative method, we tested three different classes of antifungal drugs known to disrupt yeast cell wall or membrane structures. Amphotericin B, an amphipathic molecule that forms channel-like structures in the fungal membrane (Ghannoum, M. A., and Rice, L. B. (1999). Clinical Microbiology Reviews 12, 501-517), increases yeast sensitivity to most of mTOR kinase inhibitors (FIG. 2A). In contrast, miconazole and caspofungin, antifungal drugs that disrupt ergosterol-containing yeast membrane and cell wall, respectively, fail to do so (FIGS. 2B and 2C). Amphotericin B was used thereafter to facilitate our studies of mTOR kinase inhibitors in yeast.

Mutational Analysis of 'Gatekeeper' Residue in mTOR Kinase

Non-small cell lung cancer (NSCLC) patients responding to initial erlotinib treatment typically relapse within six months. In 50% cases. it is due to a single missense mutation, T790M, at the gatekeeper site of EGFR (Bell, et al. (2005). Nat Genet 37, 1315-1316; Kobayashi, et al. (2005). New England Journal of Medicine 352, 786-792; Pao, et al. (2005). PLoS Med 2, e73). The larger methionine at this position constrains erlotinib binding, causing, drug resistance while retaining the kinase's catalytic activity. A similar gatekeeper mutation (T315I) in the ABL kinase domain renders resistance of chronic myeloid leukemia (CML) to imatinib (Gone, et al. (2001). Science (New York, N.Y.) 293, 876-880). These observations suggest the gatekeeper residue contributes to resistance to ATP-competitive kinase inhibitors.

Based on sequence alignment, the mTOR gatekeeper residue is predicted to be I2237 (Sturgill, T. W., and Hall, M. N. (2009). ACS chemical biology 4, 999-1015). It is located within the hydrophobic pocket of N-lobe of the kinase domain (FIGS. 3A, 9 and 3B). In contrast to the conserved threonine gatekeeper residue in tyrosine kinases, both mTOR and PI3Kα have a relatively bulky isoleucine at this position (FIG. 3A) (Vogt, P. K. (2008). Cancer Cell 14, 107-108; Zunder, et al. (2008). Cancer cell 14, 180-192). To evaluate the significance of the gatekeeper site, we performed saturation mutagenesis of I2237 in TOR2-mTOR fusion. Resulting TOR2-mTOR mutants were assayed for their sensitivity to chemically diverse mTOR kinase inhibitors. However, none of the mutations exhibit discernible drug resistance (FIG. 3C). Strikingly, only the I2237L mutation fully preserves mTOR kinase function (FIGS. 3D and 3E), suggesting that mTOR's gatekeeper position does not tolerate any substitution except the highly conserved leucine, which explains the lack of drug resistant gatekeeper mutations. A similar phenomenon was also observed with another atypical kinase, PI3Kα (Zunder, et al. (2008). Cancer cell 14, 180-192), suggesting that mTOR and PI3K are similar with respect to the function of the gatekeeper residue.

Identification of a Non-Gatekeeper Hotspot for Drug-Resistant Mutations in mTOR Kinase Domain Yeast is a powerful model organism for genetic screens. We employed our yeast system and the following strategy to identify drug resistant mutations in mTOR kinase domain (FIG. 4A). In this scheme, mTOR kinase mutants are generated through error-prone PCR amplification, and are recombined with a gapped TOR2 plasmid by 'gap-repair' to create TOR2-mTOR fusions in frame through homologous recombination in yeast cells. 'Gap-repair' is an efficient method to generate a library of mutant clones (Martzen, et al. (1999). Science 286, 1153-1155; Uetz, et al. (2000). Nature 403, 623-627). TOR2-mTOR mutants are then replica-plated onto OSI-027-containing plates to screen for drug resistant mutations, which leads to isolation of drug-resistant clones carrying L2185A and L2185C mutations. Interestingly, these mutations also confer resistance to AZD8055, INK128, and PF-04691502 (FIG. 4B), suggesting that L2185 is important for binding of structurally diverse mTOR kinase inhibitors.

To systematically evaluate mutational effect at this position, we performed saturation mutagenesis of L2185 and systematically investigated for the potential of each point mutation to confer drug resistance (FIG. 4C). The result shows that L2185A and L2185C are the most important mutations, conferring resistance to OSI-027, AZD8055, INK128, PF-04691502, and PKI-587. In addition, L2185D and L2185N are moderately resistant to AZD8055, PF-04691502, and PKI-587; and L2185G to AZD8055, INK128, PF-04691502, and PKI-587. The differential effect of L2185 mutations on different mTOR kinase inhibitors likely reflects structural diversity of the tested compounds and distinct requirements at position 2185. Of note, L2185A and L2185C mutants remain sensitive to BEZ235 and Torin2, two compounds with closely related chemical structures, suggesting that a common structural scaffold(s) renders these agents less susceptible to the binding site mutations.

L2185A Mutation Confers Drug-Resistance in Colorectal and Lung Cancers

To evaluate drug-resistant mutations identified with our yeast system in human cancer models, we transiently expressed Flag-mTOR(L2185A) in HEK293T cells and found that it confers resistance to OSI-027 and INK128 (FIG. 10A). To test the significance of our findings in more physiologically relevant cancer models, we used the CRISPR/Cas9 genome editing technology (Cong, et al. (2013). Science (New York, N.Y.) 339, 819-823; Mali, et al. (2013). Science (New York, N.Y.) 339, 823-826) to integrate L2185A into the mTOR locus of SW480 colorectal and H460 lung cancer cell lines (FIG. 10B), representing cancer types with high mortality rates due to lack of efficacious targeted therapy. L2185A mutation indeed confers resistance to AZD8055, INK128, OSI-027, and PP242 in SW480 colorectal cancer cells (FIGS. 5A and 5B), which is accompanied by drug-resistant signaling by both mTORC1 and mTORC2 (FIG. 5C). Independent mutant clones provide essentially the same phenotype (FIG. 10C), indicating that off target effect is unlikely. Interestingly, we did not observe significant differences in drug resistance between heterozygous and homozygous mutants (FIGS. 10C and 10D), suggesting that the mutant allele is dominant. Notably, AKT (S473) phosphorylation is moderately more drug-resistant than S6K1(T389) phosphorylation in mTOR(L2185A) versus WT cells (FIG. 5C), suggesting that L2185A mutation differentially affects drug-binding in two different mTOR complexes. Comparable results were obtained with H460 lung cancer cells with select compounds (FIGS. 10E and 10F), suggesting that drug-resistance by L2185A is not tumor type-specific.

As seen in yeast, the L2185A mutant remains sensitive to BEZ235 and Torin2 in colorectal and lung cancer cells (FIGS. 5D and 10G). Curiously, although L2185A confers resistance to PF-04691502 in the yeast assay (FIG. 4B), SW480 cells carrying this mutation are still sensitive to PF-04691502 (FIG. 5G). Because PF-04691502 is an mTOR/PI3K dual inhibitor, the discrepancy between yeast and human cells may be attributed to inhibition of type I PI3Ks in colorectal cancer cells by PF-04691502, which is absent from yeast. To determine whether L2185A renders drug resistance in vivo, we generated xenograft tumors derived from SW480 cells carrying WT or L2185A mutant mTOR. When delivered via intraperitoneal injection, INK128 strongly attenuates growth of WT mTOR tumors, but has little or no effect on mTOR(L2185A) bearing tumors (FIGS. 6A-D). Similarly, L2185A renders xenograft tumors drug-resistance in mTORC1 and mTORC2 signaling in xenograft tumors, which is in contrast to the complete blockadge of mTOR signaling in WT mTOR tumors (FIG.

6F). Together, these results demonstrate that L2185A confers drug resistance in vitro and in vivo.

Mutational Analysis of Conserved Hydrophobic Pocket

'Hydrophobic spines' within the active site are increasingly recognized to the binding of ATP and ATP-competitive inhibitors of protein kinases (Kornev, et al. (2006). Proceedings of the National Academy of Sciences of the United States of America 103, 17783-17788). The recently published crystal structure of mTOR kinase domain provides a detailed three-dimensional view of mTOR's ATP-binding site (Yang, et al. (2013). Nature 497, 217-223). Several residues, including I2163, L2185, Y2225, I2237 and W2239, are highly conserved in PI3K and PI3K-related kinases (FIG. 9). They appear to form an N-lobe-like hydrophobic pocket involved in binding of ATP and ATP-competitive mTOR inhibitors (FIG. 7A). To understand their significance, we systematically mutated them and determined the effect of the substitutions with the yeast growth assay (FIG. 7B). Most of the mutations cause loss of mTOR catalytic activity to different degrees, with only 10-35% retaining normal mTOR kinase function (FIG. 7C). Interestingly, over 50% hydrophobic substitutions retain normal mTOR function (FIG. 7D). Notably I2237 can only tolerate hydrophobic substitutions, underscoring the importance of this hydrophobic environment.

To verify our yeast-based results, several loss-of-function mTOR mutants (FIG. 7E) were expressed as Flag-tagged proteins in HEK293T cells and assayed for kinase activity in vitro using recombinant 4E-BP1 as a substrate (FIG. 7F). Severe loss of kinase activity was confirmed, validating the yeast results. Hydrophobic interactions are known to be important for binding of ATP and TKIs in the ATP-binding pockets of protein tyrosine kinases (Zhang, et al. (2009). Nature reviews Cancer 9, 28-39). Our results demonstrate that the hydrophobic environment of the ATP-binding pocket is also critical for catalytic function of mTOR, an atypical protein serine/threonine kinase.

Discussion

Small molecule kinase inhibitors are proven clinically effective against malignancies in which kinase targets are hyper-activated, driving uncontrolled growth and proliferation. However, tumors typically develop drug resistance within six months after initial treatment. A major mechanism underpinning acquired resistance to kinase inhibitors is binding site mutations (Gorre, et al. (2001). Science (New York, N.Y.) 293, 876-880; Heinrich, et al. (2003). Journal of clinical oncology: official journal of the American Society of Clinical Oncology 21, 4342-4349; Kobayashi, et al. (2005). New England Journal of Medicine 352, 786-792). Thus, identification of resistant mutations is crucial for clinical diagnosis and development of new strategies to overcome resistant variants. To this end, we have developed a robust yeast tool to screen and study drug-resistant mutations in mTOR kinase domain. By simply measuring yeast growth, it enables the identification and analysis of residues in mTOR kinase domain crucial for mTOR functions and drug-resistance.

Unlike subjectian cells, yeast cells are poorly permeable to small molecules due to the unique cell wall and plasma membrane structures, which has been a major barrier for using yeast for drug research and screens (Emter, et al. (2002). FEBS Letters 521, 57-61; Simon, J. A., and Bedalov, A. (2004). Nature reviews Cancer 4, 481-492). Yeast strains with deletion of ERG6 (alteration in membrane composition by inhibiting ergosterol biosynthesis), PDR1, and PDR3

(decrease in drug efflux) have been developed to improve drug permeability (Dunstan, et al. (2002). Journal of the National Cancer Institute 94, 88-94). However, the major drawback of erg6∆ strain is dramatically decreased plasmid transformation efficiency and sexual conjugation, which limit yeast as a useful tool for drug screening (Gaber, et al. (1989). Molecular and cellular biology 9, 3447-3456). Here we found that the antifungal drug amphotericin B can enhance cell permeability to structurally diverse mTOR kinase inhibitors. Curiously, although miconazole, a potent inhibitor of ergosterol biosynthesis, fails to enhance drug sensitivity, suggesting that targeting this lipid pathway alone is an ineffective strategy. It will be interesting to determine if amphotericin B is broadly useful for different classes of small molecules, which could significantly expand the role of yeast as a general tool for drug discovery.

Gatekeeper residues are common locations for acquisition of TKI drug-resistance. Unlike most protein kinases that have a bulky gatekeeper residue (e.g., methionine), more than 40% tyrosine kinases utilize a threonine at this position. The presence of a small gatekeeper residue in the tyrosine kinases appears to make them more amenable to regulation. In PI3Ks and PIKKs, the gatekeeper is a bulky isoleucine residue (except for leucine in ATM). The presumptive mTOR gatekeeper residue, I2237, is located in the N-lobe hydrophobic pocket, where it is thought to engage in hydrophobic interaction with the adenine moiety of ATP. Strikingly, only substitution with leucine, methionine, or valine is tolerated at this position. Any other substitution causes a severe loss in mTOR kinase function. A similar phenomenon was observed with the isoleucine gatekeeper residue (I848) in p110-PI3Kα (Vogt, P. K. (2008). Cancer Cell 14, 107-108; Zunder, et al. (2008). Cancer cell 14, 180-192). Thus, the relatively bulky gatekeeper residue and the importance of gatekeeper residue in maintaining the hydrophobic pocket almost certainly limit its contribution to drug resistance in mTOR and PI3Kα.

The drug-resistant mutation hotspot L2185 is also part of N-lobe hydrophobic pocket. Because L2185 is further away from ATP than I2237, it appears more tolerant to substitution by smaller hydrophobic residues (e.g., alanine and cysteine), while creating an incipient cavity in the active site that destabilizes binding of mTOR inhibitors (e.g., AZD8055, INK128, OSI-027, and PP242) via loss of van der Waals contact(s) (FIGS. 11A and 11B). Therefore, unlike gatekeeper mutations in tyrosine kinases, where substitution of the smaller residue to a bulkier side chain constrains drug binding (Taylor, S. S., and Kornev, A. P. (2011). Trends in biochemical sciences 36, 65-77), mutation of L2185 of mTOR to a smaller residue such as alanine results in drug resistance by weakening drug binding.

It is remarkable that mutation of L2185 does not confer resistance to either Torin2 or BEZ235, both of which have three-ring fused heterocyclic structure. The distance between L2185 and the adenine-like tricyclic ring of Torin2 (3.9 Å) is farther away than PP242 (3.4 Å) (FIG. 11C). Because hydrophobic interaction strength decreases rapidly with increasing separation, L2185 would appear to play a less significant role in stabilizing binding of Torin2 versus PP242. Thus, substitution of leucine with an alanine has less impact on Torin2 binding (as opposed to PP242). The tricyclic Torin2 ring is thought to stack with W2239 of mTOR and stabilize the drug binding (Yang, et al. (2013). Nature 497, 217-223). Such a stacking interaction may, therefore, mitigate any decrease in productive hydrophobic interactions caused by L2185 mutations and maintain the sensitivity of either Torin2 or BEZ235. This observation suggests that incorporation of chemotypes isostructural to the tricyclic ring of Torin2 would be advantageous in minimizing acquired drug resistance. Knowledge of "gatekeeper" mutations has aided discovery of second generation TKIs, such as bafetinib and dastinib, which appear less susceptible to drug-resistant mutations (Santos, et al. (2010). Curr Opin Investig Drugs 11, 1450-1465; Tokarski, et al. (2006). Cancer Research 66, 5790-5797). Moreover, such inhibitors should be reserved for only L2185 mutant tumors. Our characterization of L2185 mutations may be useful in improving the design of mTOR kinase inhibitors and treatment strategy.

In addition to identifying drug-resistant mutations, our yeast system is useful for probing the structure and function of mTOR kinase domain. In a typical protein kinase catalytic domain, there are two hydrophobic pockets inside the active site critical for adenine binding (Liu, Y., and Gray, N. S. (2006). Nature chemical biology 2, 358-364). We found that a cluster of conserved hydrophobic residues in the N-lobe is critical for maintaining mTOR kinase function. In a previous study of Protein Kinase A (PKA) also in a S. cerevisiae system, most residues within the ATP binding pocket of PKA were tolerant to mutations (Kennedy, et al. (2009). PloS one 4, e4746). In contrast, the data herein show that mutation of conserved hydrophobic residues in mTOR active site is not well-tolerated, and caused substantial loss of catalytic function (FIG. 7C). These distinctions likely reflect evolutionary differences in kinase regulation between atypical protein kinases (e.g. mTOR), and the canonical protein kinases (e.g., PKA).

Conserved residues of the hydrophobic core of the PKA catalytic domain have been extensively characterized by Taylor and co-workers (Kornev, et al. (2006). Proceedings of the National Academy of Sciences of the United States of America 103, 17783-17788; Meharena, et al. (2013). PLoS biology 11, e1001680; Taylor, S. S., and Kornev, A. P. (2011). Trends in biochemical sciences 36, 65-77). Three-dimensional alignment of the structures of PKA (PDB ID code 1 ATP) and mTOR (4JSP) permitted presumptive identification of mTOR residues corresponding to the R- and C-Spines of PKA (FIGS. 11D and 11E). Our structural alignment documents that mTOR residues 12163 and L2185 (both characterized herein) correspond to PKA C-Spine residues V57 and A70, respectively (FIGS. 11D and 4E). We suggest, therefore, that mutation of either 12163 or L2185 impairs mTOR catalytic activity by disrupting the structure of the C-Spine of this atypical protein kinase. In PKA, three "Shell" residues [V104 (Sh1), M120 (Sh2), and M118 (Sh3)] stabilize the structure of the R-Spine (Meharena, et al. (2013). PLoS biology 11, e1001680). Within mTOR, these three residues correspond to Y2225 (Sh1), I2237 (Sh2), and G2235 (Sh3). Lack of conservation of these "Shell" resides between PKA and mTOR suggests that the R-spine of mTOR may not be as dynamic as its counterpart in PKA. The latter might fill the adenine pocket and prevent binding of ATP. It is also interesting to note that similar to RAF kinase, the equivalents of I2163 and L2185 can tolerate smaller hydrophobic residues but not phenylalanine (Hu, et al. (2013). Cell 154, 1036-1046; Hu, et al. (2011). Proceedings of the National Academy of Sciences of the United States of America 108, 6067-6072; Shaw, et al. (2014). Molecular and cellular biology 34, 1538-1546). Phenylalanine might fill the adenine pocket and prevent binding of ATP. Finally, the salt bridge between the C- and R-Spines [E91(OE2)-K72(NZ)=3.6 Å] in PKA corresponds to an analogous salt bridge in mTOR [E2190(OE1)-K2187(NZ) =2.8 Å] (FIG. 11F), which could control the catalytic activity as well as bridge the two spines as seen with PKA (Taylor, S. S., and Kornev, A. P. (2011). Trends in biochemical sciences 36, 65-77). While the importance of hydrophobic environment and hydrophobic structures are well studied in the canonical protein kinases, it is much less well understood in the atypical kinase such as mTOR. It would be of considerable interest to elucidate the function of hydrophobic residues in mTOR, which could help improve future design of mTOR kinase inhibitors.

The findings described herein can impact the field in several ways. First, the drug-resistant mutation profiles could provide guidance for monitoring the potential occurrence of drug-resistant mutations during human clinical trials. Second, our study provides valuable insights into the structure-function relationship of mTOR kinase. It provides insights into the mechanism of action for mTOR kinase inhibitors and drug resistance, which can help with design of future mTOR inhibitors. Finally, Drug-resistant mTOR mutants can be powerful tools for probing the physiological functions of mTOR kinase, as does the rapamycin-resistant mTOR mutants that have made much contributions to understanding of mTORC1.

Experimental Procedures

Plasmids, Mutagenesis and Library Screen

The TOR2-mTOR hybrid plasmid was constructed by replacing the C-terminal region of TOR2 of pML40-TOR2 (Alarcon, et al. (1996). Genes & development 10, 279-288) (encoding for 2080-2474 aa) in frame with a DNA fragment corresponding to C-terminal domain of mTOR (encoding for 2140-2549 aa). To construct mutant TOR2-mTOR plasmids, mTOR C-terminal region was amplified by PCR and co-transformed into yeast with XmaI-digested pML40-TOR2 plasmid that excised the TOR2 C-terminal region. The resultant TOR2-mTOR fusion plasmids are constructed in reading frame by gap-repair in yeast.

The wild type and kinase-dead pCDNA3-Flag-mTOR plasmids were obtained from Addgene. The I2163K, L2185A, L2185C, L2185P and I2237S mutant plasmids were constructed by using overlap extension-PCR method for site-directed mutagenesis. For site-specific saturation mutagenesis, pUC18-mTOR kinase plasmid was constructed by insertion of mTOR C-terminal domain (aa 2140-2549) into pUC18 vector at the XmaI site. The pUC18-mTOR plasmid was mutagenized at the I2163, L2185, Y2225, I2237 and W2239 residues by degenerate PCR with NNK primers. The mutation library was constructed using QuikChange mutagenesis kit according to the manufacture's instruction (Agilent) and transformed into chemically competent E. coli. Plasmid DNA was extracted by miniprep kit (Promega) and the mutations were verified by sequencing.

Yeast Strains and Culture and Growth Assays

The tor2-dg temperature-sensitive strain was generated from the W303 background (MATa leu2-3, 112 trp1-1 cau1-100 ura3-1 ade2-1 his3-11,15) as described previously (Dohmen, R. J., and Varshavsky, A. (2005). Heat-Inducible Degron and the Making of Conditional Mutants. In Methods in Enzymology, J. D. Raymond, ed. (Academic Press), pp. 799-822). For the halo assay, log phase W303 wild type or tor2-dg cells were spread evenly on YPD agarose plates. After drying, small sterile filter discs were placed on the surface and 5 µl of rapamycin (1 µM), BEZ235 (5 µM), PKI-587 (3 µM), other mTOR inhibitors (10 µM), or DMSO were applied to each disc. Plates were incubated at 30° C. (wild type) or 37° C. (tor2-dg) for 3 day.

To enhance yeast cell permeability, log phase W303 tort-dg cells were spread evenly on SD-Leu agarose plates. After drying, small sterile filter discs were placed on the surface and 5 µl of indicated mTOR inhibitors or DMSO were applied to each disc with or without adding 5 µl of amphotericin B (10 µM), miconazole (50 µM) or caspofungin (50 µM). Plates were incubated at 37° C. for 3 day. Drug resistance profiles of TOR2-mTOR mutant cells were determined by the spotting assay. For this assay, 10-fold serial dilutions of cells were spotted on SD-leu plates in the presence of indicated mTOR inhibitors with or without amphotericin B (200 nM) and incubated at 37° C. for 3 day.

Cancer Cell Lines and CRISPR/Cas9-Mediated Mutagenesis

Cancer cell lines were maintained in DMEM or RPMI 1640, supplemented with 10% fetal bovine serum (Invitrogen) and 1% penicillin/streptomycin (Invitrogen). CRISPR/cas9 technology was used to engineer mutant mTOR allele in SW480 colorectal and H460 lung cancer cells. Briefly, The target sequence for mTOR, GCTGCATCACACGCT-CATCC (SEQ ID NO: 3 was designed through the online tool at crispr.mit.edu, and cloned into pSPCas9(BB)-2A-GFP vector (PX458 in Addgene). Genomic mTOR mutation was engineered using a protocol as described (Ran, et al. (2013). Nature protocols 8, 2281-2308) and was confirmed by targeted sequencing.

Immunological and Chemical Reagents, and Proliferation Assays

Antibodies against tubulin, S6K, phospho-S6K (Thr389), 4E-BP1, phospho-4E-BP1 (Thr37/46), Akt, phospho-Akt (Thr308), and phospho-Akt (Ser473) were purchased from Cell Signaling Technology. For mTOR inhibitors, PI-103, PP242, WYE-354, and WYE-132 were purchased from Chemdea; BEZ235 was purchased from LC Laboratories; XL765, PKI-587, PF-04691504, OSI-027, AZD8055, INK-128 and Torin2 were purchased from Selleck Chemicals. For drug sensitivity test, cancer cells were seeded in 96-well plates at a density of 2,000 cells per well. 24 hours later, different concentrations of mTOR inhibitors were added in quadruplicate. Cell growth was measured by the sulforhodamine B (SRB) assay as previously described (Vichai, V., and Kirtikara, K. (2006). Nature protocols 1, 1112-1116).

In Vitro mTOR Kinase Assay

The mTOR kinase activity was assessed by in vitro kinase assay as described (Sancak, et al. (2007). Molecular cell 25, 903-915). Briefly, pCDNA3-Flag-mTOR variants were transfected into HEK293T cells by calcium phosphate transfection. After 48 hrs, cells were washed with ice-cold PBS buffer and lysed with lysis buffer (40 mM HEPES [pH 7.4], 2 mM EDTA, 10 mM pyrophosphate, 10 mM glycerophosphate, 0.3% CHAPS, protease inhibitor cocktail [Roche], phosSTOP [Roche] and 1 mM PMSF [Sigma]). Cell lysates were incubated with anti-Flag M2 antibody (Sigma) for 1.5 hrs, which was followed by 1 hr incubation with Protein A/G PLUS-Agarose (Santa Cruz). The immunoprecipitates were washed twice with washing buffer (40 mM HEPES [pH 7.4], 150 mM NaCl, 2 mM EDTA, 10 mM pyrophosphate, 10 mM glycerophosphate, 0.3% CHAPS) and three times with IP buffer (25 mM HEPES [pH 7.4], 20 mM KCl). Kinase assay was performed in 15 µl kinase buffer (25 mM HEPES [pH 7.4], 50 mM KCl, 10 mM $MgCl_2$, 250 µM ATP) containing 150 ng of GST-4E-BP1 for 20 min at 30° C. The kinase reaction was stopped by adding 30 µl 2-fold SDS sample buffer and incubated at 95° C. for 5 min. Phosphorylation of 4E-BP1 was analyzed by Western blot.

Xenograft Tumor Models

Female athymic NCr-nu/nu mice (4-6 weeks old) were obtained from Taconic Farms. They were injected subcutaneously into the left flank with $2\times10^6$ SW480 wild type or mutant cells to establish xenograft tumors. 3 day after injection, mice were randomly divided into 3 groups (8 animals per group). Group 1 was given 1 mg/kg INK128; group 2 was given 0.3 mg/kg INK128, and group 3 was given the vehicle used for administration (vehicle control, VC). INK128 was used according to previous studies, which were at much lower doses than the reported maximum tolerated doses (Gild, et al. (2013). Endocrine-Related Cancer 20, 659-667; Hayman, et al., (2014). Clinical Cancer Research 20, 110-119; Hsieh, et al. (2012). Nature 485, 55-61). INK128 was administered once daily via intraperitoneal injection (i.p.) with freshly prepared drug solution in 100 μl of PBS (final DMSO concentration=0.33%) just before administration. Bidimensional tumor measurements were taken every 2 day and mice were weighed once weekly. Tumor volume was calculated by the following formula: tumor volume $(mm^3)$=(shorter diameter$^2$× longer diameter)/2 and are presented as means±SD (n=8) (Zhang, Y., and Zheng, X. (2012). Cell Cycle 11, 594-603). For analysis of signaling inhibition, tumor tissues were removed from the animals after administration of the last dose of drug, and immediately frozen in liquid nitrogen. Tissue extracts were prepared for analysis of mTOR signaling by Western blot. The animal studies were approved by Rutgers University Institutional Animal Care and Use Committee, and carried out in strict accordance with the recommendations in the Guide for the Care and Use of Laboratory Animals of the National Institutes of Health.

Modeling of L2185A mTOR Kinase Domain

An atomic model of the L2185A mutant form of the mTOR kinase domain was generated via deletion of the Cγ, Cδ1, and Cδ2 atoms of residue 2185. Intratomic distances between the Cβ atom of the modeled mutant enzyme and PP242, Torin, and ATP were estimated directly by assuming that the position of the bound ligand was unaffected by the mutation.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of treating cancer in a subject comprising:
   a) detecting the presence or absence of a biomarker in a physiological sample obtained from the subject, wherein the sample comprises a cancer cell(s), and wherein the biomarker comprises 1) at least one mutation in a mTOR polynucleotide that results in an amino acid substitution at residue L2185 of the mTOR polypeptide; or 2) a mutation at residue L2185 of a mTOR polypeptide;
   b) selecting an mTOR kinase inhibitor having a three-ring fused heterocyclic structure for administration to the subject if the presence of the biomarker is detected; and selecting an mTOR kinase inhibitor without a three-ring fused heterocyclic structure for administration to the subject if the absence of the biomarker is detected; and
   c) administering the selected mTOR kinase inhibitor to the subject to treat the cancer.

2. The method of claim 1, wherein the presence of the biomarker is detected and an mTOR kinase inhibitor having a three-ring fused heterocyclic structure is selected for administration to the subject.

3. The method of claim 2, wherein the mTOR kinase inhibitor having a three-ring fused heterocyclic structure is BEZ235, Torin2, or derivatives thereof.

4. The method of claim 1, wherein the absence of the biomarker is detected and an mTOR kinase inhibitor without a three-ring fused heterocyclic structure is selected for administration to the subject.

5. The method of claim 4, wherein the mTOR kinase inhibitor without a three-ring fused heterocyclic structure is OSI-027, AZD8055, INK128, PF-04691502, PKI-587, PP242 or derivatives thereof.

6. The method of claim 1, wherein the amino acid substitution/mutation is selected from L2185A, L2185C, L2185D, L2185N and L2185G.

7. The method of claim 1, wherein the cancer is colorectal cancer, lung cancer or breast cancer.

8. A method of treating cancer in a subject comprising administering a mTOR kinase inhibitor having a three-ring fused heterocyclic structure to the subject, wherein the cancer was determined to comprise 1) at least one mutation in a mTOR polynucleotide that results in an amino acid substitution at residue L2185 of a mTOR polypeptide; or 2) a mutation at residue L2185 of a mTOR polypeptide.

9. The method of claim 8, wherein the mTOR kinase inhibitor having a three-ring fused heterocyclic structure is BEZ235, Torin2, or derivatives thereof.

10. The method of claim 8, wherein the amino acid substitution/mutation is selected from L2185A, L2185C, L2185D, L2185N and L2185G.

11. The method of claim 8, wherein the cancer is colorectal cancer, lung cancer or breast cancer.

* * * * *

SEQUENCE LISTING

```
<160> NUMBER OF SEQ ID NOS: 17

<210> SEQ ID NO 1
<211> LENGTH: 2549
<212> TYPE: PRT
<213> ORGANISM: Homo sapiens

<400> SEQUENCE: 1

Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205
```

-continued

```
Ala Val Ala Ala Leu Arg Ala Cys Leu Ile Leu Thr Thr Gln Arg Glu
    210                 215                 220
Pro Lys Glu Met Gln Lys Pro Gln Trp Tyr Arg His Thr Phe Glu Glu
225                 230                 235                 240
Ala Glu Lys Gly Phe Asp Glu Thr Leu Ala Lys Glu Lys Gly Met Asn
                245                 250                 255
Arg Asp Asp Arg Ile His Gly Ala Leu Leu Ile Leu Asn Glu Leu Val
                260                 265                 270
Arg Ile Ser Ser Met Glu Gly Glu Arg Leu Arg Glu Glu Met Glu Glu
            275                 280                 285
Ile Thr Gln Gln Gln Leu Val His Asp Lys Tyr Cys Lys Asp Leu Met
    290                 295                 300
Gly Phe Gly Thr Lys Pro Arg His Ile Thr Pro Phe Thr Ser Phe Gln
305                 310                 315                 320
Ala Val Gln Pro Gln Gln Ser Asn Ala Leu Val Gly Leu Leu Gly Tyr
                325                 330                 335
Ser Ser His Gln Gly Leu Met Gly Phe Gly Thr Ser Pro Ser Pro Ala
                340                 345                 350
Lys Ser Thr Leu Val Glu Ser Arg Cys Cys Arg Asp Leu Met Glu Glu
            355                 360                 365
Lys Phe Asp Gln Val Cys Gln Trp Val Leu Lys Cys Arg Asn Ser Lys
    370                 375                 380
Asn Ser Leu Ile Gln Met Thr Ile Leu Asn Leu Leu Pro Arg Leu Ala
385                 390                 395                 400
Ala Phe Arg Pro Ser Ala Phe Thr Asp Thr Gln Tyr Leu Gln Asp Thr
                405                 410                 415
Met Asn His Val Leu Ser Cys Val Lys Lys Glu Lys Glu Arg Thr Ala
                420                 425                 430
Ala Phe Gln Ala Leu Gly Leu Leu Ser Val Ala Val Arg Ser Glu Phe
            435                 440                 445
Lys Val Tyr Leu Pro Arg Val Leu Asp Ile Ile Arg Ala Ala Leu Pro
    450                 455                 460
Pro Lys Asp Phe Ala His Lys Arg Gln Lys Ala Met Gln Val Asp Ala
465                 470                 475                 480
Thr Val Phe Thr Cys Ile Ser Met Leu Ala Arg Ala Met Gly Pro Gly
                485                 490                 495
Ile Gln Gln Asp Ile Lys Glu Leu Leu Glu Pro Met Leu Ala Val Gly
                500                 505                 510
Leu Ser Pro Ala Leu Thr Ala Val Leu Tyr Asp Leu Ser Arg Gln Ile
            515                 520                 525
Pro Gln Leu Lys Lys Asp Ile Gln Asp Gly Leu Leu Lys Met Leu Ser
    530                 535                 540
Leu Val Leu Met His Lys Pro Leu Arg His Pro Gly Met Pro Lys Gly
545                 550                 555                 560
Leu Ala His Gln Leu Ala Ser Pro Gly Leu Thr Thr Leu Pro Glu Ala
                565                 570                 575
Ser Asp Val Gly Ser Ile Thr Leu Ala Leu Arg Thr Leu Gly Ser Phe
                580                 585                 590
Glu Phe Glu Gly His Ser Leu Thr Gln Phe Val Arg His Cys Ala Asp
            595                 600                 605
His Phe Leu Asn Ser Glu His Lys Glu Ile Arg Met Glu Ala Ala Arg
    610                 615                 620
```

```
Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
            645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
            675                 680                 685

Gln Ala Glu Asn Leu Gln Ala Leu Phe Val Ala Leu Asn Asp Gln Val
690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
            725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
            755                 760                 765

Arg Pro Tyr Met Glu Pro Ile Leu Lys Ala Leu Ile Leu Lys Leu Lys
770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
            805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
835                 840                 845

Ala Ser Thr Gly Tyr Val Val Glu Pro Tyr Arg Lys Tyr Pro Thr Leu
850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
            885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
            915                 920                 925

Tyr Ser Thr Ser Glu Met Leu Val Asn Met Gly Asn Leu Pro Leu Asp
930                 935                 940

Glu Phe Tyr Pro Ala Val Ser Met Val Ala Leu Met Arg Ile Phe Arg
945                 950                 955                 960

Asp Gln Ser Leu Ser His His Thr Met Val Val Gln Ala Ile Thr
            965                 970                 975

Phe Ile Phe Lys Ser Leu Gly Leu Lys Cys Val Gln Phe Leu Pro Gln
            980                 985                 990

Val Met Pro Thr Phe Leu Asn Val Ile Arg Val Cys Asp Gly Ala Ile
            995                 1000                1005

Arg Glu Phe Leu Phe Gln Gln Leu Gly Met Leu Val Ser Phe Val
        1010                1015                1020

Lys Ser His Ile Arg Pro Tyr Met Asp Glu Ile Val Thr Leu Met
        1025                1030                1035

Arg Glu Phe Trp Val Met Asn Thr Ser Ile Gln Ser Thr Ile Ile
```

-continued

```
                1040                1045                1050
Leu Leu Ile Glu Gln Ile Val Val Ala Leu Gly Gly Glu Phe Lys
    1055                1060                1065
Leu Tyr Leu Pro Gln Leu Ile Pro His Met Leu Arg Val Phe Met
    1070                1075                1080
His Asp Asn Ser Pro Gly Arg Ile Val Ser Ile Lys Leu Leu Ala
    1085                1090                1095
Ala Ile Gln Leu Phe Gly Ala Asn Leu Asp Asp Tyr Leu His Leu
    1100                1105                1110
Leu Leu Pro Pro Ile Val Lys Leu Phe Asp Ala Pro Glu Ala Pro
    1115                1120                1125
Leu Pro Ser Arg Lys Ala Ala Leu Glu Thr Val Asp Arg Leu Thr
    1130                1135                1140
Glu Ser Leu Asp Phe Thr Asp Tyr Ala Ser Arg Ile Ile His Pro
    1145                1150                1155
Ile Val Arg Thr Leu Asp Gln Ser Pro Glu Leu Arg Ser Thr Ala
    1160                1165                1170
Met Asp Thr Leu Ser Ser Leu Val Phe Gln Leu Gly Lys Lys Tyr
    1175                1180                1185
Gln Ile Phe Ile Pro Met Val Asn Lys Val Leu Val Arg His Arg
    1190                1195                1200
Ile Asn His Gln Arg Tyr Asp Val Leu Ile Cys Arg Ile Val Lys
    1205                1210                1215
Gly Tyr Thr Leu Ala Asp Glu Glu Asp Pro Leu Ile Tyr Gln
    1220                1225                1230
His Arg Met Leu Arg Ser Gly Gln Gly Asp Ala Leu Ala Ser Gly
    1235                1240                1245
Pro Val Glu Thr Gly Pro Met Lys Lys Leu His Val Ser Thr Ile
    1250                1255                1260
Asn Leu Gln Lys Ala Trp Gly Ala Ala Arg Arg Val Ser Lys Asp
    1265                1270                1275
Asp Trp Leu Glu Trp Leu Arg Arg Leu Ser Leu Glu Leu Leu Lys
    1280                1285                1290
Asp Ser Ser Ser Pro Ser Leu Arg Ser Cys Trp Ala Leu Ala Gln
    1295                1300                1305
Ala Tyr Asn Pro Met Ala Arg Asp Leu Phe Asn Ala Ala Phe Val
    1310                1315                1320
Ser Cys Trp Ser Glu Leu Asn Glu Asp Gln Gln Asp Glu Leu Ile
    1325                1330                1335
Arg Ser Ile Glu Leu Ala Leu Thr Ser Gln Asp Ile Ala Glu Val
    1340                1345                1350
Thr Gln Thr Leu Leu Asn Leu Ala Glu Phe Met Glu His Ser Asp
    1355                1360                1365
Lys Gly Pro Leu Pro Leu Arg Asp Asp Asn Gly Ile Val Leu Leu
    1370                1375                1380
Gly Glu Arg Ala Ala Lys Cys Arg Ala Tyr Ala Lys Ala Leu His
    1385                1390                1395
Tyr Lys Glu Leu Glu Phe Gln Lys Gly Pro Thr Pro Ala Ile Leu
    1400                1405                1410
Glu Ser Leu Ile Ser Ile Asn Asn Lys Leu Gln Gln Pro Glu Ala
    1415                1420                1425
Ala Ala Gly Val Leu Glu Tyr Ala Met Lys His Phe Gly Glu Leu
    1430                1435                1440
```

-continued

Glu Ile Gln Ala Thr Trp Tyr Glu Lys Leu His Glu Trp Glu Asp
1445                1450                1455

Ala Leu Val Ala Tyr Asp Lys Lys Met Asp Thr Asn Lys Asp Asp
1460                1465                1470

Pro Glu Leu Met Leu Gly Arg Met Arg Cys Leu Glu Ala Leu Gly
1475                1480                1485

Glu Trp Gly Gln Leu His Gln Gln Cys Cys Glu Lys Trp Thr Leu
1490                1495                1500

Val Asn Asp Glu Thr Gln Ala Lys Met Ala Arg Met Ala Ala Ala
1505                1510                1515

Ala Ala Trp Gly Leu Gly Gln Trp Asp Ser Met Glu Glu Tyr Thr
1520                1525                1530

Cys Met Ile Pro Arg Asp Thr His Asp Gly Ala Phe Tyr Arg Ala
1535                1540                1545

Val Leu Ala Leu His Gln Asp Leu Phe Ser Leu Ala Gln Gln Cys
1550                1555                1560

Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
1580                1585                1590

His Met Leu Ser Glu Leu Glu Glu Val Ile Gln Tyr Lys Leu Val
1595                1600                1605

Pro Glu Arg Arg Glu Ile Ile Arg Gln Ile Trp Trp Glu Arg Leu
1610                1615                1620

Gln Gly Cys Gln Arg Ile Val Glu Asp Trp Gln Lys Ile Leu Met
1625                1630                1635

Val Arg Ser Leu Val Val Ser Pro His Glu Asp Met Arg Thr Trp
1640                1645                1650

Leu Lys Tyr Ala Ser Leu Cys Gly Lys Ser Gly Arg Leu Ala Leu
1655                1660                1665

Ala His Lys Thr Leu Val Leu Leu Leu Gly Val Asp Pro Ser Arg
1670                1675                1680

Gln Leu Asp His Pro Leu Pro Thr Val His Pro Gln Val Thr Tyr
1685                1690                1695

Ala Tyr Met Lys Asn Met Trp Lys Ser Ala Arg Lys Ile Asp Ala
1700                1705                1710

Phe Gln His Met Gln His Phe Val Gln Thr Met Gln Gln Gln Ala
1715                1720                1725

Gln His Ala Ile Ala Thr Glu Asp Gln Gln His Lys Gln Glu Leu
1730                1735                1740

His Lys Leu Met Ala Arg Cys Phe Leu Lys Leu Gly Glu Trp Gln
1745                1750                1755

Leu Asn Leu Gln Gly Ile Asn Glu Ser Thr Ile Pro Lys Val Leu
1760                1765                1770

Gln Tyr Tyr Ser Ala Ala Thr Glu His Asp Arg Ser Trp Tyr Lys
1775                1780                1785

Ala Trp His Ala Trp Ala Val Met Asn Phe Glu Ala Val Leu His
1790                1795                1800

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830

```
Thr Ala Ala Thr Ala Thr Thr Thr Ala Ser Thr Glu Gly Ser Asn
        1835            1840            1845

Ser Glu Ser Glu Ala Glu Ser Thr Glu Asn Ser Pro Thr Pro Ser
    1850            1855            1860

Pro Leu Gln Lys Lys Val Thr Glu Asp Leu Ser Lys Thr Leu Leu
    1865            1870            1875

Met Tyr Thr Val Pro Ala Val Gln Gly Phe Phe Arg Ser Ile Ser
    1880            1885            1890

Leu Ser Arg Gly Asn Asn Leu Gln Asp Thr Leu Arg Val Leu Thr
    1895            1900            1905

Leu Trp Phe Asp Tyr Gly His Trp Pro Asp Val Asn Glu Ala Leu
    1910            1915            1920

Val Glu Gly Val Lys Ala Ile Gln Ile Asp Thr Trp Leu Gln Val
    1925            1930            1935

Ile Pro Gln Leu Ile Ala Arg Ile Asp Thr Pro Arg Pro Leu Val
    1940            1945            1950

Gly Arg Leu Ile His Gln Leu Leu Thr Asp Ile Gly Arg Tyr His
    1955            1960            1965

Pro Gln Ala Leu Ile Tyr Pro Leu Thr Val Ala Ser Lys Ser Thr
    1970            1975            1980

Thr Thr Ala Arg His Asn Ala Ala Asn Lys Ile Leu Lys Asn Met
    1985            1990            1995

Cys Glu His Ser Asn Thr Leu Val Gln Gln Ala Met Met Val Ser
    2000            2005            2010

Glu Glu Leu Ile Arg Val Ala Ile Leu Trp His Glu Met Trp His
    2015            2020            2025

Glu Gly Leu Glu Glu Ala Ser Arg Leu Tyr Phe Gly Glu Arg Asn
    2030            2035            2040

Val Lys Gly Met Phe Glu Val Leu Glu Pro Leu His Ala Met Met
    2045            2050            2055

Glu Arg Gly Pro Gln Thr Leu Lys Glu Thr Ser Phe Asn Gln Ala
    2060            2065            2070

Tyr Gly Arg Asp Leu Met Glu Ala Gln Glu Trp Cys Arg Lys Tyr
    2075            2080            2085

Met Lys Ser Gly Asn Val Lys Asp Leu Thr Gln Ala Trp Asp Leu
    2090            2095            2100

Tyr Tyr His Val Phe Arg Arg Ile Ser Lys Gln Leu Pro Gln Leu
    2105            2110            2115

Thr Ser Leu Glu Leu Gln Tyr Val Ser Pro Lys Leu Leu Met Cys
    2120            2125            2130

Arg Asp Leu Glu Leu Ala Val Pro Gly Thr Tyr Asp Pro Asn Gln
    2135            2140            2145

Pro Ile Ile Arg Ile Gln Ser Ile Ala Pro Ser Leu Gln Val Ile
    2150            2155            2160

Thr Ser Lys Gln Arg Pro Arg Lys Leu Thr Leu Met Gly Ser Asn
    2165            2170            2175

Gly His Glu Phe Val Phe Leu Leu Lys Gly His Glu Asp Leu Arg
    2180            2185            2190

Gln Asp Glu Arg Val Met Gln Leu Phe Gly Leu Val Asn Thr Leu
    2195            2200            2205

Leu Ala Asn Asp Pro Thr Ser Leu Arg Lys Asn Leu Ser Ile Gln
    2210            2215            2220

Arg Tyr Ala Val Ile Pro Leu Ser Thr Asn Ser Gly Leu Ile Gly
```

|  | 2225 |  |  | 2230 |  |  |  | 2235 |  |
|---|---|---|---|---|---|---|---|---|---|

Trp Val Pro His Cys Asp Thr Leu His Ala Leu Ile Arg Asp Tyr
    2240            2245              2250

Arg Glu Lys Lys Lys Ile Leu Leu Asn Ile Glu His Arg Ile Met
    2255            2260              2265

Leu Arg Met Ala Pro Asp Tyr Asp His Leu Thr Leu Met Gln Lys
    2270            2275              2280

Val Glu Val Phe Glu His Ala Val Asn Asn Thr Ala Gly Asp Asp
    2285            2290              2295

Leu Ala Lys Leu Leu Trp Leu Lys Ser Pro Ser Ser Glu Val Trp
    2300            2305              2310

Phe Asp Arg Arg Thr Asn Tyr Thr Arg Ser Leu Ala Val Met Ser
    2315            2320              2325

Met Val Gly Tyr Ile Leu Gly Leu Gly Asp Arg His Pro Ser Asn
    2330            2335              2340

Leu Met Leu Asp Arg Leu Ser Gly Lys Ile Leu His Ile Asp Phe
    2345            2350              2355

Gly Asp Cys Phe Glu Val Ala Met Thr Arg Glu Lys Phe Pro Glu
    2360            2365              2370

Lys Ile Pro Phe Arg Leu Thr Arg Met Leu Thr Asn Ala Met Glu
    2375            2380              2385

Val Thr Gly Leu Asp Gly Asn Tyr Arg Ile Thr Cys His Thr Val
    2390            2395              2400

Met Glu Val Leu Arg Glu His Lys Asp Ser Val Met Ala Val Leu
    2405            2410              2415

Glu Ala Phe Val Tyr Asp Pro Leu Leu Asn Trp Arg Leu Met Asp
    2420            2425              2430

Thr Asn Thr Lys Gly Asn Lys Arg Ser Arg Thr Arg Thr Asp Ser
    2435            2440              2445

Tyr Ser Ala Gly Gln Ser Val Glu Ile Leu Asp Gly Val Glu Leu
    2450            2455              2460

Gly Glu Pro Ala His Lys Lys Thr Gly Thr Thr Val Pro Glu Ser
    2465            2470              2475

Ile His Ser Phe Ile Gly Asp Gly Leu Val Lys Pro Glu Ala Leu
    2480            2485              2490

Asn Lys Lys Ala Ile Gln Ile Ile Asn Arg Val Arg Asp Lys Leu
    2495            2500              2505

Thr Gly Arg Asp Phe Ser His Asp Asp Thr Leu Asp Val Pro Thr
    2510            2515              2520

Gln Val Glu Leu Leu Ile Lys Gln Ala Thr Ser His Glu Asn Leu
    2525            2530              2535

Cys Gln Cys Tyr Ile Gly Trp Cys Pro Phe Trp
    2540            2545

<210> SEQ ID NO 2
<211> LENGTH: 8733
<212> TYPE: DNA
<213> ORGANISM: Homo sapiens
<220> FEATURE:
<221> NAME/KEY: CDS
<222> LOCATION: (122)..(7768)

<400> SEQUENCE: 2
gctcccggct tagaggacag cggggaaggc gggcggtggg gcaggggggcc tgaagcggcg    60 gtaccggtgc tggcggcggc agctgaggcc ttggccgaag ccgcgcgaac ctcagggcaa   120

```
g atg ctt gga acc gga cct gcc gcc gcc acc acc gct gcc acc aca tct      169
  Met Leu Gly Thr Gly Pro Ala Ala Ala Thr Thr Ala Ala Thr Thr Ser
  1               5                   10                  15 agc aat gtg agc gtc ctg cag cag ttt gcc agt ggc cta aag agc cgg         217
Ser Asn Val Ser Val Leu Gln Gln Phe Ala Ser Gly Leu Lys Ser Arg
            20                  25                  30 aat gag gaa acc agg gcc aaa gcc gcc aag gag ctc cag cac tat gtc         265
Asn Glu Glu Thr Arg Ala Lys Ala Ala Lys Glu Leu Gln His Tyr Val
        35                  40                  45 acc atg gaa ctc cga gag atg agt caa gag gag tct act cgc ttc tat         313
Thr Met Glu Leu Arg Glu Met Ser Gln Glu Glu Ser Thr Arg Phe Tyr
    50                  55                  60 gac caa ctg aac cat cac att ttt gaa ttg gtt tcc agc tca gat gcc         361
Asp Gln Leu Asn His His Ile Phe Glu Leu Val Ser Ser Ser Asp Ala
65              70                  75                  80 aat gag agg aaa ggt ggc atc ttg gcc ata gct agc ctc ata gga gtg         409
Asn Glu Arg Lys Gly Gly Ile Leu Ala Ile Ala Ser Leu Ile Gly Val
                85                  90                  95 gaa ggt ggg aat gcc acc cga att ggc aga ttt gcc aac tat ctt cgg         457
Glu Gly Gly Asn Ala Thr Arg Ile Gly Arg Phe Ala Asn Tyr Leu Arg
            100                 105                 110 aac ctc ctc ccc tcc aat gac cca gtt gtc atg gaa atg gca tcc aag         505
Asn Leu Leu Pro Ser Asn Asp Pro Val Val Met Glu Met Ala Ser Lys
        115                 120                 125 gcc att ggc cgt ctt gcc atg gca ggg gac act ttt acc gct gag tac         553
Ala Ile Gly Arg Leu Ala Met Ala Gly Asp Thr Phe Thr Ala Glu Tyr
    130                 135                 140 gtg gaa ttt gag gtg aag cga gcc ctg gaa tgg ctg ggt gct gac cgc         601
Val Glu Phe Glu Val Lys Arg Ala Leu Glu Trp Leu Gly Ala Asp Arg
145                 150                 155                 160 aat gag ggc cgg aga cat gca gct gtc ctg gtt ctc cgt gag ctg gcc         649
Asn Glu Gly Arg Arg His Ala Ala Val Leu Val Leu Arg Glu Leu Ala
                165                 170                 175 atc agc gtc cct acc ttc ttc cag caa gtg caa ccc ttc ttt gac             697
Ile Ser Val Pro Thr Phe Phe Gln Gln Val Gln Pro Phe Phe Asp
            180                 185                 190 aac att ttt gtg gcc gtg tgg gac ccc aaa cag gcc atc cgt gag gga         745
Asn Ile Phe Val Ala Val Trp Asp Pro Lys Gln Ala Ile Arg Glu Gly
        195                 200                 205 gct gta gcc gcc ctt cgt gcc tgt ctg att ctc aca acc cag cgt gag         793
Ala Val Ala Ala Leu Arg Ala Cys Leu Ile Leu Thr Thr Gln Arg Glu
    210                 215                 220 ccg aag gag atg cag aag cct cag tgg tac agg cac aca ttt gaa gaa         841
Pro Lys Glu Met Gln Lys Pro Gln Trp Tyr Arg His Thr Phe Glu Glu
225                 230                 235                 240 gca gag aag gga ttt gat gag acc ttg gcc aaa gag aag ggc atg aat         889
Ala Glu Lys Gly Phe Asp Glu Thr Leu Ala Lys Glu Lys Gly Met Asn
                245                 250                 255 cgg gat gat cgg atc cat gga gcc ttg ttg atc ctt aac gag ctg gtc         937
Arg Asp Asp Arg Ile His Gly Ala Leu Leu Ile Leu Asn Glu Leu Val
            260                 265                 270 cga atc agc agc atg gag gga gag cgt ctg aga gaa gaa atg gaa gaa         985
Arg Ile Ser Ser Met Glu Gly Glu Arg Leu Arg Glu Glu Met Glu Glu
        275                 280                 285 atc aca cag cag cag ctg gta cac gac aag tac tgc aaa gat ctc atg         1033
Ile Thr Gln Gln Gln Leu Val His Asp Lys Tyr Cys Lys Asp Leu Met
    290                 295                 300 ggc ttc gga aca aaa cct cgt cac att acc ccc ttc acc agt ttc cag         1081
Gly Phe Gly Thr Lys Pro Arg His Ile Thr Pro Phe Thr Ser Phe Gln
```

```
                                                                        -continued 305              310                315                320 gct gta cag ccc cag cag tca aat gcc ttg gtg ggg ctg ctg ggg tac    1129
Ala Val Gln Pro Gln Gln Ser Asn Ala Leu Val Gly Leu Leu Gly Tyr
                        325                330                335 agc tct cac caa ggc ctc atg gga ttt ggg acc tcc ccc agt cca gct    1177
Ser Ser His Gln Gly Leu Met Gly Phe Gly Thr Ser Pro Ser Pro Ala
                340                345                350 aag tcc acc ctg gtg gag agc cgg tgt tgc aga gac ttg atg gag gag    1225
Lys Ser Thr Leu Val Glu Ser Arg Cys Cys Arg Asp Leu Met Glu Glu
        355                360                365 aaa ttt gat cag gtg tgc cag tgg gtg ctg aaa tgc agg aat agc aag    1273
Lys Phe Asp Gln Val Cys Gln Trp Val Leu Lys Cys Arg Asn Ser Lys
    370                375                380 aac tcg ctg atc caa atg aca atc ctt aat ttg ttg ccc cgc ttg gct    1321
Asn Ser Leu Ile Gln Met Thr Ile Leu Asn Leu Leu Pro Arg Leu Ala
385                390                395                400 gca ttc cga cct tct gcc ttc aca gat acc cag tat ctc caa gat acc    1369
Ala Phe Arg Pro Ser Ala Phe Thr Asp Thr Gln Tyr Leu Gln Asp Thr
                405                410                415 atg aac cat gtc cta agc tgt gtc aag aag gag aag gaa cgt aca gcg    1417
Met Asn His Val Leu Ser Cys Val Lys Lys Glu Lys Glu Arg Thr Ala
                420                425                430 gcc ttc caa gcc ctg ggg cta ctt tct gtg gct gtg agg tct gag ttt    1465
Ala Phe Gln Ala Leu Gly Leu Leu Ser Val Ala Val Arg Ser Glu Phe
        435                440                445 aag gtc tat ttg cct cgc gtg ctg gac atc atc cga gcg gcc ctg ccc    1513
Lys Val Tyr Leu Pro Arg Val Leu Asp Ile Ile Arg Ala Ala Leu Pro
    450                455                460 cca aag gac ttc gcc cat aag agg cag aag gca atg cag gtg gat gcc    1561
Pro Lys Asp Phe Ala His Lys Arg Gln Lys Ala Met Gln Val Asp Ala
465                470                475                480 aca gtc ttc act tgc atc agc atg ctg gct cga gca atg ggg cca ggc    1609
Thr Val Phe Thr Cys Ile Ser Met Leu Ala Arg Ala Met Gly Pro Gly
                485                490                495 atc cag cag gat atc aag gag ctg ctg gag ccc atg ctg gca gtg gga    1657
Ile Gln Gln Asp Ile Lys Glu Leu Leu Glu Pro Met Leu Ala Val Gly
                500                505                510 cta agc cct gcc ctc act gca gtg ctc tac gac ctg agc cgt cag att    1705
Leu Ser Pro Ala Leu Thr Ala Val Leu Tyr Asp Leu Ser Arg Gln Ile
        515                520                525 cca cag cta aag aag gac att caa gat ggg cta ctg aaa atg ctg tcc    1753
Pro Gln Leu Lys Lys Asp Ile Gln Asp Gly Leu Leu Lys Met Leu Ser
    530                535                540 ctg gtc ctt atg cac aaa ccc ctt cgc cac cca ggc atg ccc aag ggc    1801
Leu Val Leu Met His Lys Pro Leu Arg His Pro Gly Met Pro Lys Gly
545                550                555                560 ctg gcc cat cag ctg gcc tct cct ggc ctc acg acc ctc cct gag gcc    1849
Leu Ala His Gln Leu Ala Ser Pro Gly Leu Thr Thr Leu Pro Glu Ala
                565                570                575 agc gat gtg ggc agc atc act ctt gcc ctc cga acg ctt ggc agc ttt    1897
Ser Asp Val Gly Ser Ile Thr Leu Ala Leu Arg Thr Leu Gly Ser Phe
                580                585                590 gaa ttt gaa ggc cac tct ctg acc caa ttt gtt cgc cac tgt gcg gat    1945
Glu Phe Glu Gly His Ser Leu Thr Gln Phe Val Arg His Cys Ala Asp
        595                600                605 cat ttc ctg aac agt gag cac aag gag atc cgc atg gag gct gcc cgc    1993
His Phe Leu Asn Ser Glu His Lys Glu Ile Arg Met Glu Ala Ala Arg
    610                615                620 acc tgc tcc cgc ctg ctc aca ccc tcc atc cac ctc atc agt ggc cat    2041
```

```
                Thr Cys Ser Arg Leu Leu Thr Pro Ser Ile His Leu Ile Ser Gly His
                625                 630                 635                 640 gct cat gtg gtt agc cag acc gca gtg caa gtg gtg gca gat gtg ctt          2089
Ala His Val Val Ser Gln Thr Ala Val Gln Val Val Ala Asp Val Leu
                645                 650                 655 agc aaa ctg ctc gta gtt ggg ata aca gat cct gac cct gac att cgc          2137
Ser Lys Leu Leu Val Val Gly Ile Thr Asp Pro Asp Pro Asp Ile Arg
            660                 665                 670 tac tgt gtc ttg gcg tcc ctg gac gag cgc ttt gat gca cac ctg gcc          2185
Tyr Cys Val Leu Ala Ser Leu Asp Glu Arg Phe Asp Ala His Leu Ala
        675                 680                 685 cag gcg gag aac ttg cag gcc ttg ttt gtg gct ctg aat gac cag gtg          2233
Gln Ala Glu Asn Leu Gln Ala Leu Phe Val Ala Leu Asn Asp Gln Val
    690                 695                 700 ttt gag atc cgg gag ctg gcc atc tgc act gtg ggc cga ctc agt agc          2281
Phe Glu Ile Arg Glu Leu Ala Ile Cys Thr Val Gly Arg Leu Ser Ser
705                 710                 715                 720 atg aac cct gcc ttt gtc atg cct ttc ctg cgc aag atg ctc atc cag          2329
Met Asn Pro Ala Phe Val Met Pro Phe Leu Arg Lys Met Leu Ile Gln
                725                 730                 735 att ttg aca gag ttg gag cac agt ggg att gga aga atc aaa gag cag          2377
Ile Leu Thr Glu Leu Glu His Ser Gly Ile Gly Arg Ile Lys Glu Gln
            740                 745                 750 agt gcc cgc atg ctg ggg cac ctg gtc tcc aat gcc ccc cga ctc atc          2425
Ser Ala Arg Met Leu Gly His Leu Val Ser Asn Ala Pro Arg Leu Ile
        755                 760                 765 cgc ccc tac atg gag cct att ctg aag gca tta att ttg aaa ctg aaa          2473
Arg Pro Tyr Met Glu Pro Ile Leu Lys Ala Leu Ile Leu Lys Leu Lys
    770                 775                 780 gat cca gac cct gat cca aac cca ggt gtg atc aat aat gtc ctg gca          2521
Asp Pro Asp Pro Asp Pro Asn Pro Gly Val Ile Asn Asn Val Leu Ala
785                 790                 795                 800 aca ata gga gaa ttg gca cag gtt agt ggc ctg gaa atg agg aaa tgg          2569
Thr Ile Gly Glu Leu Ala Gln Val Ser Gly Leu Glu Met Arg Lys Trp
                805                 810                 815 gtt gat gaa ctt ttt att atc atc atg gac atg ctc cag gat tcc tct          2617
Val Asp Glu Leu Phe Ile Ile Ile Met Asp Met Leu Gln Asp Ser Ser
            820                 825                 830 ttg ttg gcc aaa agg cag gtg gct ctg tgg acc ctg gga cag ttg gtg          2665
Leu Leu Ala Lys Arg Gln Val Ala Leu Trp Thr Leu Gly Gln Leu Val
        835                 840                 845 gcc agc act ggc tat gta gta gag ccc tac agg aag tac cct act ttg          2713
Ala Ser Thr Gly Tyr Val Val Glu Pro Tyr Arg Lys Tyr Pro Thr Leu
    850                 855                 860 ctt gag gtg cta ctg aat ttt ctg aag act gag cag aac cag ggt aca          2761
Leu Glu Val Leu Leu Asn Phe Leu Lys Thr Glu Gln Asn Gln Gly Thr
865                 870                 875                 880 cgc aga gag gcc atc cgt gtg tta ggg ctt tta ggg gct ttg gat cct          2809
Arg Arg Glu Ala Ile Arg Val Leu Gly Leu Leu Gly Ala Leu Asp Pro
                885                 890                 895 tac aag cac aaa gtg aac att ggc atg ata gac cag tcc cgg gat gcc          2857
Tyr Lys His Lys Val Asn Ile Gly Met Ile Asp Gln Ser Arg Asp Ala
            900                 905                 910 tct gct gtc agc ctg tca gaa tcc aag tca agt cag gat tcc tct gac          2905
Ser Ala Val Ser Leu Ser Glu Ser Lys Ser Ser Gln Asp Ser Ser Asp
        915                 920                 925 tat agc act agt gaa atg ctg gtc aac atg gga aac ttg cct ctg gat          2953
Tyr Ser Thr Ser Glu Met Leu Val Asn Met Gly Asn Leu Pro Leu Asp
    930                 935                 940
```

-continued

| | |
|---|---|
| gag ttc tac cca gct gtg tcc atg gtg gcc ctg atg cgg atc ttc cga<br>Glu Phe Tyr Pro Ala Val Ser Met Val Ala Leu Met Arg Ile Phe Arg<br>945                             950                    955                    960 | 3001 |
| gac cag tca ctc tct cat cat cac acc atg gtt gtc cag gcc atc acc<br>Asp Gln Ser Leu Ser His His His Thr Met Val Val Gln Ala Ile Thr<br>                    965                    970                    975 | 3049 |
| ttc atc ttc aag tcc ctg gga ctc aaa tgt gtg cag ttc ctg ccc cag<br>Phe Ile Phe Lys Ser Leu Gly Leu Lys Cys Val Gln Phe Leu Pro Gln<br>          980                    985                    990 | 3097 |
| gtc atg ccc acg ttc ctt aac gtc att cga gtc tgt gat ggg gcc atc<br>Val Met Pro Thr Phe Leu Asn Val Ile Arg Val Cys Asp Gly Ala Ile<br>995                          1000                  1005 | 3145 |
| cgg gaa ttt ttg ttc cag cag ctg gga atg ttg gtg tcc ttt gtg<br>Arg Glu Phe Leu Phe Gln Gln Leu Gly Met Leu Val Ser Phe Val<br>1010                   1015                 1020 | 3190 |
| aag agc cac atc aga cct tat atg gat gaa ata gtc acc ctc atg<br>Lys Ser His Ile Arg Pro Tyr Met Asp Glu Ile Val Thr Leu Met<br>1025                   1030                 1035 | 3235 |
| aga gaa ttc tgg gtc atg aac acc tca att cag agc acg atc att<br>Arg Glu Phe Trp Val Met Asn Thr Ser Ile Gln Ser Thr Ile Ile<br>1040                   1045                 1050 | 3280 |
| ctt ctc att gag caa att gtg gta gct ctt ggg ggt gaa ttt aag<br>Leu Leu Ile Glu Gln Ile Val Val Ala Leu Gly Gly Glu Phe Lys<br>1055                   1060                 1065 | 3325 |
| ctc tac ctg ccc cag ctg atc cca cac atg ctg cgt gtc ttc atg<br>Leu Tyr Leu Pro Gln Leu Ile Pro His Met Leu Arg Val Phe Met<br>1070                   1075                 1080 | 3370 |
| cat gac aac agc cca ggc cgc att gtc tct atc aag tta ctg gct<br>His Asp Asn Ser Pro Gly Arg Ile Val Ser Ile Lys Leu Leu Ala<br>1085                   1090                 1095 | 3415 |
| gca atc cag ctg ttt ggc gcc aac ctg gat gac tac ctg cat tta<br>Ala Ile Gln Leu Phe Gly Ala Asn Leu Asp Asp Tyr Leu His Leu<br>1100                   1105                 1110 | 3460 |
| ctg ctg cct cct att gtt aag ttg ttt gat gcc cct gaa gct cca<br>Leu Leu Pro Pro Ile Val Lys Leu Phe Asp Ala Pro Glu Ala Pro<br>1115                   1120                 1125 | 3505 |
| ctg cca tct cga aag gca gcg cta gag act gtg gac cgc ctg acg<br>Leu Pro Ser Arg Lys Ala Ala Leu Glu Thr Val Asp Arg Leu Thr<br>1130                   1135                 1140 | 3550 |
| gag tcc ctg gat ttc act gac tat gcc tcc cgg atc att cac cct<br>Glu Ser Leu Asp Phe Thr Asp Tyr Ala Ser Arg Ile Ile His Pro<br>1145                   1150                 1155 | 3595 |
| att gtt cga aca ctg gac cag agc cca gaa ctg cgc tcc aca gcc<br>Ile Val Arg Thr Leu Asp Gln Ser Pro Glu Leu Arg Ser Thr Ala<br>1160                   1165                 1170 | 3640 |
| atg gac acg ctg tct tca ctt gtt ttt cag ctg ggg aag aag tac<br>Met Asp Thr Leu Ser Ser Leu Val Phe Gln Leu Gly Lys Lys Tyr<br>1175                   1180                 1185 | 3685 |
| caa att ttc att cca atg gtg aat aaa gtt ctg gtg cga cac cga<br>Gln Ile Phe Ile Pro Met Val Asn Lys Val Leu Val Arg His Arg<br>1190                   1195                 1200 | 3730 |
| atc aat cat cag cgc tat gat gtg ctc atc tgc aga att gtc aag<br>Ile Asn His Gln Arg Tyr Asp Val Leu Ile Cys Arg Ile Val Lys<br>1205                   1210                 1215 | 3775 |
| gga tac aca ctt gct gat gaa gag gag gat cct ttg att tac cag<br>Gly Tyr Thr Leu Ala Asp Glu Glu Glu Asp Pro Leu Ile Tyr Gln<br>1220                   1225                 1230 | 3820 |
| cat cgg atg ctt agg agt ggc caa ggg gat gca ttg gct agt gga<br>His Arg Met Leu Arg Ser Gly Gln Gly Asp Ala Leu Ala Ser Gly<br>1235                   1240                 1245 | 3865 |

```
cca gtg gaa aca gga ccc atg aag aaa ctg cac gtc agc acc atc      3910
Pro Val Glu Thr Gly Pro Met Lys Lys Leu His Val Ser Thr Ile
    1250                1255                1260 aac ctc caa aag gcc tgg ggc gct gcc agg agg gtc tcc aaa gat      3955
Asn Leu Gln Lys Ala Trp Gly Ala Ala Arg Arg Val Ser Lys Asp
1265                1270                1275 gac tgg ctg gaa tgg ctg aga cgg ctg agc ctg gag ctg ctg aag      4000
Asp Trp Leu Glu Trp Leu Arg Arg Leu Ser Leu Glu Leu Leu Lys
    1280                1285                1290 gac tca tca tcg ccc tcc ctg cgc tcc tgc tgg gcc ctg gca cag      4045
Asp Ser Ser Ser Pro Ser Leu Arg Ser Cys Trp Ala Leu Ala Gln
1295                1300                1305 gcc tac aac ccg atg gcc agg gat ctc ttc aat gct gca ttt gtg      4090
Ala Tyr Asn Pro Met Ala Arg Asp Leu Phe Asn Ala Ala Phe Val
    1310                1315                1320 tcc tgc tgg tct gaa ctg aat gaa gat caa cag gat gag ctc atc      4135
Ser Cys Trp Ser Glu Leu Asn Glu Asp Gln Gln Asp Glu Leu Ile
1325                1330                1335 aga agc atc gag ttg gcc ctc acc tca caa gac atc gct gaa gtc      4180
Arg Ser Ile Glu Leu Ala Leu Thr Ser Gln Asp Ile Ala Glu Val
    1340                1345                1350 aca cag acc ctc tta aac ttg gct gaa ttc atg gaa cac agt gac      4225
Thr Gln Thr Leu Leu Asn Leu Ala Glu Phe Met Glu His Ser Asp
1355                1360                1365 aag ggc ccc ctg cca ctg aga gat gac aat ggc att gtt ctg ctg      4270
Lys Gly Pro Leu Pro Leu Arg Asp Asp Asn Gly Ile Val Leu Leu
    1370                1375                1380 ggt gag aga gct gcc aag tgc cga gca tat gcc aaa gca cta cac      4315
Gly Glu Arg Ala Ala Lys Cys Arg Ala Tyr Ala Lys Ala Leu His
1385                1390                1395 tac aaa gaa ctg gag ttc cag aaa ggc ccc acc cct gcc att cta      4360
Tyr Lys Glu Leu Glu Phe Gln Lys Gly Pro Thr Pro Ala Ile Leu
    1400                1405                1410 gaa tct ctc atc agc att aat aat aag cta cag cag ccg gag gca      4405
Glu Ser Leu Ile Ser Ile Asn Asn Lys Leu Gln Gln Pro Glu Ala
1415                1420                1425 gcg gcc gga gtg tta gaa tat gcc atg aaa cac ttt gga gag ctg      4450
Ala Ala Gly Val Leu Glu Tyr Ala Met Lys His Phe Gly Glu Leu
    1430                1435                1440 gag atc cag gct acc tgg tat gag aaa ctg cac gag tgg gag gat      4495
Glu Ile Gln Ala Thr Trp Tyr Glu Lys Leu His Glu Trp Glu Asp
1445                1450                1455 gcc ctt gtg gcc tat gac aag aaa atg gac acc aac aag gac gac      4540
Ala Leu Val Ala Tyr Asp Lys Lys Met Asp Thr Asn Lys Asp Asp
    1460                1465                1470 cca gag ctg atg ctg ggc cgc atg cgc tgc ctc gag gcc ttg ggg      4585
Pro Glu Leu Met Leu Gly Arg Met Arg Cys Leu Glu Ala Leu Gly
1475                1480                1485 gaa tgg ggt caa ctc cac cag cag tgc tgt gaa aag tgg acc ctg      4630
Glu Trp Gly Gln Leu His Gln Gln Cys Cys Glu Lys Trp Thr Leu
    1490                1495                1500 gtt aat gat gag acc caa gcc aag atg gcc cgg atg gct gct gca      4675
Val Asn Asp Glu Thr Gln Ala Lys Met Ala Arg Met Ala Ala Ala
1505                1510                1515 gct gca tgg ggt tta ggt cag tgg gac agc atg gaa gaa tac acc      4720
Ala Ala Trp Gly Leu Gly Gln Trp Asp Ser Met Glu Glu Tyr Thr
    1520                1525                1530 tgt atg atc cct cgg gac acc cat gat ggg gca ttt tat aga gct      4765
Cys Met Ile Pro Arg Asp Thr His Asp Gly Ala Phe Tyr Arg Ala
```

|     |     |     |     |     |     |     |     |     |     |     |     |     |
| --- | --- | --- | --- | --- | --- | --- | --- | --- | --- | --- | --- | --- |
|     |     | 1535 |     |     |     | 1540 |     |     |     | 1545 |     |     |
| gtg | ctg | gca | ctg | cat | cag | gac | ctc | ttc | tcc | ttg | gca | caa cag tgc | 4810 |
| Val | Leu | Ala | Leu | His | Gln | Asp | Leu | Phe | Ser | Leu | Ala | Gln Gln Cys |
|     | 1550 |     |     |     |     | 1555 |     |     |     |     | 1560 |     |
| att | gac | aag | gcc | agg | gac | ctg | ctg | gat | gct | gaa | tta | act gcg atg | 4855 |
| Ile | Asp | Lys | Ala | Arg | Asp | Leu | Leu | Asp | Ala | Glu | Leu | Thr Ala Met |
|     | 1565 |     |     |     |     | 1570 |     |     |     |     | 1575 |     |
| gca | gga | gag | agt | tac | agt | cgg | gca | tat | ggg | gcc | atg | gtt tct tgc | 4900 |
| Ala | Gly | Glu | Ser | Tyr | Ser | Arg | Ala | Tyr | Gly | Ala | Met | Val Ser Cys |
|     | 1580 |     |     |     |     | 1585 |     |     |     |     | 1590 |     |
| cac | atg | ctg | tcc | gag | ctg | gag | gag | gtt | atc | cag | tac | aaa ctt gtc | 4945 |
| His | Met | Leu | Ser | Glu | Leu | Glu | Glu | Val | Ile | Gln | Tyr | Lys Leu Val |
|     | 1595 |     |     |     |     | 1600 |     |     |     |     | 1605 |     |
| ccc | gag | cga | cga | gag | atc | atc | cgc | cag | atc | tgg | tgg | gag aga ctg | 4990 |
| Pro | Glu | Arg | Arg | Glu | Ile | Ile | Arg | Gln | Ile | Trp | Trp | Glu Arg Leu |
|     | 1610 |     |     |     |     | 1615 |     |     |     |     | 1620 |     |
| cag | ggc | tgc | cag | cgt | atc | gta | gag | gac | tgg | cag | aaa | atc ctt atg | 5035 |
| Gln | Gly | Cys | Gln | Arg | Ile | Val | Glu | Asp | Trp | Gln | Lys | Ile Leu Met |
|     | 1625 |     |     |     |     | 1630 |     |     |     |     | 1635 |     |
| gtg | cgg | tcc | ctt | gtg | gtc | agc | cct | cat | gaa | gac | atg | aga acc tgg | 5080 |
| Val | Arg | Ser | Leu | Val | Val | Ser | Pro | His | Glu | Asp | Met | Arg Thr Trp |
|     | 1640 |     |     |     |     | 1645 |     |     |     |     | 1650 |     |
| ctc | aag | tat | gca | agc | ctg | tgc | ggc | aag | agt | ggc | agg | ctg gct ctt | 5125 |
| Leu | Lys | Tyr | Ala | Ser | Leu | Cys | Gly | Lys | Ser | Gly | Arg | Leu Ala Leu |
|     | 1655 |     |     |     |     | 1660 |     |     |     |     | 1665 |     |
| gct | cat | aaa | act | tta | gtg | ttg | ctc | ctg | gga | gtt | gat | ccg tct cgg | 5170 |
| Ala | His | Lys | Thr | Leu | Val | Leu | Leu | Leu | Gly | Val | Asp | Pro Ser Arg |
|     | 1670 |     |     |     |     | 1675 |     |     |     |     | 1680 |     |
| caa | ctt | gac | cat | cct | ctg | cca | aca | gtt | cac | cct | cag | gtg acc tat | 5215 |
| Gln | Leu | Asp | His | Pro | Leu | Pro | Thr | Val | His | Pro | Gln | Val Thr Tyr |
|     | 1685 |     |     |     |     | 1690 |     |     |     |     | 1695 |     |
| gcc | tac | atg | aaa | aac | atg | tgg | aag | agt | gcc | cgc | aag | atc gat gcc | 5260 |
| Ala | Tyr | Met | Lys | Asn | Met | Trp | Lys | Ser | Ala | Arg | Lys | Ile Asp Ala |
|     | 1700 |     |     |     |     | 1705 |     |     |     |     | 1710 |     |
| ttc | cag | cac | atg | cag | cat | ttt | gtc | cag | acc | atg | cag | caa cag gcc | 5305 |
| Phe | Gln | His | Met | Gln | His | Phe | Val | Gln | Thr | Met | Gln | Gln Gln Ala |
|     | 1715 |     |     |     |     | 1720 |     |     |     |     | 1725 |     |
| cag | cat | gcc | atc | gct | act | gag | gac | cag | cag | cat | aag | cag gaa ctg | 5350 |
| Gln | His | Ala | Ile | Ala | Thr | Glu | Asp | Gln | Gln | His | Lys | Gln Glu Leu |
|     | 1730 |     |     |     |     | 1735 |     |     |     |     | 1740 |     |
| cac | aag | ctc | atg | gcc | cga | tgc | ttc | ctg | aaa | ctt | gga | gag tgg cag | 5395 |
| His | Lys | Leu | Met | Ala | Arg | Cys | Phe | Leu | Lys | Leu | Gly | Glu Trp Gln |
|     | 1745 |     |     |     |     | 1750 |     |     |     |     | 1755 |     |
| ctg | aat | cta | cag | ggc | atc | aat | gag | agc | aca | atc | ccc | aaa gtg ctg | 5440 |
| Leu | Asn | Leu | Gln | Gly | Ile | Asn | Glu | Ser | Thr | Ile | Pro | Lys Val Leu |
|     | 1760 |     |     |     |     | 1765 |     |     |     |     | 1770 |     |
| cag | tac | tac | agc | gcc | gcc | aca | gag | cac | gac | cgc | agc | tgg tac aag | 5485 |
| Gln | Tyr | Tyr | Ser | Ala | Ala | Thr | Glu | His | Asp | Arg | Ser | Trp Tyr Lys |
|     | 1775 |     |     |     |     | 1780 |     |     |     |     | 1785 |     |
| gcc | tgg | cat | gcg | tgg | gca | gtg | atg | aac | ttc | gaa | gct | gtg cta cac | 5530 |
| Ala | Trp | His | Ala | Trp | Ala | Val | Met | Asn | Phe | Glu | Ala | Val Leu His |
|     | 1790 |     |     |     |     | 1795 |     |     |     |     | 1800 |     |
| tac | aaa | cat | cag | aac | caa | gcc | cgc | gat | gag | aag | aag | aaa ctg cgt | 5575 |
| Tyr | Lys | His | Gln | Asn | Gln | Ala | Arg | Asp | Glu | Lys | Lys | Lys Leu Arg |
|     | 1805 |     |     |     |     | 1810 |     |     |     |     | 1815 |     |
| cat | gcc | agc | ggg | gcc | aac | atc | acc | aac | gcc | acc | act | gcc gcc acc | 5620 |
| His | Ala | Ser | Gly | Ala | Asn | Ile | Thr | Asn | Ala | Thr | Thr | Ala Ala Thr |
|     | 1820 |     |     |     |     | 1825 |     |     |     |     | 1830 |     |
| acg | gcc | gcc | act | gcc | acc | acc | act | gcc | agc | acc | gag | ggc agc aac | 5665 |

```
Thr Ala Ala Thr Ala Thr Thr Thr Ala Ser Thr Glu Gly Ser Asn
    1835            1840            1845 agt gag agc gag gcc gag agc acc gag aac agc ccc acc cca tcg      5710
Ser Glu Ser Glu Ala Glu Ser Thr Glu Asn Ser Pro Thr Pro Ser
    1850            1855            1860 ccg ctg cag aag aag gtc act gag gat ctg tcc aaa acc ctc ctg      5755
Pro Leu Gln Lys Lys Val Thr Glu Asp Leu Ser Lys Thr Leu Leu
    1865            1870            1875 atg tac acg gtg cct gcc gtc cag ggc ttc ttc cgt tcc atc tcc      5800
Met Tyr Thr Val Pro Ala Val Gln Gly Phe Phe Arg Ser Ile Ser
    1880            1885            1890 ttg tca cga ggc aac aac ctc cag gat aca ctc aga gtt ctc acc      5845
Leu Ser Arg Gly Asn Asn Leu Gln Asp Thr Leu Arg Val Leu Thr
    1895            1900            1905 tta tgg ttt gat tat ggt cac tgg cca gat gtc aat gag gcc tta      5890
Leu Trp Phe Asp Tyr Gly His Trp Pro Asp Val Asn Glu Ala Leu
    1910            1915            1920 gtg gag ggg gtg aaa gcc atc cag att gat acc tgg cta cag gtt      5935
Val Glu Gly Val Lys Ala Ile Gln Ile Asp Thr Trp Leu Gln Val
    1925            1930            1935 ata cct cag ctc att gca aga att gat acg ccc aga ccc ttg gtg      5980
Ile Pro Gln Leu Ile Ala Arg Ile Asp Thr Pro Arg Pro Leu Val
    1940            1945            1950 gga cgt ctc att cac cag ctt ctc aca gac att ggt cgg tac cac      6025
Gly Arg Leu Ile His Gln Leu Leu Thr Asp Ile Gly Arg Tyr His
    1955            1960            1965 ccc cag gcc ctc atc tac cca ctg aca gtg gct tct aag tct acc      6070
Pro Gln Ala Leu Ile Tyr Pro Leu Thr Val Ala Ser Lys Ser Thr
    1970            1975            1980 acg aca gcc cgg cac aat gca gcc aac aag att ctg aag aac atg      6115
Thr Thr Ala Arg His Asn Ala Ala Asn Lys Ile Leu Lys Asn Met
    1985            1990            1995 tgt gag cac agc aac acc ctg gtc cag cag gcc atg atg gtg agc      6160
Cys Glu His Ser Asn Thr Leu Val Gln Gln Ala Met Met Val Ser
    2000            2005            2010 gag gag ctg atc cga gtg gcc atc ctc tgg cat gag atg tgg cat      6205
Glu Glu Leu Ile Arg Val Ala Ile Leu Trp His Glu Met Trp His
    2015            2020            2025 gaa ggc ctg gaa gag gca tct cgt ttg tac ttt ggg gaa agg aac      6250
Glu Gly Leu Glu Glu Ala Ser Arg Leu Tyr Phe Gly Glu Arg Asn
    2030            2035            2040 gtg aaa ggc atg ttt gag gtg ctg gag ccc ttg cat gct atg atg      6295
Val Lys Gly Met Phe Glu Val Leu Glu Pro Leu His Ala Met Met
    2045            2050            2055 gaa cgg ggc ccc cag act ctg aag gaa aca tcc ttt aat cag gcc      6340
Glu Arg Gly Pro Gln Thr Leu Lys Glu Thr Ser Phe Asn Gln Ala
    2060            2065            2070 tat ggt cga gat tta atg gag gcc caa gag tgg tgc agg aag tac      6385
Tyr Gly Arg Asp Leu Met Glu Ala Gln Glu Trp Cys Arg Lys Tyr
    2075            2080            2085 atg aaa tca ggg aat gtc aag gac ctc acc caa gcc tgg gac ctc      6430
Met Lys Ser Gly Asn Val Lys Asp Leu Thr Gln Ala Trp Asp Leu
    2090            2095            2100 tat tat cat gtg ttc cga cga atc tca aag cag ctg cct cag ctc      6475
Tyr Tyr His Val Phe Arg Arg Ile Ser Lys Gln Leu Pro Gln Leu
    2105            2110            2115 aca tcc tta gag ctg caa tat gtt tcc cca aaa ctt ctg atg tgc      6520
Thr Ser Leu Glu Leu Gln Tyr Val Ser Pro Lys Leu Leu Met Cys
    2120            2125            2130
```

-continued

| | | | | | | | | | | |
|---|---|---|---|---|---|---|---|---|---|---|
| cgg | gac | ctt | gaa | ttg | gct | gtg | cca | gga | aca | tat | gac | ccc | aac | cag | 6565 |
| Arg | Asp | Leu | Glu | Leu | Ala | Val | Pro | Gly | Thr | Tyr | Asp | Pro | Asn | Gln | |
| 2135 | | | | 2140 | | | | | 2145 | | | | | | |

| cca | atc | att | cgc | att | cag | tcc | ata | gca | ccg | tct | ttg | caa | gtc | atc | 6610 |
| Pro | Ile | Ile | Arg | Ile | Gln | Ser | Ile | Ala | Pro | Ser | Leu | Gln | Val | Ile | |
| 2150 | | | | 2155 | | | | | 2160 | | | | | | |

| aca | tcc | aag | cag | agg | ccc | cgg | aaa | ttg | aca | ctt | atg | ggc | agc | aac | 6655 |
| Thr | Ser | Lys | Gln | Arg | Pro | Arg | Lys | Leu | Thr | Leu | Met | Gly | Ser | Asn | |
| 2165 | | | | 2170 | | | | | 2175 | | | | | | |

| gga | cat | gag | ttt | gtt | ttc | ctt | cta | aaa | ggc | cat | gaa | gat | ctg | cgc | 6700 |
| Gly | His | Glu | Phe | Val | Phe | Leu | Leu | Lys | Gly | His | Glu | Asp | Leu | Arg | |
| 2180 | | | | 2185 | | | | | 2190 | | | | | | |

| cag | gat | gag | cgt | gtg | atg | cag | ctc | ttc | ggc | ctg | gtt | aac | acc | ctt | 6745 |
| Gln | Asp | Glu | Arg | Val | Met | Gln | Leu | Phe | Gly | Leu | Val | Asn | Thr | Leu | |
| 2195 | | | | 2200 | | | | | 2205 | | | | | | |

| ctg | gcc | aat | gac | cca | aca | tct | ctt | cgg | aaa | aac | ctc | agc | atc | cag | 6790 |
| Leu | Ala | Asn | Asp | Pro | Thr | Ser | Leu | Arg | Lys | Asn | Leu | Ser | Ile | Gln | |
| 2210 | | | | 2215 | | | | | 2220 | | | | | | |

| aga | tac | gct | gtc | atc | cct | tta | tcg | acc | aac | tcg | ggc | ctc | att | ggc | 6835 |
| Arg | Tyr | Ala | Val | Ile | Pro | Leu | Ser | Thr | Asn | Ser | Gly | Leu | Ile | Gly | |
| 2225 | | | | 2230 | | | | | 2235 | | | | | | |

| tgg | gtt | ccc | cac | tgt | gac | aca | ctg | cac | gcc | ctc | atc | cgg | gac | tac | 6880 |
| Trp | Val | Pro | His | Cys | Asp | Thr | Leu | His | Ala | Leu | Ile | Arg | Asp | Tyr | |
| 2240 | | | | 2245 | | | | | 2250 | | | | | | |

| agg | gag | aag | aag | aag | atc | ctt | ctc | aac | atc | gag | cat | cgc | atc | atg | 6925 |
| Arg | Glu | Lys | Lys | Lys | Ile | Leu | Leu | Asn | Ile | Glu | His | Arg | Ile | Met | |
| 2255 | | | | 2260 | | | | | 2265 | | | | | | |

| ttg | cgg | atg | gct | ccg | gac | tat | gac | cac | ttg | act | ctg | atg | cag | aag | 6970 |
| Leu | Arg | Met | Ala | Pro | Asp | Tyr | Asp | His | Leu | Thr | Leu | Met | Gln | Lys | |
| 2270 | | | | 2275 | | | | | 2280 | | | | | | |

| gtg | gag | gtg | ttt | gag | cat | gcc | gtc | aat | aat | aca | gct | ggg | gac | gac | 7015 |
| Val | Glu | Val | Phe | Glu | His | Ala | Val | Asn | Asn | Thr | Ala | Gly | Asp | Asp | |
| 2285 | | | | 2290 | | | | | 2295 | | | | | | |

| ctg | gcc | aag | ctg | ctg | tgg | ctg | aaa | agc | ccc | agc | tcc | gag | gtg | tgg | 7060 |
| Leu | Ala | Lys | Leu | Leu | Trp | Leu | Lys | Ser | Pro | Ser | Ser | Glu | Val | Trp | |
| 2300 | | | | 2305 | | | | | 2310 | | | | | | |

| ttt | gac | cga | aga | acc | aat | tat | acc | cgt | tct | tta | gcg | gtc | atg | tca | 7105 |
| Phe | Asp | Arg | Arg | Thr | Asn | Tyr | Thr | Arg | Ser | Leu | Ala | Val | Met | Ser | |
| 2315 | | | | 2320 | | | | | 2325 | | | | | | |

| atg | gtt | ggg | tat | att | tta | ggc | ctg | gga | gat | aga | cac | cca | tcc | aac | 7150 |
| Met | Val | Gly | Tyr | Ile | Leu | Gly | Leu | Gly | Asp | Arg | His | Pro | Ser | Asn | |
| 2330 | | | | 2335 | | | | | 2340 | | | | | | |

| ctg | atg | ctg | gac | cgt | ctg | agt | ggg | aag | atc | ctg | cac | att | gac | ttt | 7195 |
| Leu | Met | Leu | Asp | Arg | Leu | Ser | Gly | Lys | Ile | Leu | His | Ile | Asp | Phe | |
| 2345 | | | | 2350 | | | | | 2355 | | | | | | |

| ggg | gac | tgc | ttt | gag | gtt | gct | atg | acc | cga | gag | aag | ttt | cca | gag | 7240 |
| Gly | Asp | Cys | Phe | Glu | Val | Ala | Met | Thr | Arg | Glu | Lys | Phe | Pro | Glu | |
| 2360 | | | | 2365 | | | | | 2370 | | | | | | |

| aag | att | cca | ttt | aga | cta | aca | aga | atg | ttg | acc | aat | gct | atg | gag | 7285 |
| Lys | Ile | Pro | Phe | Arg | Leu | Thr | Arg | Met | Leu | Thr | Asn | Ala | Met | Glu | |
| 2375 | | | | 2380 | | | | | 2385 | | | | | | |

| gtt | aca | ggc | ctg | gat | ggc | aac | tac | aga | atc | aca | tgc | cac | aca | gtg | 7330 |
| Val | Thr | Gly | Leu | Asp | Gly | Asn | Tyr | Arg | Ile | Thr | Cys | His | Thr | Val | |
| 2390 | | | | 2395 | | | | | 2400 | | | | | | |

| atg | gag | gtg | ctg | cga | gag | cac | aag | gac | agt | gtc | atg | gcc | gtg | ctg | 7375 |
| Met | Glu | Val | Leu | Arg | Glu | His | Lys | Asp | Ser | Val | Met | Ala | Val | Leu | |
| 2405 | | | | 2410 | | | | | 2415 | | | | | | |

| gaa | gcc | ttt | gtc | tat | gac | ccc | ttg | ctg | aac | tgg | agg | ctg | atg | gac | 7420 |
| Glu | Ala | Phe | Val | Tyr | Asp | Pro | Leu | Leu | Asn | Trp | Arg | Leu | Met | Asp | |
| 2420 | | | | 2425 | | | | | 2430 | | | | | | |

| | | | | | | | | | | | | |
|---|---|---|---|---|---|---|---|---|---|---|---|---|
|aca|aat|acc|aaa|ggc|aac|aag|cga|tcc|cga|acg|agg|acg gat tcc|7465
|Thr|Asn|Thr|Lys|Gly|Asn|Lys|Arg|Ser|Arg|Thr|Arg|Thr Asp Ser|
| |2435| | | | |2440| | | | |2445| | |

```
aca aat acc aaa ggc aac aag cga tcc cga acg agg acg gat tcc       7465
Thr Asn Thr Lys Gly Asn Lys Arg Ser Arg Thr Arg Thr Asp Ser
    2435                2440                2445 tac tct gct ggc cag tca gtc gaa att ttg gac ggt gtg gaa ctt       7510
Tyr Ser Ala Gly Gln Ser Val Glu Ile Leu Asp Gly Val Glu Leu
    2450                2455                2460 gga gag cca gcc cat aag aaa acg ggg acc aca gtg cca gaa tct       7555
Gly Glu Pro Ala His Lys Lys Thr Gly Thr Thr Val Pro Glu Ser
    2465                2470                2475 att cat tct ttc att gga gac ggt ttg gtg aaa cca gag gcc cta       7600
Ile His Ser Phe Ile Gly Asp Gly Leu Val Lys Pro Glu Ala Leu
    2480                2485                2490 aat aag aaa gct atc cag att att aac agg gtt cga gat aag ctc       7645
Asn Lys Lys Ala Ile Gln Ile Ile Asn Arg Val Arg Asp Lys Leu
    2495                2500                2505 act ggt cgg gac ttc tct cat gat gac act ttg gat gtt cca acg       7690
Thr Gly Arg Asp Phe Ser His Asp Asp Thr Leu Asp Val Pro Thr
    2510                2515                2520 caa gtt gag ctg ctc atc aaa caa gcg aca tcc cat gaa aac ctc       7735
Gln Val Glu Leu Leu Ile Lys Gln Ala Thr Ser His Glu Asn Leu
    2525                2530                2535 tgc cag tgc tat att ggc tgg tgc cct ttc tgg taactggagg            7778
Cys Gln Cys Tyr Ile Gly Trp Cys Pro Phe Trp
    2540                2545 cccagatgtg cccatcacgt tttttctgag gctttgtac tttagtaaat gcttccacta  7838
aactgaaacc atggtgagaa agtttgactt tgttaaatat tttgaaatgt aaatgaaaag  7898
aactactgta tattaaaagt tggtttgaac caactttcta gctgctgttg aagaatatat  7958
tgtcagaaac acaaggcttg atttggttcc caggacagtg aaacatagta ataccacgta  8018
aatcaagcca ttcattttgg ggaacagaag atccataact ttagaaatac gggttttgac  8078
ttaactcaca agagaactca tcataagtac ttgctgatgg aagaatgacc tagttgctcc  8138
tctcaacatg ggtacagcaa actcagcaca gccaagaagc ctcaggtcgt ggagaacatg  8198
gattaggatc ctagactgta aagacacaga agatgctgac ctcacccctg ccacctatcc  8258
caagacctca ctggtctgtg gacagcagca gaaatgtttg caagataggc caaaatgagt  8318
acaaaaggtc tgtcttccat cagacccagt gatgctgcga ctcacacgct tcaattcaag  8378
acctgaccgc tagtagggag gtttattcag atcgctggca gcctcggctg agcagatgca  8438 cagagggat cactgtgcag tgggaccacc ctcactggcc ttctgcagca gggttctggg   8498
atgttttcag tggtcaaaat actctgttta gagcaagggc tcagaaaaca gaaatactgt  8558
catggaggtg ctgaacacag ggaaggtctg gtacatattg gaaattatga gcagaacaaa  8618
tactcaacta aatgcacaaa gtataaagtg tagccatgtc tagacaccat gttgtatcag  8678
aataattttt gtgccaataa atgacatcag aattttaaac atatgtaaaa aaaaa       8733
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
gctgcatcac acgctcatcc         20

```
<210> SEQ ID NO 4
<211> LENGTH: 6
<212> TYPE: PRT
<213> ORGANISM: Homo sapiens

<400> SEQUENCE: 4

Tyr Met Val Met Glu Tyr
1               5

<210> SEQ ID NO 5
<211> LENGTH: 6
<212> TYPE: PRT
<213> ORGANISM: Homo sapiens

<400> SEQUENCE: 5

Ser Gly Leu Ile Gly Trp
1               5

<210> SEQ ID NO 6
<211> LENGTH: 6
<212> TYPE: PRT
<213> ORGANISM: Homo sapiens

<400> SEQUENCE: 6

Val Gly Leu Ile Glu Val
1               5

<210> SEQ ID NO 7
<211> LENGTH: 6
<212> TYPE: PRT
<213> ORGANISM: Homo sapiens

<400> SEQUENCE: 7

Gln Leu Ile Thr Gln Leu
1               5

<210> SEQ ID NO 8
<211> LENGTH: 6
<212> TYPE: PRT
<213> ORGANISM: Homo sapiens

<400> SEQUENCE: 8

Tyr Ile Ile Thr Glu Phe
1               5

<210> SEQ ID NO 9
<211> LENGTH: 6
<212> TYPE: PRT
<213> ORGANISM: Homo sapiens

<400> SEQUENCE: 9

Leu Val Ile Thr Glu Tyr
1               5

<210> SEQ ID NO 10
<211> LENGTH: 95
<212> TYPE: PRT
<213> ORGANISM: Homo sapiens

<400> SEQUENCE: 10

Thr Val Met Ala Ser Leu Arg Arg Pro Lys Arg Ile Ile Ile Arg Gly
1               5                   10                  15

His Asp Glu Arg Glu His Pro Phe Leu Val Lys Gly Gly Glu Asp Leu
            20                  25                  30
```

```
Arg Gln Asp Gln Arg Val Glu Gln Leu Phe Gln Val Met Asn Gly Ile
             35                  40                  45

Leu Ala Gln Asp Ser Ala Cys Ser Gln Arg Ala Leu Gln Leu Arg Thr
 50                  55                  60

Tyr Ser Val Val Pro Met Thr Ser Arg Leu Gly Leu Ile Glu Trp Leu
 65                  70                  75                  80

Glu Asn Thr Val Thr Leu Lys Asp Leu Leu Leu Asn Thr Met Ser
                     85                  90                  95

<210> SEQ ID NO 11
<211> LENGTH: 93
<212> TYPE: PRT
<213> ORGANISM: Homo sapiens

<400> SEQUENCE: 11

Glu Ile Leu Ala Ser Leu Gln Lys Pro Lys Ile Ser Leu Lys Gly
 1               5                  10                  15

Ser Asp Gly Lys Phe Tyr Ile Met Met Cys Lys Pro Lys Asp Asp Leu
                 20                  25                  30

Arg Lys Asp Cys Arg Leu Met Glu Phe Asn Ser Leu Ile Asn Lys Cys
             35                  40                  45

Leu Arg Lys Asp Ala Glu Ser Arg Arg Glu Leu His Ile Arg Thr
 50                  55                  60

Tyr Ala Val Ile Pro Leu Asn Asp Glu Cys Gly Ile Ile Glu Trp Val
 65                  70                  75                  80

Asn Asn Thr Ala Gly Leu Arg Pro Ile Leu Thr Lys Leu
                 85                  90

<210> SEQ ID NO 12
<211> LENGTH: 100
<212> TYPE: PRT
<213> ORGANISM: Homo sapiens

<400> SEQUENCE: 12

Arg Leu Ala Gly Gly Val Asn Leu Pro Lys Ile Ile Asp Cys Val Gly
 1               5                  10                  15

Ser Asp Gly Lys Glu Arg Arg Gln Leu Val Lys Gly Arg Asp Asp Leu
                 20                  25                  30

Arg Gln Asp Ala Val Met Gln Gln Val Phe Gln Met Cys Asn Thr Leu
             35                  40                  45

Leu Gln Arg Asn Thr Glu Thr Arg Lys Arg Lys Leu Thr Ile Cys Thr
 50                  55                  60

Tyr Lys Val Val Pro Leu Ser Gln Arg Ser Gly Val Leu Glu Trp Cys
 65                  70                  75                  80

Thr Gly Thr Val Pro Ile Gly Glu Phe Leu Val Asn Asn Glu Asp Gly
                 85                  90                  95

Ala His Lys Arg
             100

<210> SEQ ID NO 13
<211> LENGTH: 90
<212> TYPE: PRT
<213> ORGANISM: Homo sapiens

<400> SEQUENCE: 13

Lys Val Met Ala Ser Lys Lys Lys Pro Leu Trp Leu Glu Phe Lys Cys
 1               5                  10                  15

Ala Asp Pro Thr Ala Leu Ser Asn Glu Thr Ile Gly Ile Ile Phe Lys
```

```
                20                  25                  30

His Gly Asp Asp Leu Arg Gln Asp Met Leu Ile Leu Gln Ile Leu Arg
            35                  40                  45

Ile Met Glu Ser Ile Trp Gly Thr Glu Ser Leu Asp Leu Cys Leu Leu
 50                      55                  60

Pro Tyr Gly Cys Ile Ser Thr Gly Asp Lys Ile Gly Met Ile Glu Ile
 65                  70                  75                  80

Val Lys Asp Ala Thr Thr Ile Ala Lys Ile
                85                  90

<210> SEQ ID NO 14
<211> LENGTH: 88
<212> TYPE: PRT
<213> ORGANISM: Homo sapiens

<400> SEQUENCE: 14

Thr Phe Met Asp Ser Lys Met Lys Pro Leu Trp Ile Met Tyr Ser Asn
 1               5                  10                  15

Glu Glu Ala Gly Ser Gly Ser Val Gly Ile Ile Phe Lys Asn Gly
             20                  25                  30

Asp Asp Leu Arg Gln Asp Met Leu Thr Leu Gln Met Ile Gln Leu Met
            35                  40                  45

Asp Val Leu Trp Lys Gln Glu Gly Leu Asp Leu Arg Met Thr Pro Tyr
 50                      55                  60

Gly Cys Leu Pro Thr Gly Asp Arg Thr Gly Leu Ile Glu Val Val Leu
 65                  70                  75                  80

Arg Ser Asp Thr Ile Ala Asn Ile
                85

<210> SEQ ID NO 15
<211> LENGTH: 87
<212> TYPE: PRT
<213> ORGANISM: Homo sapiens

<400> SEQUENCE: 15

Lys Tyr Met Asp Ser Lys Met Lys Pro Leu Trp Leu Val Tyr Asn Asn
 1               5                  10                  15

Lys Val Phe Gly Glu Asp Ser Val Gly Val Ile Phe Lys Asn Gly Asp
             20                  25                  30

Asp Leu Arg Gln Asp Met Leu Thr Leu Gln Met Leu Arg Leu Met Asp
            35                  40                  45

Leu Leu Trp Lys Glu Ala Gly Leu Asp Leu Arg Met Leu Pro Tyr Gly
 50                      55                  60

Cys Leu Ala Thr Gly Asp Arg Ser Gly Leu Ile Glu Val Val Ser Thr
 65                  70                  75                  80

Ser Glu Thr Ile Ala Asp Ile
                85

<210> SEQ ID NO 16
<211> LENGTH: 91
<212> TYPE: PRT
<213> ORGANISM: Homo sapiens

<400> SEQUENCE: 16

Arg Ile Met Ser Ser Ala Lys Arg Pro Leu Trp Leu Asn Trp Glu Asn
 1               5                  10                  15

Pro Asp Ile Met Ser Glu Leu Leu Phe Gln Asn Asn Glu Ile Ile Phe
             20                  25                  30
```

```
Lys Asn Gly Asp Asp Leu Arg Gln Asp Met Leu Thr Leu Gln Ile Ile
        35                  40                  45

Arg Ile Met Glu Asn Ile Trp Gln Asn Gln Gly Leu Asp Leu Arg Met
    50                  55                  60

Leu Pro Tyr Gly Cys Leu Ser Ile Gly Asp Cys Val Gly Leu Ile Glu
65                  70                  75                  80

Val Val Arg Asn Ser His Thr Ile Met Gln Ile
                85                  90

<210> SEQ ID NO 17
<211> LENGTH: 92
<212> TYPE: PRT
<213> ORGANISM: Homo sapiens

<400> SEQUENCE: 17

Gln Val Ile Thr Ser Lys Gln Arg Pro Arg Lys Leu Thr Leu Met Gly
1               5                   10                  15

Ser Asn Gly His Glu Phe Val Phe Leu Leu Lys Gly His Glu Asp Leu
            20                  25                  30

Arg Gln Asp Glu Arg Val Met Gln Leu Phe Gly Leu Val Asn Thr Leu
        35                  40                  45

Leu Ala Asn Asp Pro Thr Ser Leu Arg Lys Asn Leu Ser Ile Gln Arg
    50                  55                  60

Tyr Ala Val Ile Pro Leu Ser Thr Asn Ser Gly Leu Ile Gly Trp Val
65                  70                  75                  80

Pro His Cys Asp Thr Leu His Ala Leu Ile Arg Asp
                85                  90
```

UNITED STATES PATENT AND TRADEMARK OFFICE
CERTIFICATE OF CORRECTION

PATENT NO. : 10,551,384 B2
APPLICATION NO. : 15/482340
DATED : February 4, 2020
INVENTOR(S) : Steven Zheng Page 1 of 1

It is certified that error appears in the above-identified patent and that said Letters Patent is hereby corrected as shown below:

In the Specification

Column 1, Lines 12-16, please delete "This invention was made with government support under P30-CA072720 awarded by the National Cancer Institute and R01 CA123391 and R01 CA166575 awarded by the National Insititues of Health. The government has certain rights in the invention." and insert -- This invention was made with government support under grant number CA166575 awarded by the National Institutes of Health. The government has certain rights in the invention. -- therefor.

Signed and Sealed this
Thirteenth Day of February, 2024

Katherine Kelly Vidal

Katherine Kelly Vidal
*Director of the United States Patent and Trademark Office*